United States Patent
Nirantar et al.

(10) Patent No.: US 12,209,266 B2
(45) Date of Patent: Jan. 28, 2025

(54) GENERATING NUCLEIC ACIDS WITH MODIFIED BASES USING RECOMBINANT TERMINAL DEOXYNUCLEOTIDYL TRANSFERASE

(71) Applicants: Illumina, Inc., San Diego, CA (US); Illumina Singapore Pte. Ltd., Singapore (SG)

(72) Inventors: Saurabh Rajendra Nirantar, Singapore (SG); Sergio Peisajovich, San Diego, CA (US); Eric Brustad, San Diego, CA (US)

(73) Assignees: Illumina, Inc., San Diego, CA (US); Illumina Singapore Pte. Ltd., Singapore (SG)

(*) Notice: Subject to any disclaimer, the term of this patent is extended or adjusted under 35 U.S.C. 154(b) by 753 days.

(21) Appl. No.: 17/317,700

(22) Filed: May 11, 2021

(65) Prior Publication Data
US 2021/0355518 A1  Nov. 18, 2021

Related U.S. Application Data

(60) Provisional application No. 63/023,736, filed on May 12, 2020.

(51) Int. Cl.
| C12N 9/12 | (2006.01) |
| C12P 19/34 | (2006.01) |

(52) U.S. Cl.
CPC ............ *C12P 19/34* (2013.01); *C12N 9/1264* (2013.01); *C12Y 207/07031* (2013.01); *C12Q 2521/131* (2013.01)

(58) Field of Classification Search
None
See application file for complete search history.

(56) References Cited

U.S. PATENT DOCUMENTS

| 7,494,797 B2 * | 2/2009 | Mueller ............... C12N 9/1264 435/194 |
| 9,012,022 B2 | 4/2015 | George et al. |
| 10,059,929 B2 | 8/2018 | Efcavitch et al. |
| 10,350,570 B2 | 7/2019 | Gunderson et al. |
| 10,583,415 B2 | 3/2020 | Banyai et al. |
| 2004/0185470 A1 | 9/2004 | Getts |
| 2005/0037991 A1 | 2/2005 | Bodepudi et al. |
| 2009/0280535 A1 | 11/2009 | Wang |
| 2011/0300534 A1 | 12/2011 | Chiou et al. |
| 2012/0122800 A1 | 5/2012 | Kadushin et al. |
| 2015/0072873 A1 | 3/2015 | Heinz et al. |
| 2015/0177235 A1 | 6/2015 | Casta et al. |
| 2016/0145605 A1 | 5/2016 | Kadonosono et al. |
| 2018/0023108 A1 | 1/2018 | Chen et al. |
| 2018/0037950 A1 | 2/2018 | Gunderson et al. |
| 2019/0390178 A1 | 12/2019 | Champion et al. |
| 2021/0009969 A1 | 1/2021 | Tubbs et al. |
| 2021/0187469 A1 | 6/2021 | George et al. |
| 2021/0355460 A1 | 11/2021 | Nirantar et al. |
| 2022/0025421 A1 | 1/2022 | Ee et al. |

FOREIGN PATENT DOCUMENTS

| EA | 021422 B1 | 6/2015 | |
| GB | 2553274 | 3/2018 | |
| WO | WO 2003/006625 | 1/2003 | |
| WO | WO2004018497 | 3/2004 | |
| WO | WO 2006/084132 | 8/2006 | |
| WO | WO 2006/097320 | 9/2006 | |
| WO | WO2014162307 | 10/2014 | |
| WO | WO2016064880 | 4/2016 | |
| WO | WO2016128731 | 8/2016 | |
| WO | WO 2017/034991 | 3/2017 | |
| WO | WO 2017/176679 | 10/2017 | |
| WO | WO 2017/202917 | 11/2017 | |
| WO | WO2017216472 | 12/2017 | |
| WO | WO 2017223517 | 12/2017 | |
| WO | WO2018217689 | 11/2018 | |
| WO | WO 2019/099420 | 5/2019 | |
| WO | WO-2019094524 A1 * | 5/2019 | .......... B01J 19/0046 |
| WO | WO 2019/195633 | 10/2019 | |
| WO | WO2020081985 | 4/2020 | |

(Continued)

OTHER PUBLICATIONS

Miura F, Fujino T, Kogashi K, Shibata Y, Miura M, Isobe H, Ito T. Triazole linking for preparation of a next-generation sequencing library from single-stranded DNA. Nucleic Acids Res. Sep. 19, 2018;46(16):e95. doi: 10.1093/nar/gky452. PMID: 29846671; PMCID: PMC6144795. (Year: 2018).*

Baranello et al., "DNA Break Mapping Reveals Topoisomerase II Activity Genome-Wide," International Journal of Molecular Sciences 2014, 15, 13111-13122.

Barthel et al., "Enhancing Terminal Deoxynucleotidyl Transferase Activity on Substrates with 30 Terminal Structures for Enzymatic De Novo DNA Synthesis," Genes 2020, 11(102), in 9 pages.

Beaucage & Caruthers, "Deoxynucleoside Phosphoramidites—A New Class Of Key Intermediates For Deoxypolynucleotide Synthesis," Tetrahedron Letters 1981, 22(20), 1859-1862.

Bentley et al., "Accurate whole human genome sequencing using reversible terminator chemistry," Nature 2008, 456, in 7 pages.

(Continued)

*Primary Examiner* — Allison M Fox
*Assistant Examiner* — Qinhua Gu
(74) *Attorney, Agent, or Firm* — Sheppard, Mullin, Richter & Hampton LLP

(57) ABSTRACT

Disclosed herein include methods of generating a single stranded deoxyribonucleic acid (ssDNA) scaffold comprising nucleotides with modified bases using a recombinant terminal deoxynucleotidyl transferase (TdT). The recombinant TdT can comprise an amino acid sequence that is at least 80% identical to a *Bos taurus* TdT, or a fragment thereof, and for example comprise one or more amino acid substitution mutations at one or more positions functionally equivalent to Glu191, Lys193, Glu194, Asp242, Lys287, Phe296, Met299, Thr342, and His420 in the *Bos taurus* TdT.

24 Claims, 8 Drawing Sheets

Specification includes a Sequence Listing.

(56) References Cited

FOREIGN PATENT DOCUMENTS

| WO | WO2020161480 | 8/2020 |
|---|---|---|
| WO | WO2021116270 | 6/2021 |
| WO | WO2021231477 | 11/2021 |
| WO | WO2021231483 | 11/2021 |

OTHER PUBLICATIONS

Bertocci et al., "Nonoverlapping Functions of DNA Polymerases Mu, Lambda, and Terminal Deoxynucleotidyltransferase during Immunoglobulin V(D)J Recombination In Vivo," Immunity 2006, 25, 31-41.
Bollum et al., "Thermal Conversion of Nonpriming Deoxyribonucleic Acid to Primer," The Journal of Biological Chemistry 1959, 234(10), 2733-2734.
Bollum et al., "Calf Thymus Polymerase," The Journal of Biological Chemistry 1960, 235(8), 2399-2403.
Bollum, "Terminal Deoxynucleotidyl Transferase," The Enzymes 1974, 10, 145-171.
Bornholt et al., "A DNA-Based Archival Storage System," ASPLOS 2016, 637-649.
Boule et al., "Comparison of the Two Murine Deoxynucleotidyltransferase Terminal Isoforms," The Journal of Biological Chemistry 2000, 275(37), 28984-28988.
Bowers et al., "Virtual Terminator nucleotides for next generation DNA sequencing," Nat Methods 2009, 6(8), 593-595.
Caruthers, "The Chemical Synthesis of DNA/RNA: Our Gift to Science," The Journal of Biological Chemistry 2013, 288(2), 1420-1427.
Chen et al., "The History and Advances of Reversible Terminators Used in New Generations of Sequencing Technology," Genomics Proteomics Bioinformatics 2013, 11, 34-40.
Chua et al., "Evolving a Thermostable Terminal Deoxynucleotidyl Transferase," ACS Synthetic Biology 2020, 9, 1725-1735.
Church et al., "Next-Generation Digital Information Storage in DNA," Sciencexpress 2012, in 2 pages.
Delarue et al., "Crystal structures of a template-independent DNA polymerase: murine terminal deoxynucleotidyltransferase," The EMBO Journal 2002, 21(3), 427-439.
Durowoju et al., "Differential Scanning Calorimetry—A Method for Assessing the Thermal Stability and Conformation of Protein Antigen," Journal of Visualized Experiments 2017, 121, in 8 pages.
Dymond et al., "Synthetic chromosome arms function in yeast and generate phenotypic diversity by design," Nature 2013, 477(7365), 471-476.
Extance, "Digital DNA; Could the Molecule known for storing genetic information also store the world's data?" Nature 2016, 537, 22-24.
Gavrieli et al., "Identification of Programmed Cell Death In Situ via Specific Labeling of Nuclear DNA Fragmentation," The Journal of Cell Biology 1992, 119(3), 493-501.
Gibson et al., "Creation of a Bacterial Cell Controlled by a Chemically Synthesized Genome," Science 2010, 329(5987), 52-56.
Goldman et al., "Toward practical high-capacity low-maintenance storage of digital information in synthesized DNA," Nature 2013, 494(7435), 77-80.
Gorczyca et al., "Detection of DNA Strand Breaks in Individual Apoptic Cells by in Situ Terminal Deoxynucleotidyl Transferase and Nick Translation Assays," Cancer Research 1993, 53, 1945-1951.
Hottin & Marx, "Structural Insights into the Processing of Nucleobase-Modified Nucleotides by DNA Polymerases," American Chemical Society 2016, 49, 418-427.
Hu et al., "A TdT-mediated cascade signal amplification strategy based on dendritic DNA matrix for label-free multifunctional electrochemical biosensing," Biosensors and Bioelectronics 2015, 63, 331-338.
Hutchinson et al., "Design and synthesis of a minimal bacterial genome," Science 2016, 351(6280), in 12 pages.
Hutter et al., "Labeled Nucleoside Triphosphates With Reversibly Terminating Aminoalkoxyl Groups," Nucleosides, Nucleotides and Nucleic Acids 2010, 29, 879-895.
Huynh and Partch, "Analysis of protein stability and ligand interactions by thermal shift assay," Current Protocols in Protein Science 2015, 79, in 19 pages.
International Search Report and Written Opinion dated Aug. 26, 2021 in PCT Patent Application No. PCT/US2021/031852.
International Search Report and Written Opinion dated Nov. 11, 2021 in PCT Patent Application No. PCT/US2021/031843.
Jarchow-Choy et al., "Fluorescent xDNA nucleotides as efficient substrates for a template-independent polymerase," Nucleic Acids Research 2011, 39(4), 1586-1894.
Jensen & Davis, "Template-Independent Enzymatic Oligonucleotide Synthesis (TiEOS): Its History, Prospects, and Challenges," Biochemistry 2018, in 12 pages.
Ju et al., "Four-color DNA sequencing by synthesis using cleavable fluorescent nucleotide reversible terminators," PNAS 2006, 103(52), 19635-19640.
Juárez et al., "A specific loop in human DNA polymerase mu allows switching between creative and DNA-instructed synthesis," Nucleic Acids Research 2006, 34(16), 4572-4582.
Kato et al., "Deoxynucleotide-polmerizing Enzymes of Calf Thymus Gland," The Journal of Biological Chemisty 1987, 242(11), 2780-2789.
Kelley et al., "The Phyre2 web portal for protein modelling, prediction and analysis," Nature Protocols 2015, 10(6), 845-858.
Lazinski & Camilli, "Homopolymer tail-mediated ligation PCR: a streamlined and highly efficient method for DNA cloning and library construction," BioTechniques 2013, 54(1), 25-34.
Lee et al., "Terminator-free template-independent enzymatic DNA synthesis for digital information storage," Nature Communications 2019, 10(2283), in 12 pages.
Lee et al., "Enzymatic DNA synthesis for digital information storage," bioRxiv 2018, in 31 pages.
Leproust et al., "Synthesis of high-quality libraries of long (150mer) oligonucleotides by a novel depurination controlled process," Nucleic Acids Research 2010, 38(8), 2522-2540.
Liang et al., "Synthetic biology: putting synthesis into biology," WIREs Syst Biol Med 2011, 3, 7-20.
Loc'H et al., "Structural evidence for an in trans base selection mechanism involving Loop1 in polymerase μ at an NHEJ double-strand break junction," The Journal of Biological Chemistry 2019, 294(27), 10579-10595.
Loc'H, "Terminal deoxynucleotidyltransferase: the story of an untemplated DNA polymerase capable of DNA bridging and templated synthesis across strands," Current Opinion in Structural Biology 2018, 53, 22-31.
Moon et al., "The X Family Portrait: Structural Insights into Biological Functions of X Family Polymerases," DNA Repair 2007, 6(12), 1709-1725.
Motea & Berdis, "Terminal Deoxynucleotidyl Transferase: The Story of a Misguided DNA Polymerase," Biochimica et Biophysica Acta 2010, 1804(5), 1151-1166.
Musil et al., "FireProt: web server for automated design of thermostable proteins," Nucleic Acids Research 2017, 45, W393-W399.
Ostrov et al., "Design, synthesis, and testing toward a 57-codon genome," Science 2016, 353(6301), 819-822.
Palluk et al., "De novo DNA synthesis using polymerase-nucleotide conjugates," Nature Biotechnology 2018, 1-6.
Peng et al., "TELP, a sensitive and versatile library construction method for next-generation sequencing," Nucleic Acids Research 2014, 43(6), e35, in 13 pages.
Pina-Anguilar et al., "Revival of Extinct Species Using Nuclear Transfer: Hope for the Mammoth, True for the Pyrenean Ibex, But Is It Time for "Conservation Cloning"?," Cloning and Stem Cells 2009, 11(3), in 6 pages.
Richardson et al., "Design of a synthetic yeast genome," Science 2017, 355, 1040-1044.
Romain et al., "Conferring a template-dependent polymerase activity to terminal deoxynucleotidyltransferase by mutations in the Loop1 region," Nucleic Acids Research 2009, 37(14), 4642-4656.

(56) References Cited

OTHER PUBLICATIONS

Rosa et al., "Meltdown: A Tool to Help in the Interpretation of Thermal Melt Curves Acquired by Differential Scanning Fluorimetry," Journal of Biomolecular Screening 2015, 20(7), 898-905.
Ruparel et al., "Design and synthesis of a 3'-O-allyl photocleavable fluorescent nucleotide as a reversible terminator for DNA sequencing by synthesis," PNAS 2005, 102(17), 5932-5937.
Sarac & Hollenstein, "Terminal Deoxynucleotidyl Transferase in the Synthesis and Modification of Nucleic Acids," ChemBioChem 2019, 20, 860-871.
Sharma et al., "Terminal deoxynucleotidyl transferase dUTP nick end labeling (TUNEL) assay using bench top flow cytometer for evaluation of sperm DNA fragmentation in fertility laboratories: protocol, reference values, and quality control," The Journal of Assisted Reproduction and Genetics 2016, 33, 291-300.
Slavíčková et al., "Additions of Thiols to 7-Vinyl-7-deazaadenine Nucleosides and Nucleotides. Synthesis of Hydrophobic Derivatives of 2'-Deoxyadenosine, dATP and DNA," The Journal of Organic Chemistry 2016, 81, 11115-11125.
Tauraitė et al., "Modified Nucleotides as Substrates of Terminal Deoxynucleotidyl Transferase," Molecules 2017, 22(672), in 16 pages.
Tjong et al., "Amplified On-Chip Fluorescence Detection of DNA Hybridization by Surface-Initiated Enzymatic Polymerization," Analytical Chemistry 2011, 5153-5159.
Tjong et al., Direct Fluorescence Detection of RNA on Microarrays by Surface-Initiated Enzymatic Polymerization, Analytical Chemistry 2013, 85, 426-433.
Woolly Mammoth Revival, "Why Bring Back the Woolly Mammoth?" Revive & Restore 2021, in 3 pages. http://reviverestore.org/projects/woolly-mammoth/.
Yang et al., "Mutational Analysis of Residues in the Nucleotide Binding Domain of Human Terminal Deoxynucleotidyl Transferase," The Journal of Biological Chemistry 1994, 269(16), 11859-11868.
Yazdi et al., "Portable and Error-Free DNA-Based Data Storage," Scientific Reports 2017, 7(5011), 1-6.
Gopinath & Rothemund, "Optimized assembly and covalent coupling of single-molecule DNA origami nanoarrays," ACS Nano 2014, 8(12), 12030-12040.
Gu et al., "Enzymatic synthesis of nucleobase-modified single-stranded DNA offers tunable resistance to nuclease degradation," Biomacromolecules 2018, 19(8), 3525-3535.
Lapiene et al., "Conjugation of fluorescent proteins with DNA oligonucleotides," Bioconjugate Chemistry 2010, 21(5), 921-927.
Liu et al., "Encoding function into polypeptide-oligonucleotide precision biopolymers," Chemical Communications 2018, 54(83), 11797-11800.
Mutlu et al., "Sulfur chemistry in polymer and materials science," Macromolecular Rapid Communications 2019, 40(1), in 51 pages.
Newkome & Shreiner, "Poly (amidoamine), polypropylenimine, and related dendrimers and dendrons possessing different 1→2 branching motifs: An overview of the divergent procedures," Polymer 2008, 49(1), 1-173.
Nykänen et al., "An efficient and stable star-shaped plasticizer for starch: cyclic phosphazene with hydrogen bonding aminoethoxy ethanol side chains," Green Chemistry 2014, 16(9), 4339-4350.
Rozenberg & Tenne, "Polymer-assisted fabrication of nanoparticles and nanocomposites," Progress in Polymer Science 2008, 33(1), 40-112.
Sirivolu et al., "DNA with Branched Internal Side Chains: Synthesis of 5-Tripropargylamine-dU and Conjugation by an Azide-Alkyne Double Click Reaction," ChemBioChem 2008, 9(14), 2305-2316.
Winz et al., "Nucleotidyl transferase assisted DNA labeling with different click chemistries," Nucleic Acids Research 2015, 43(17), in 10 pages.
Deshpande et al., "Enzymatic synthesis and modification of high molecular weight DNA using terminal deoxynucleotidyl transferase," Methods Enzymol 2019, 627, 163-188.
Final Office Action dated Oct. 12, 2022 in U.S. Appl. No. 17/317,721.
Guo et al., "Protein tolerance to random amino acid change," PNAS 2004, 101(25), 9205-9210.
Hayes et al., "Combining computational and experimental screening for rapid optimization of protein properties," PNAS 2002, 99(25), 15926-15931.
Ngo et al., "Computational Complexity, Protein Structure Prediction, and the Levinthal Paradox," The Protein Folding Problem and Tertiary Structure Prediction 1994, 492-495.
Non-final Office Action dated May 16, 2022 in U.S. Appl. No. 17/317,721.
International Search Report and Written Opinion dated Jan. 24, 2022 in PCT Patent Application No. PCT/US2021/031843.
Jena Bioscience, "Azide-PEG4-aminoallyl-dUTP Data Sheet", 2020, in 1 page.
Restriction Requirement dated Feb. 22, 2022 in U.S. Appl. No. 17/317,721.
Sørensen et al., "Enzymatic Ligation of Large Biomolecules to DNA", ACS Nano 2013, 7(9), 8098-8104.
Winz et al., "Site-specific one-pot triple click labeling for DNA and RNA", Chemical Communications 2018, 54(83), 11781-11784.

\* cited by examiner

FIG. 1
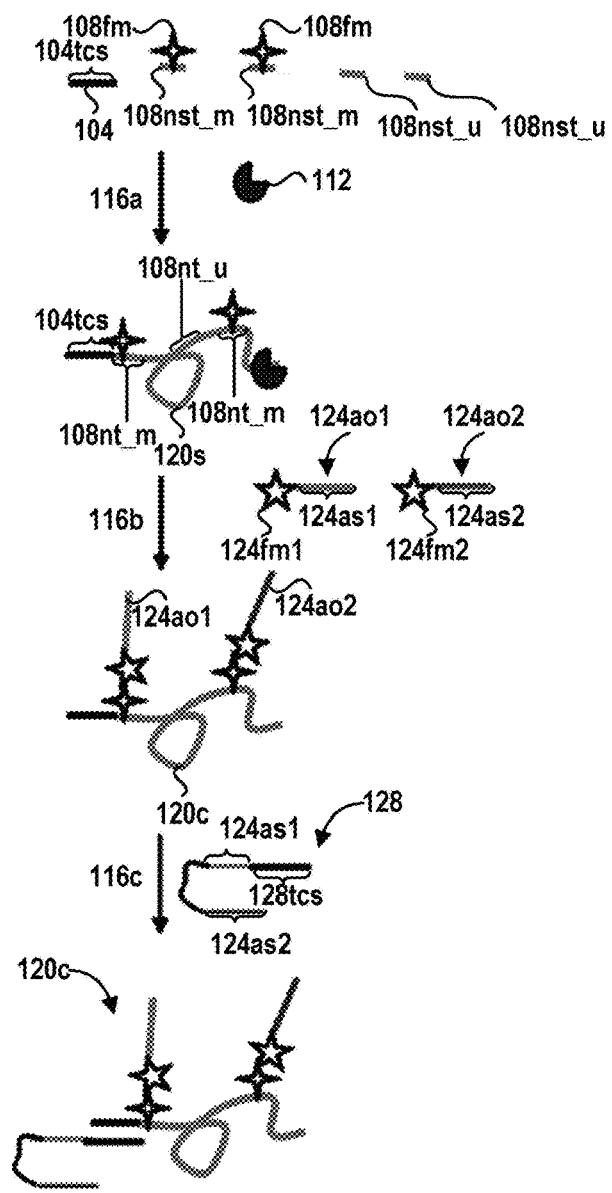
Single template capture per ssDNA
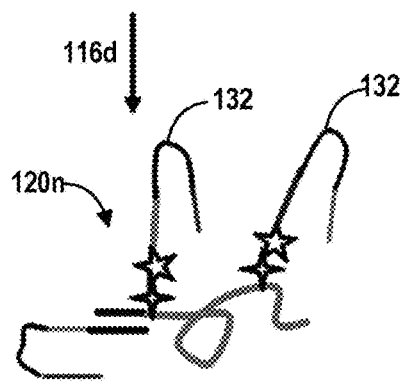
DNA particle with multiple template copies

FIG. 2

|  |  | His tag | Thrombin cleavage site | SUMO fragment |  |  |
|---|---|---|---|---|---|---|

```
SEQ ID NO: 14   SUMO-TdT        1  MGSSHHHHHH GSGLVPRGSA SMSDSEVNQE AKPEVKPEVK PETHINLKVS DGSSEIFFKI    60

SUMO-TdT       60  KKTTPLRRLM EAFAKRQGKE MDSIRFLYDG IRIQADQTPE DLDMEDNDII EAHREQIGGE   120

SEQ ID NO: 1    SUMO-TdT      121  LMRTDYSATP NPGFQKTPPL AVKKISQYAC QRKTTLNNYN HIFTDAFEIL AENSFNE     180
Amino Acids 139- Bovine TdT   139     RTDYSATP NPGFQKTPPL AVKKISQYAC QRKTTLNNYN HIFTDAFEIL AENSFNE     196
520 of SEQ ID
NO: 12          SUMO-TdT      181  VSYVTFMRAA SVLKSLPFTI ISMKDTEGIP CLGDKVKCII EEIIEGESS EVKAVLNDER    240
                Bovine TdT    197  VSYVTFMRAA SVLKSLPFTI ISMKDTEGIP CLGDKVKCII EEIIEGESS EVKAVLNDER    256

SUMO-TdT      241  YQSFKLFTSV FGVGLKTSEK WFRMGFRSLS IMSDKTLK TKQKAGFLY YEDLVSCVTR    300
                Bovine TdT    257  YQSFKLFTSV FGVGLKTSEK WFRMGFRSLS IMSDKTLK TKQKAGFLY YEDLVSCVTR    316

SUMO-TdT      301  AEAEAVGVLV KEAVWAFLPD AFVTM GGFR RGKKIGHDVD FLITSPGSAE DEEQLLPKVI   360
                Bovine TdT     17  AEAEAVGVLV KEAVWAFLPD AFVTM GGFR RGKKIGHDVD FLITSPGSAE DEEQLLPKVI   376

SUMO-TdT      361  NLWEKKGLLL YYDLVESTFE KFKLPSRQVD TLDHFQKCFL ILKI HQRVD SSKSNQQEGK   420
                Bovine TdT    377  NLWEKKGLLL YYDLVESTFE KFKLPSRQVD TLDHFQKCFL ILKI HQRVD SSKSNQQEGK   436

SUMO-TdT      421  TWKAIRVDLV MCPYENRAFA LLGWTGSRQF ERDIRRYATH ERKMMLDNHA LYDKTKRVFL   480
                Bovine TdT    437  TWKAIRVDLV MCPYENRAFA LLGWTGSRQF ERDIRRYATH ERKMMLDNHA LYDKTKRVFL   496

SUMO-TdT      481  KAESEEEIFA HLGLDYIEPW ERNA   504
                Bovine TdT    497  KAESEEEIFA HLGLDYIEPW ERNA   520
```

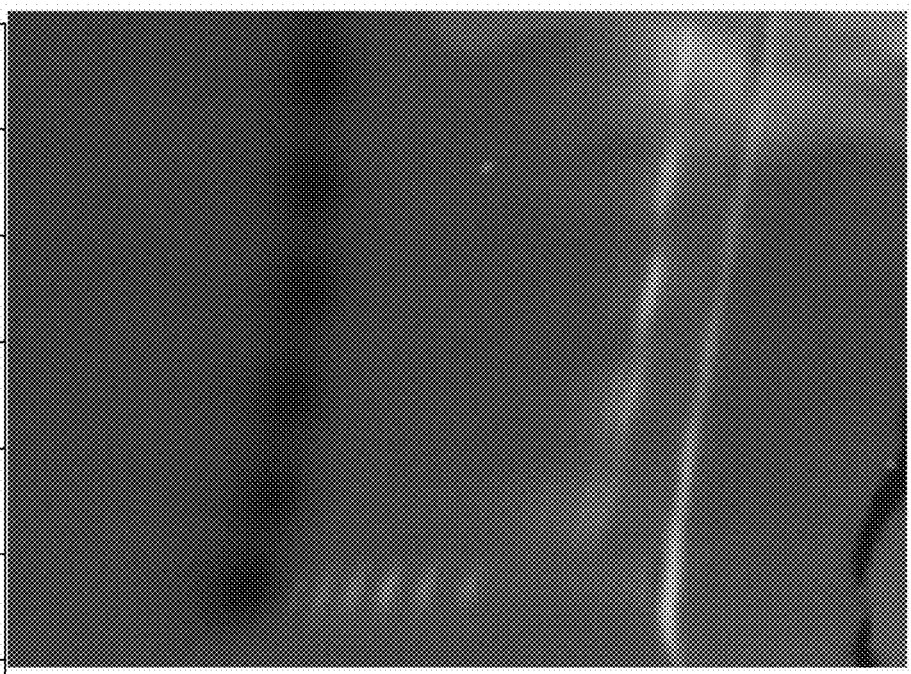
FIG. 5A

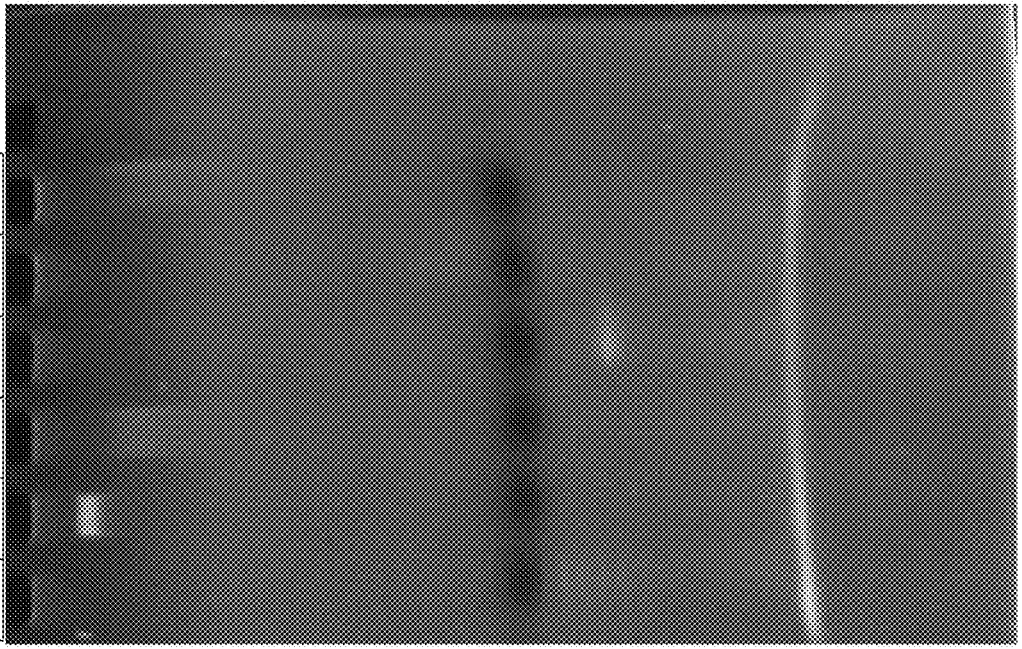
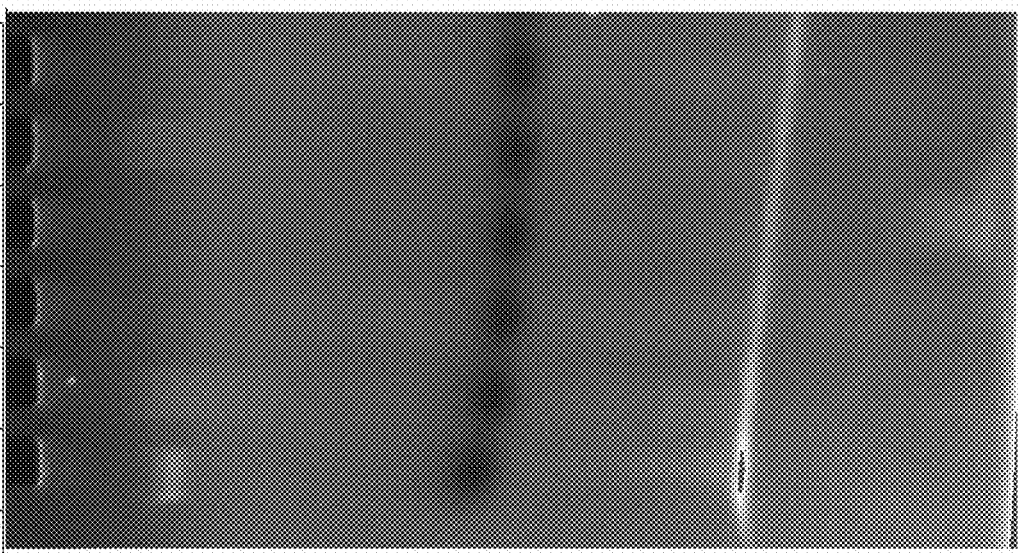
FIG. 5B

GENERATING NUCLEIC ACIDS WITH MODIFIED BASES USING RECOMBINANT TERMINAL DEOXYNUCLEOTIDYL TRANSFERASE

CROSS-REFERENCE TO RELATED APPLICATIONS

This application claims the benefit of priority to U.S. Provisional Patent Application No. 63/023,736, filed May 12, 2020, the content of which is incorporated herein by reference in its entirety.

REFERENCE TO SEQUENCE LISTING

The present application is being filed along with a Sequence Listing in electronic format. The Sequence Listing is provided as a file entitled Sequences_Listing_47CX-311973-US, created May 11, 2020, which is 52 kilobytes in size. The information in the electronic format of the Sequence Listing is incorporated herein by reference in its entirety.

BACKGROUND

Field

The present disclosure relates generally to the field of generating nucleic acids, for example generating nucleic acids with modified bases.

Description of the Related Art

Monoclonality can improve efficiency of sequencing-by-synthesis (SBS). Monoclonality for SBS can occur when individual template polynucleotides seed and cluster, or the polynucleotide products from seeding and clustering from individual template polynucleotides, are in spatially distinct positions on a substrate surface.

SUMMARY

Disclosed herein include embodiments of a method of modifying a nucleic acid. In some embodiments, the method comprises: (a) providing a single stranded deoxyribonucleic acid (ssDNA) and a nucleoside triphosphate comprising a modified base. The method can comprise: (b) contacting the ssDNA and the nucleoside triphosphate comprising the modified base with a recombinant terminal deoxynucleotidyl transferase (TdT) to generate a ssDNA scaffold. The ssDNA scaffold can comprise the ssDNA incorporated with one or more nucleotides comprising the modified base from the nucleoside triphosphate. The recombinant TdT can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the *Bos taurus* TdT of SEQ ID NO: 12.

In some embodiments, the method further comprises: (c) contacting the ssDNA scaffold with a first adapter oligonucleotide and a second adapter oligonucleotide to generate a nucleic acid carrier. Contacting the ssDNA scaffold with the first adapter oligonucleotide can comprise contacting the ssDNA scaffold with a first adapter comprising the first adapter oligonucleotide and a first polymer. Contacting the ssDNA scaffold with the second adapter oligonucleotide can comprise contacting the ssDNA scaffold with a second adapter comprising the second adapter oligonucleotide and a second polymer. The first adapter can comprise the first adapter oligonucleotide and the first polymer covalently linked. The second adapter can comprise the second adapter oligonucleotide and the second polymer covalently linked. The ssDNA scaffold can comprise a third polymer. The first adapter oligonucleotide can comprise a first adapter sequence, or a reverse complement thereof. The second adapter oligonucleotide can comprise a second adapter sequence, or a reverse complement thereof. The nucleic acid carrier can comprise the ssDNA scaffold attached to the first adapter oligonucleotide and the second adapter oligonucleotide. In some embodiments, the method further comprises: (d) providing a nucleic acid template comprising the first adapter sequence, or a reverse complement thereof, the second adapter sequence, or a reverse complement thereof, and a nucleic acid hybridization sequence. The method can comprise: (e) contacting the nucleic acid carrier with the nucleic acid template to generate the nucleic acid carrier having the nucleic acid template hybridized to a template capture site of the nucleic acid carrier via the nucleic acid hybridization sequence of the nucleic acid template. The method can comprise: (f) performing amplification on the nucleic acid carrier hybridized with the nucleic acid template to generate a plurality of amplified nucleic acids each comprising the first adapter oligonucleotides and the second adapter oligonucleotides extended to comprise a sequence of the nucleic acid template, or a reverse complement thereof. The amplification can be, for example, bridge amplification or exclusion amplification. The method can comprise: (g) determining the sequence of the nucleic acid template using the plurality of amplified nucleic acids.

Disclosed herein include embodiments of a method of modifying a nucleic acid. In some embodiments, the method comprises: (a) providing a first nucleic acid and a first nucleoside triphosphate comprising a first modified base. The method can comprise: (b) contacting the first nucleic acid and the first nucleoside triphosphate comprising the first modified base with a recombinant terminal deoxynucleotidyl transferase (TdT) for a first reaction time at a first temperature in a first reaction to generate a second nucleic acid. The second nucleic acid can comprise the first nucleic acid incorporated with one or more first nucleotides comprising the first modified base from the first nucleoside triphosphate. The recombinant TdT can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the *Bos taurus* TdT of SEQ ID NO: 12.

In some embodiments, one or more of the first nucleic acid and the second nucleic acid comprise a single stranded nucleic acid, a double stranded nucleic acid with a 3' overhang, a double stranded nucleic acid with a 3' recess, or a combination thereof. One or more of the first nucleic acid and the second nucleic acid can comprise deoxyribonucleic acid (DNA). At least 50% of nucleotides of one or more of the first nucleic acid and the second nucleic acid can comprise deoxyribonucleotides. One or more of the first nucleic acid and the second nucleic acid can comprise a single stranded deoxyribonucleic acid (ssDNA). One or more of the first nucleic acid and the second nucleic acid can comprise at least one ribonucleotide.

In some embodiments, the second nucleic acid comprises the first nucleic acid incorporated with two or more, or three or more, of the first nucleotides comprising the first modified base. The two or more, or three or more, of the first nucleotides comprising the first modified base in the second nucleic acid can be consecutive. The first modified base of the first nucleoside triphosphate can comprise a modified adenine, a modified guanine, a modified cytosine, a modified thymine, or a modified uracil. The first nucleoside triphosphate can comprise 5-(15-Azido-4,7,10,13-tetraoxa-pentadecanoyl-aminoallyl)-2'-deoxyuridine-5'-triphosphate (Azide-PEG4-aminoallyl-dUTP), $N^6$-(6-Azido)hexyl-3'-deoxyadenosine-5'-triphosphate ($N^6$-(6-Azido)hexyl-3'-dATP), or a combination thereof. In some embodiments, the first nucleoside triphosphate comprises the first modified base and a first accessory oligonucleotide covalently linked.

In some embodiments, the first reaction time is at least 1 second. The first temperature can be at least 16° C. to at least 58° C. A concentration of the first nucleic acid in the first reaction can be at least 10 nM. A concentration of the first nucleoside triphosphate in the first reaction can be at least 0.1 µM. The concentration of the recombinant TdT in the first reaction can be at least 10 nM.

In some embodiments, providing the first nucleic acid and the first nucleoside triphosphate comprising the first modified base comprises: providing the first nucleic acid, the first nucleoside triphosphate comprising the first modified base, and a second nucleoside triphosphate. Contacting the first nucleic acid and the first nucleoside triphosphate comprising the first modified base with the recombinant TdT can comprise: contacting the first nucleic acid, the first nucleoside triphosphate comprising the first modified base, and the second nucleoside triphosphate with the recombinant TdT for the first reaction time at the first temperature in the first reaction to generate the second nucleic acid. The second nucleic acid can comprise the first nucleic acid incorporated with (i) one or more of the first nucleotides comprising the first modified base from the first nucleoside triphosphate and (ii) one or more second nucleotides.

In some embodiments, each of the one or more second nucleotides comprises a second modified base from the second nucleoside triphosphate. The second modified base of the second nucleoside triphosphate can comprise a modified adenine, a modified guanine, a modified cytosine, a modified thymine, or a modified uracil. The first modified base of the first nucleoside triphosphate and the second modified base of the second nucleoside triphosphate can comprise modifications of a same unmodified base. The first modified base of the first nucleoside triphosphate and the second modified base of the second nucleoside triphosphate can comprise modification of different unmodified bases. In some embodiments, the second nucleoside triphosphate comprises the second modified base and a second accessory oligonucleotide covalently linked.

In some embodiments, each of the second nucleotides comprises a second unmodified base from the second nucleoside triphosphate. The second unmodified base of the second nucleoside triphosphate can comprise an adenine, a guanine, a cytosine, a thymine, or an uracil. The first modified base can comprise a modification of the second unmodified base.

In some embodiments, the first nucleoside triphosphate comprising the first modified base and the second nucleoside triphosphate are contacted with the first nucleic acid at a ratio that ranges from about 1:100 to about 100:1. The first nucleotide comprising the first modified base and the second nucleotide can be incorporated into the second nucleic acid at a ratio that ranges from about 1:100 to about 100:1.

In some embodiments, providing the first nucleic acid and the first nucleoside triphosphate comprising the first modified base comprises: providing the first nucleic acid, the first nucleoside triphosphate comprising the first modified base, and a plurality of second nucleoside triphosphates. Contacting the first nucleic acid and the first nucleoside triphosphate comprising the first modified base with the recombinant TdT can comprise: contacting the first nucleic acid, the first nucleoside triphosphate comprising the first modified base, and the plurality of second nucleoside triphosphates with the recombinant TdT for the first reaction time at the first temperature in the first reaction to generate the second nucleic acid. The second nucleic acid can comprise the first nucleic acid incorporated with one or more of the first nucleotides comprising the first modified base and one or more second nucleotides from the plurality of second nucleoside triphosphates.

In some embodiments, the plurality of second nucleoside triphosphates comprises a deoxyribose adenine triphosphate, a deoxyribose guanine triphosphate, a deoxyribose cytosine triphosphate, a deoxyribose thymine triphosphate, a deoxyribose uracil triphosphate, or a combination thereof. Two of the plurality of second nucleoside triphosphates can be contacted with the first nucleic acid at a ratio that ranges from about 1:100 to about 100:1. Two of the second nucleotides can be incorporated into the second nucleic acid at a ratio that ranges from about 1:100 to about 100:1. At least one, or each, of the plurality of second nucleoside triphosphates can comprise a second unmodified base. At least one, or each, of the plurality of second nucleoside triphosphates can comprise a second modified base.

In some embodiments, modified bases and unmodified bases of nucleotides can be incorporated into the second nucleic acid at a ratio that ranges from about 1:100 to about 100:1. The modified bases can comprise the first modified base and/or a base of at least one, or each, of the plurality of second nucleotides incorporated into the second nucleic acid. The unmodified bases can comprise the base of at least one, or each, of the plurality of second nucleotides incorporated into the second nucleic acid.

In some embodiments, at least 1% of the nucleotide bases of the second nucleic acid comprise modified bases. The modified bases can be distributed throughout the second nucleic acid. The modified bases can be distributed randomly throughout the second nucleic acid. The second nucleic acid can comprise a plurality of two or more consecutive modified bases. The plurality of consecutive modified bases can comprise three or more consecutive modified bases. In some embodiments, at least 1% of the nucleotide bases of the second nucleic acid comprise the first modified base.

In some embodiments, the first nucleic acid comprises a template capture site capable of binding a nucleic acid template. The template capture site can comprise a template capture sequence. The nucleic acid template can comprise a sequence that has at least 90% sequence identity to a reverse complement of the template capture sequence and is capable of hybridizing to the template capture sequence. The nucleic acid template can comprise a single stranded DNA.

In some embodiments, one or more of the first modified base of the first nucleoside triphosphate and the first nucleotide in the second nucleic acid comprise a functional moiety. The functional moiety of the first modified base can be capable of participating in a click chemistry reaction. The first modified base of the first nucleoside triphosphate and the first nucleotide in the second nucleic acid can comprise a saturated or unsaturated, substituted or unsubstituted, straight or branched aliphatic carbon chain. The functional moiety and the base of the first modified base can be on two ends of the first modified base connected by the saturated or unsaturated, substituted or unsubstituted, straight or branched aliphatic carbon chain.

In some embodiments, the method further comprises: providing a first accessory oligonucleotide. The method can comprise: contacting the second nucleic acid with the first accessory oligonucleotide for a second reaction time at a second temperature in a second reaction to generate a third nucleic acid comprising the second nucleic acid attached to one or more of the first accessory oligonucleotides.

In some embodiments, providing the first accessory oligonucleotide comprises: providing the first accessory oligonucleotide and a second accessory oligonucleotide. Contacting the second nucleic acid with the first accessory oligonucleotide can comprise: contacting the second nucleic acid with the first accessory oligonucleotide and the second accessory oligonucleotide for the second reaction time at the second temperature in the second reaction to generate the third nucleic acid comprising the second nucleic acid attached to one or more of the first accessory oligonucleotides and one or more of the second accessory oligonucleotides.

In some embodiments, the first accessory oligonucleotide comprises a first adapter sequence, or a reverse complement thereof. The second accessory oligonucleotide can comprise a second adapter sequence, or a reverse complement thereof. In some embodiments, the first adapter sequence comprises a P5 sequence. The second adapter sequence can comprise a P7 sequence.

In some embodiments, one or more of the first accessory oligonucleotide and the second accessory oligonucleotide is about 10 nucleotides to about 100 nucleotides in length. The third nucleic acid can comprise about 10 to about 1,000,000 of the first accessory oligonucleotides. The third nucleic acid can comprise about 10 to about 1,000,000 of the second accessory oligonucleotides. In some embodiments, the third nucleic acid comprises the second nucleic acid attached to one or more of the first accessory oligonucleotides. The third nucleic acid can comprise the second nucleic acid attached to one or more of the second accessory oligonucleotides.

In some embodiments, providing the first accessory oligonucleotide comprises providing a first accessory comprising the first accessory oligonucleotide and a first polymer. Contacting the second nucleic acid with the first accessory oligonucleotide can comprise contacting the second nucleic acid with the first accessory for the second reaction time at the second temperature in the second reaction to generate the third nucleic acid comprising the second nucleic acid attached to one or more of the first accessories. Providing the second accessory oligonucleotide can comprise providing a second accessory comprising the second accessory oligonucleotide and a second polymer. Contacting the second nucleic acid with the second accessory can comprise contacting the second nucleic acid and the second accessory for the second reaction time at the second temperature in the second reaction to generate the third nucleic acid comprising the second nucleic acid attached to one or more of the second accessories. The first accessory can comprise the first accessory oligonucleotide and the first polymer covalently linked. The second accessory can comprise the second accessory oligonucleotide and the second polymer covalently linked In some embodiments, the first accessory oligonucleotide or the first polymer comprises a first functional moiety. The second accessory oligonucleotide can comprise a second functional moiety. In some embodiments, the first functional moiety of the first accessory oligonucleotide or the first polymer and the second functional moiety of the second accessory oligonucleotide or the second polymer are identical. The first functional moiety of the first accessory oligonucleotide can be capable of reacting with the functional moiety of the first modified base of the first nucleotide to form a covalent linkage. The second functional moiety of the second accessory oligonucleotide or the second polymer can be capable of reacting with the functional moiety of the first modified base of the first nucleotide to form a covalent linkage.

In some embodiments, the first functional moiety of the first accessory oligonucleotide or the first polymer is capable of participating in a click chemistry reaction. The second functional moiety of the second accessory oligonucleotide or the second polymer can be capable of participating in a click chemistry reaction. In some embodiments, the first functional moiety of the first accessory oligonucleotide or the first polymer is capable of participating in a click chemistry reaction with the functional moiety of the first modified base of the first nucleotide. The second functional moiety of the second accessory oligonucleotide or the second polymer can be capable of participating in a click chemistry reaction with the functional moiety of the first modified base of the first nucleotide.

In some embodiments, one or more of the first functional moiety of the first accessory oligonucleotide or the first polymer, the second functional moiety of the second accessory oligonucleotide or the second polymer, the functional moiety of the first modified base of the first nucleoside triphosphate, and the functional moiety of the first nucleotide are independently an azide, an alkynyl, an alkenyl, a thiol, or a nitrone. The functional moiety of the first modified base of the first nucleotide and the first functional moiety of the first accessory oligonucleotide or the first polymer, or the functional moiety of the first modified base of the first nucleotide and the second functional moiety of the second accessory oligonucleotide or the second polymer, or both, can be selected from the following pairs: (i) azido/alkynyl; (ii) alkynyl/azido; (iii) thiol/alkynyl; (iv) alkynyl/thiol; (v) alkenyl/thiol; (vi) thiol/alkenyl; (vii) azido/cyclooctynyl; (viii) cyclooctynyl/azido; (ix) nitrone/cyclooctynyl; and (x) cyclooctynyl/nitrone. The functional moiety of the first modified base of the first nucleotide can be an azido. One or more of the first functional moiety of the first accessory oligonucleotide or the first polymer and the second functional moiety of the second accessory oligonucleotide or the second polymer can be independently an alkynyl.

In some embodiments, the click chemistry reaction comprises copper catalyzed azide-alkyne cycloaddition (CuAAC). The covalent linkage can comprise a triazolyl. The CuAAC can comprise a Cu(I) stabilizing ligand. The Cu(I) stabilizing ligand can be selected from the group consisting of: 3-[4-({bis[(1-tert-butyl-1H-1,2,3-triazol-4-yl)methyl]amino}methyl)-1H-1,2,3-triazol-1-yl]propanol (BTTP), 3-[4-({bis[(1-tert-butyl-1H-1,2,3-triazol-4-yl)methyl]amino}methyl)-1H-1,2,3-triazol-1-yl]propyl hydrogen sulfate (BTTPS), 2-[4-({bis[(1-tert-butyl-1H-1,2,3-triazol-4-yl)methyl]amino}methyl)-1H-1,2,3-triazol-1-yl] ethyl hydrogen sulfate (BTTES), 2-[4-{(bis[(1-tert-butyl-1H-1,2,3-triazol-4-yl)methyl]amino)methyl}-1H-1,2,3-triazol-1-yl]-acetic acid (BTTAA), bathophenanthroline disulfonate disodium salt (BPS), N,N,N',N'',N''-Pentamethyldiethylenetriamine (PMDETA), tris-((1-benzyl-1H-1,2,3-triazol-4-yl)methyl)amine (TBTA), Tris(3-hydroxypropyl-triazolylmethyl)amine (THPTA), $N^\varepsilon$-((1R,2R)-2- azidocyclopentyloxy)carbonyl)-L-lysine (ACPK), and 4-N,N-dimethyl amino-1,8-naphthalimide (4-DMN).

In some embodiments, the click chemistry reaction comprises strain-promoted azide-alkyne cycloaddition (SPAAC). The covalent linkage can comprise a cyclooctatriazolyl. In some embodiments, the click chemistry reaction comprises alkyne hydrothiolation. The covalent linkage can comprise an alkenyl sulfide. In some embodiments, the click chemistry reaction comprises alkene hydrothiolation. The covalent linkage can comprise an alkyl sulfide. In some embodiments, the click chemistry reaction comprises strain-promoted alkyne-nitrone cycloaddition (SPANC). The covalent linkage can comprise an octahydrocyclooocta-isoxazolyl. The cyclooctynyl can be dibenzylcyclooctyne (DBCO) or a derivative thereof. In some embodiments, the click chemistry reaction is biocompatible.

In some embodiments, the second temperature is about 20° C. to about 65° C. The second temperature can be less than 0° C. The second temperature can be about –4° C. to about –20° C. In some embodiments, the second reaction time is at least 1 second.

In some embodiments, the method further comprises: (c) providing the nucleic acid template comprising the first adapter sequence, or a reverse complement thereof, the second adapter sequence, or a reverse complement thereof, and a nucleic acid hybridization sequence capable of hybridizing to the template capture site on the third nucleic acid. The method can comprise: (d) contacting the third nucleic acid with the nucleic acid template to generate the third nucleic acid with the nucleic acid template hybridized to the template capture site on the third nucleic acid via the nucleic acid hybridization sequence of the nucleic acid template. The method can comprise: (e) performing amplification on the third nucleic acid hybridized with the nucleic acid template to generate a fourth nucleic acid comprising the third nucleic acid attached to one or more of the first accessory oligonucleotides and one or more of the second accessory oligonucleotides extended to comprise a sequence of the nucleic acid template, or a reverse complement thereof. The amplification can be, for example, bridge amplification or exclusion amplification. The method can comprise: (f) determining the sequence of the nucleic acid template using the fourth nucleic acid. The nucleic acid hybridization sequence of the nucleic acid template can comprise a reverse complement of the template capture site.

In some embodiments, the first nucleic acid, the second nucleic acid, the third nucleic acid, and/or the fourth nucleic acid comprise a third polymer.

In some embodiments, the amino acid substitution mutation at the position functionally equivalent to Glu191 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu191 can comprise a mutation to a nonpolar amino acid, a hydrophobic amino acid, an aliphatic amino acid, or a branched-chain amino acid. The amino acid substitution mutation at the position functionally equivalent to Glu191 in the *Bos taurus* TdT of SEQ ID NO: 12 can be Glu191Ala, Glu191Arg, Glu191Asn, Glu191Asp, Glu191Cys, Glu191Gln, Glu191Gly, Glu191His, Glu191Ile, Glu191Leu, Glu191Lys, Glu191Met, Glu191Phe, Glu191Pro, Glu191Ser, Glu191Thr, Glu191Trp, Glu191Tyr, or Glu191Val. The amino acid substitution mutation at the position functionally equivalent to Glu191 in the *Bos taurus* TdT of SEQ ID NO: 12 can be Glu191Ala, Glu191Gly, Glu191Ile, Glu191Leu, Glu191Met, or Glu191Val. The amino acid substitution mutation at the position functionally equivalent to Glu191 in the *Bos taurus* TdT of SEQ ID NO: 12 can be Glu191Val.

In some embodiments, the amino acid substitution mutation at the position functionally equivalent to Lys193 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys193 in the *Bos taurus* TdT of SEQ ID NO: 12 can comprise a mutation to a polar amino acid or a hydrophilic amino acid. The amino acid substitution mutation at the position functionally equivalent to Lys193 in the *Bos taurus* TdT of SEQ ID NO: 12 can be Lys193Ala, Lys193Arg, Lys193Asn, Lys193Asp, Lys193Cys, Lys193Gln, Lys193Glu, Lys193Gly, Lys193His, Lys193Ile, Lys193Leu, Lys193Met, Lys193Phe, Lys193Pro, Lys193Ser, Lys193Thr, Lys193Trp, Lys193Tyr, or Lys193Val. The amino acid substitution mutation at the position functionally equivalent to Lys193 in the *Bos taurus* TdT of SEQ ID NO: 12 can be Lys193Asn, Lys193Gln, Lys193Ser, or Lys193Thr. The amino acid substitution mutation at the position functionally equivalent to Lys193 in the *Bos taurus* TdT of SEQ ID NO: 12 can be Lys193Asn.

In some embodiments, the amino acid substitution mutation at the position functionally equivalent to Glu194 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu194 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Glu194 in the *Bos taurus* TdT of SEQ ID NO: 12 can be Glu194Ala, Glu194Arg, Glu194Asn, Glu194Asp, Glu194Cys, Glu194Gln, Glu194Gly, Glu194His, Glu194Ile, Glu194Leu, Glu194Lys, Glu194Met, Glu194Phe, Glu194Pro, Glu194Ser, Glu194Thr, Glu194Trp, Glu194Tyr, or Glu194Val. The amino acid substitution mutation at the position functionally equivalent to Glu194 in the *Bos taurus* TdT of SEQ ID NO: 12 can be Glu194Ala, Glu194Gly, Glu194Ile, Glu194Leu, Glu194Met, or Glu194Val. The amino acid substitution mutation at the position functionally equivalent to Glu194 in the *Bos taurus* TdT of SEQ ID NO: 12 can be Glu194Gly.

In some embodiments, the amino acid substitution mutation at the position functionally equivalent to Asp242 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Asp242 in the *Bos taurus* TdT of SEQ ID NO: 12 can comprise a mutation to a polar amino acid or an aromatic amino acid. The amino acid substitution mutation at the position functionally equivalent to Asp242 in the *Bos taurus* TdT of SEQ ID NO: 12 can be Asp242Ala, Asp242Arg, Asp242Asn, Asp242Cys, Asp242Gln, Asp242Glu, Asp242Gly, Asp242His, Asp242Ile, Asp242Leu, Asp242Lys, Asp242Met, Asp242Phe, Asp242Pro, Asp242Ser, Asp242Thr, Asp242Trp, Asp242Tyr, or Asp242Val. The amino acid substitution mutation at the position functionally equivalent to Asp242 in the *Bos taurus* TdT of SEQ ID NO: 12 can be Asp242Asn, Asp242Gln, Asp242Phe, Asp242Ser, Asp242Thr, Asp242Trp, or Asp242Tyr. The amino acid substitution mutation at the position functionally equivalent to Asp242 in the *Bos taurus* TdT of SEQ ID NO: 12 can be Asp242Tyr.

In some embodiments, the amino acid substitution mutation at the position functionally equivalent to Lys287 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys287 in the *Bos taurus* TdT of SEQ ID NO: 12 can comprise a mutation to a polar amino acid, a negatively charged amino acid or a hydrophilic amino acid. The amino acid substitution mutation at the position functionally equivalent to Lys287 in the *Bos taurus* TdT of SEQ ID NO: 12 can be Lys287Ala, Lys287Arg, Lys287Asn, Lys287Asp, Lys287Cys, Lys287Gln, Lys287Glu, Lys287Gly, Lys287His, Lys287Ile, Lys287Leu, Lys287Met, Lys287Phe, Lys287Pro, Lys287Ser, Lys287Thr, Lys287Trp, Lys287Tyr, or Lys287Val. The amino acid substitution mutation at the position functionally equivalent to Lys287 in the *Bos taurus* TdT of SEQ ID NO: 12 can be Lys287Asp or Lys287Glu. The amino acid substitution mutation at the position functionally equivalent to Lys287 in the *Bos taurus* TdT of SEQ ID NO: 12 can be Lys287Glu.

In some embodiments, the amino acid substitution mutation at the position functionally equivalent to Phe296 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Phe296 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Phe296 in the *Bos taurus* TdT of SEQ ID NO: 12 can be Phe296Ala, Phe296Arg, Phe296Asn, Phe296Asp, Phe296Cys, Phe296Gln, Phe296Glu, Phe296Gly, Phe296His, Phe296Ile, Phe296Leu, Phe296Lys, Phe296Met, Phe296Pro, Phe296Ser, Phe296Thr, Phe296Trp, Phe296Tyr, or Phe296Val. The amino acid substitution mutation at the position functionally equivalent to Phe296 in the *Bos taurus* TdT of SEQ ID NO: 12 can be Phe296Ala, Phe296Gly, Phe296Ile, Phe296Leu, Phe296Met, or Phe296Val. The amino acid substitution mutation at the position functionally equivalent to Phe296 in the *Bos taurus* TdT of SEQ ID NO: 12 can be Phe296Leu.

In some embodiments, the amino acid substitution mutation at the position functionally equivalent to Met299 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Met299 in the *Bos taurus* TdT of SEQ ID NO: 12 can comprise a mutation to a polar amino acid, a positively charged amino acid, or a hydrophilic amino acid. The amino acid substitution mutation at the position functionally equivalent to Met299 in the *Bos taurus* TdT of SEQ ID NO: 12 can be Met299Ala, Met299Arg, Met299Asn, Met299Asp, Met299Cys, Met299Gln, Met299Glu, Met299Gly, Met299His, Met299Ile, Met299Leu, Met299Lys, Met299Phe, Met299Pro, Met299Ser, Met299Thr, Met299Trp, Met299Tyr, or Met299Val. The amino acid substitution mutation at the position functionally equivalent to Met299 in the *Bos taurus* TdT of SEQ ID NO: 12 can be Met299Arg, Met299His, or Met299Lys. The amino acid substitution mutation at the position functionally equivalent to Met299 in the *Bos taurus* TdT of SEQ ID NO: 12 can be Met299Lys.

In some embodiments, the amino acid substitution mutation at the position functionally equivalent to Thr342 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Thr342 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to Thr342 in the *Bos taurus* TdT of SEQ ID NO: 12 can be Thr342Ala, Thr342Arg, Thr342Asn, Thr342Asp, Thr342Cys, Thr342Gln, Thr342Glu, Thr342Gly, Thr342His, Thr342Ile, Thr342Leu, Thr342Lys, Thr342Met, Thr342Phe, Thr342Pro, Thr342Ser, Thr342Trp, Thr342Tyr, or Thr342Val. The amino acid substitution mutation at the position functionally equivalent to Thr342 in the *Bos taurus* TdT of SEQ ID NO: 12 can be Thr342Asn, Thr342Cys, Thr342Gln, Thr342Pro, or Thr342Ser. The amino acid substitution mutation at the position functionally equivalent to Thr342 in the *Bos taurus* TdT of SEQ ID NO: 12 can be Thr342Ser.

In some embodiments, the amino acid substitution mutation at the position functionally equivalent to His421 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to His421 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to His421 in the *Bos taurus* TdT of SEQ ID NO: 12 can be His421Ala, His421Arg, His421Asn, His421Asp, His421Cys, His421Gln, His421Glu, His421Gly, His421Ile, His421Leu, His421Lys, His421Met, His421Phe, His421Pro, His421Ser, His421Thr, His421Trp, His421Tyr, or His421Val. The amino acid substitution mutation at the position functionally equivalent to His421 in the *Bos taurus* TdT of SEQ ID NO: 12 can be His421Asn, His421Cys, His421Gln, His421Pro, His421Ser, or His421Thr. The amino acid substitution mutation at the position functionally equivalent to His421 in the *Bos taurus* TdT of SEQ ID NO: 12 can be His421Pro.

In some embodiments, the recombinant TdT comprises two or more amino acid substitution mutations at two or more positions functionally equivalent to Glu191, Lys193, Glu194, Asp242, Lys287, Phe296, Met299, Thr342, and His421 in the *Bos taurus* TdT of SEQ ID NO: 12. The two or more amino acid substitution mutations at the two or more positions functionally equivalent to Glu191, Lys193, Glu194, Asp242, Lys287, Phe296, Met299, Thr342, and His421 in the *Bos taurus* TdT of SEQ ID NO: 12 can comprise two or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises three or more amino acid substitution mutations at three or more positions functionally equivalent to Glu191, Lys193, Glu194, Asp242, Lys287, Phe296, Met299, Thr342, and His421 in the *Bos taurus* TdT of SEQ ID NO: 12. The three or more amino acid substitution mutations at the three or more positions functionally equivalent to Glu191, Lys193, Glu194, Asp242, Lys287, Phe296, Met299, Thr342, and His421 in the *Bos taurus* TdT of SEQ ID NO: 12 can comprise three or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises four or more amino acid substitution mutations at four or more positions functionally equivalent to Glu191, Lys193, Glu194, Asp242, Lys287, Phe296, Met299, Thr342, and His421 in the *Bos taurus* TdT of SEQ ID NO: 12. The four or more amino acid substitution mutations at the four or more positions functionally equivalent to Glu191, Lys193, Glu194, Asp242, Lys287, Phe296, Met299, Thr342, and His421 in the *Bos taurus* TdT of SEQ ID NO: 12 can comprise four or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises five or more amino acid substitution mutations at five or more positions functionally equivalent to Glu191, Lys193, Glu194, Asp242, Lys287, Phe296, Met299, Thr342, and His421 in the *Bos taurus* TdT of SEQ ID NO: 12. The five or more amino acid substitution mutations at the five or more positions functionally equivalent to Glu191, Lys193, Glu194, Asp242, Lys287, Phe296, Met299, Thr342, and His421 in the *Bos taurus* TdT of SEQ ID NO: 12 can comprise five or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises six or more amino acid substitution mutations at six or more positions functionally equivalent to Glu191, Lys193, Glu194, Asp242, Lys287, Phe296, Met299, Thr342, and His421 in the *Bos taurus* TdT of SEQ ID NO: 12. The six or more amino acid substitution mutations at the six or more positions functionally equivalent to Glu191, Lys193, Glu194, Asp242, Lys287, Phe296, Met299, Thr342, and His421 in the *Bos taurus* TdT of SEQ ID NO: 12 can comprise six or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises seven or more amino acid substitution mutations at seven or more positions functionally equivalent to Glu191, Lys193, Glu194, Asp242, Lys287, Phe296, Met299, Thr342, and His421 in the *Bos taurus* TdT of SEQ ID NO: 12. The seven or more amino acid substitution mutations at the seven or more positions functionally equivalent to Glu191, Lys193, Glu194, Asp242, Lys287, Phe296, Met299, Thr342, and His421 in the *Bos taurus* TdT of SEQ ID NO: 12 can comprise seven or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight or more amino acid substitution mutations at eight or more positions functionally equivalent to Glu191, Lys193, Glu194, Asp242, Lys287, Phe296, Met299, Thr342, and His421 in the *Bos taurus* TdT of SEQ ID NO: 12. The eight or more amino acid substitution mutations at the eight or more positions functionally equivalent to Glu191, Lys193, Glu194, Asp242, Lys287, Phe296, Met299, Thr342, and His421 in the *Bos taurus* TdT of SEQ ID NO: 12 can comprise eight or more of Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight amino acid substitution mutations at eight positions functionally equivalent to Lys193, Glu194, Asp242, Lys287, Phe296, Met299, Thr342, and His421 in the *Bos taurus* TdT of SEQ ID NO: 12. The eight amino acid substitution mutations at the eight positions functionally equivalent to Lys193, Glu194, Asp242, Lys287, Phe296, Met299, Thr342, and His421 in the *Bos taurus* TdT of SEQ ID NO: 12 can be Lys193Asn, Glu194Gly, Asp242Tyr, Lys287Glu, Phe296Leu, Met299Lys, Thr342Ser, and His421Pro, respectively.

In some embodiments, the recombinant TdT comprises nine amino acid substitution mutations at positions functionally equivalent to Glu191, Lys193, Glu194, Asp242, Lys287, Phe296, Met299, Thr342, and His421 in the *Bos taurus* TdT of SEQ ID NO: 12. The nine amino acid substitution mutations at the positions functionally equivalent to Glu191, Lys193, Glu194, Asp242, Lys287, Phe296, Met299, Thr342, and His421 in the *Bos taurus* TdT of SEQ ID NO: 12 can be Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises an amino acid sequence that is at least 85% identical to SEQ ID NO: 1. The recombinant TdT comprises an amino acid sequence that can be at least 90% identical to SEQ ID NO: 1. The recombinant TdT comprises an amino acid sequence that can be at least 95% identical to SEQ ID NO: 1. The recombinant TdT comprises an amino acid sequence that can be at least 95% identical to SEQ ID NO: 11. The recombinant TdT comprises an amino acid sequence that can be at least 80% identical to SEQ ID NO: 12.

In some embodiments, the recombinant TdT is stable at a temperature of 47° C. or higher. The recombinant TdT can be stable at a temperature of 50° C. or higher. The recombinant TdT can be stable at a temperature of 55° C. or higher. The recombinant TdT can be stable at a temperature of 58° C. or higher. In some embodiments, the terminal deoxynucleotidyl transferase activity of the recombinant TdT is at least 80%, 85%, 90%, 95%, 100%, 105%, 110%, 115%, or 120%, of the terminal deoxynucleotidyl transferase activity of the *Bos taurus* TdT of SEQ ID NO: 12 at a same test temperature. The test temperature can be 37° C., 47° C., 50° C., 55° C., or 58° C.

In some embodiments, the recombinant TdT comprises a small ubiquitin-like modifier (SUMO) fragment. The SUMO fragment comprises an amino acid sequence that can be at least 80% identical to SEQ ID NO: 13. The recombinant TdT can comprise the SUMO fragment on the N-terminus of the recombinant TdT. The recombinant TdT can comprise an amino acid sequence that is at least 80% identical to SEQ ID NO: 14. The recombinant TdT can comprise an amino acid sequence that is at least 80% identical to SEQ ID NO: 15. The recombinant TdT can comprise the SUMO fragment on the C-terminus of the recombinant TdT.

Disclosed herein include embodiments of a second nucleic acid obtained by any method of modifying a nucleic acid of the present disclosure. Disclosed herein include embodiments of a third nucleic acid obtained by any method of modifying a nucleic acid of the present disclosure. Disclosed herein include embodiments of a fourth nucleic acid obtained by any method of modifying a nucleic acid of the present disclosure.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 1 is a schematic illustration showing non-limiting exemplary processes of generating a single-stranded DNA scaffold, a carrier, and a nanoparticle.

FIG. 2 shows a non-limiting exemplary sequence alignment of SUMO-TdT (SEQ ID NO: 14) with amino acids 139-520 (SEQ ID NO: 1) of Bos taurus TdT (SEQ ID NO: 12). SUMO-TdT refers to a recombinant TdT that contains amino acids 139-520 of Bos taurus TdT at amino acid positions 123-504 and an N-terminal SUMO-tag (SEQ ID NO: 13) at amino acid positions 22-119. The nine amino acids highlighted are substitution mutations in SUMO-TdT identified herein. The amino acid positions of the substitution mutations in SUMO-TdT (and variants thereof) and corresponding positions in Bos taurus TdT are shown.

FIGS. 5A-5C are non-limiting exemplary gel graphs showings the results of TdT extension with azide-PEG4-dUTP or azide-hexyl-dATP by TdT3-2 and a commercial NEB TdT for one minute and 60 minutes.

DETAILED DESCRIPTION

Figure 3:
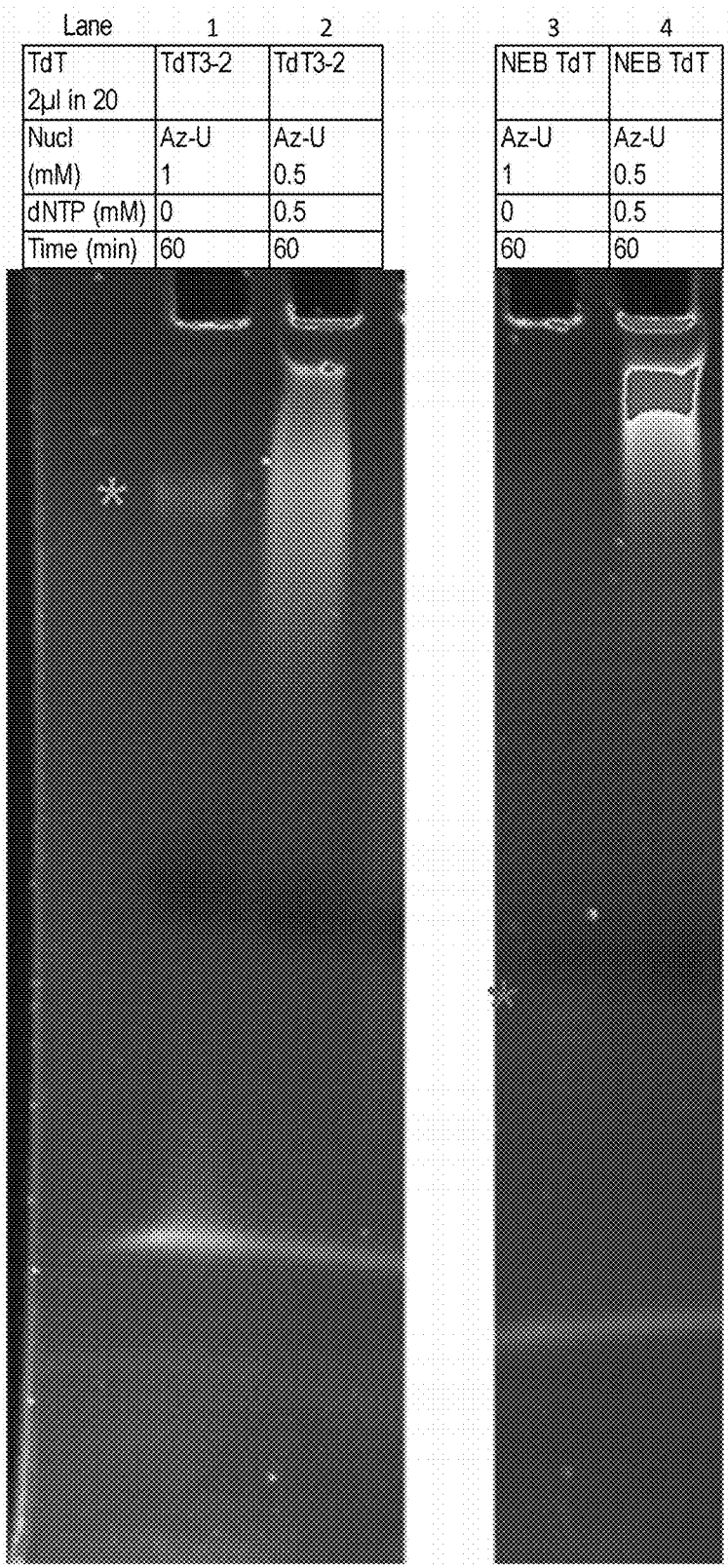
FIG. 3 is a non-limiting exemplary gel graph showing the terminal deoxynucleotidyl transferase activity of a commercial TdT from NEB and TdT3-2.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Many sequencing platforms use "sequencing-by-synthesis" (SBS) technology and fluorescence-based methods for detection. For example, a library of template polynucleotides can be attached to a surface of a substrate in a process known as seeding to generate seeded template polynucleotides. Multiple copies of each seeded template polynucleotide, called clustered polynucleotides, can then be synthesized in attachment to the surface in proximity to where the template polynucleotide has been seeded, in a process called clustering. Subsequently, nascent copies of the clustered polynucleotides can be synthesized by incorporating nucleotides with, for example, fluorescent labels. The nucleotides incorporated into the nascent copies of the clustered polynucleotides can emit signals (e.g., fluorescent signals) that identify each nucleotide incorporated. Clustering of copies of the seeded template polynucleotide in proximity to where the template polynucleotide has been initially seeded results in amplification of signal, thus improving detection.

Seeding and clustering work well when template polynucleotides that differ from each other seed on, or attach to, positions of the surface sufficiently distal from each other such that clustering results in spatially distinct clusters of copied polynucleotides each resulting from the seeding of a single template polynucleotide, a condition referred to as monoclonality. For example, a library of template polynucleotides can include a high number of template polynucleotides with different nucleotide sequences. If two such template polynucleotides seed too closely together on a surface of a substrate, clustering may result in spatially comingled populations of clustered polynucleotides, some of which may have a sequence of one of the template polynucleotides that seeded nearby, and others may have a sequence of another template polynucleotide that also seeded nearby on the surface. Or, two clusters formed from two different template polynucleotides that seeded in too close proximity to each other may be too adjacent to each other or adjoin each other such that an imaging system used in an SBS process may be unable to distinguish the signals generated by incorporated nucleotides as separate clusters even though there may be no or minimal spatial comingling of substrate-attached clustered polynucleotides between the clusters. Such a disadvantageous condition can be referred to as polyclonality. It may be more difficult, time consuming, expensive, and less efficient, and require more complicated data analytics to obtain unambiguous sequence information from a polyclonal cluster if present.

Monoclonality can also be achieved by distributing single nanoparticles each with copied polynucleotides from a template polynucleotide to single wells of a substrate (e.g., a flow cell). A scaffold (e.g., a single stranded DNA (ssDNA) scaffold) can serve as a "carrier" for multiple copies of a template polynucleotide. The carrier with multiple copies of the template molecule can be a nanoparticle capable of occupying a single well on a substrate by excluding other macromolecules from occupying the same well by steric clashes or hinderance. Single nanoparticles occupying single wells of the substrate can result in monoclonality, or close to monoclonality.

Disclosed herein include embodiments of a method of generating a scaffold. In some embodiments, the method comprises: (a) providing a single stranded deoxyribonucleic acid (ssDNA) and a nucleoside triphosphate comprising a modified base. The method can comprise: (b) contacting the ssDNA and the nucleoside triphosphate comprising the modified base with a recombinant terminal deoxynucleotidyl transferase (TdT) to generate a ssDNA scaffold. The ssDNA scaffold can comprise the ssDNA incorporated with one or more nucleotides comprising the modified base from the nucleoside triphosphate. The recombinant TdT can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the Bos taurus TdT of SEQ ID NO: 12. The method can comprises: (c) contacting the ssDNA scaffold with a first adapter oligonucleotide and a second adapter oligonucleotide to generate a nucleic acid carrier. The first adapter oligonucleotide can comprise a first adapter sequence. The second adapter oligonucleotide can comprise a second adapter sequence. The nucleic acid carrier can comprise the ssDNA scaffold attached to the first adapter oligonucleotide and the second adapter oligonucleotide. The method can be used to generate a nanoparticle from the carrier. For example, the method can comprise: (d) providing a nucleic acid template comprising the first adapter sequence, or a reverse complement thereof, the second adapter sequence, or a reverse complement thereof, and a nucleic acid hybridization sequence. The method can comprise: (e) contacting the nucleic acid carrier with the nucleic acid template to generate the nucleic acid carrier having the nucleic acid template hybridized to a template capture site of the nucleic acid carrier via the nucleic acid hybridization sequence of the nucleic acid template. The method can comprise: (f) performing amplification on the nucleic acid carrier hybridized with the nucleic acid template to generate a plurality of amplified nucleic acids each comprising the first adapter oligonucleotides and the second adapter oligonucleotides extended to comprise a sequence of the nucleic acid template, or a reverse complement thereof. The amplification can be, for example, bridge amplification or exclusion amplification. The carrier with the plurality of amplified nucleic acids is referred to herein as a nanoparticle. The method can comprise: (g) determining the sequence of the nucleic acid template using the plurality of amplified nucleic acids. A nanoparticle with a sufficient spatial dimension can be capable of occupying a single well on a substrate (e.g., a flow cell) by excluding other nanoparticles from occupying the same well by steric clashes or hinderance, therefore resulting in monoclonality or close to monoclonality.

Disclosed herein include embodiments of a method of modifying a nucleic acid. In some embodiments, the method comprises: (a) providing a first nucleic acid and a first nucleoside triphosphate comprising a first modified base. The method can comprise: (b) contacting the first nucleic acid and the first nucleoside triphosphate comprising the first modified base with a recombinant terminal deoxynucleotidyl transferase (TdT) for a first reaction time at a first temperature in a first reaction to generate a second nucleic acid. The second nucleic acid can comprise the first nucleic acid incorporated with one or more first nucleotides comprising the first modified base from the first nucleoside triphosphate. The recombinant TdT can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the Bos taurus TdT of SEQ ID NO: 12.

Generating Single Stranded DNA Molecules Incorporating Multiple Modified Bases

A scaffold (e.g., a single stranded DNA (ssDNA) scaffold) that incorporates modified nucleotides can be generated. The scaffold can serve as a "carrier" for multiple copies of a template molecule. The carrier with multiple copies of the template molecule can be a nanoparticle capable of occupying a single well (e.g., a microwell) on a substrate (e.g., a flow cell comprising multiple wells, such as 100, 1,000, 10,000 or more wells) by excluding other macromolecules from occupying the same well by steric clashes or hinderance. Single wells on a substrate each with one nanoparticle can result in monoclonality, or close in monoclonality. Alternatively, the ssDNA scaffold can carry a single copy of the template. The scaffold can have multiple copies of a reverse complement of an anchoring oligo or reverse complements of anchoring oligos. The scaffold can bind and sequester all the "anchoring" oligos in a given well because of the presence of the multiple copies of the reverse complement of the anchoring oligo or reverse complements of the anchoring oligos, thus enabling a single template to be captured per well.

One way to generate or construct such a ssDNA scaffold is using a ssDNA polymerase such as Terminal deoxynucleotidyl Transferase (TdT) to randomly incorporate nucleotides carrying modifications, such as azide groups on the bases, into a primer strand. However, commercially available TdTs do not readily incorporate multiple serial base modified nucleotides, presumably due to steric clashes.

Embodiments of recombinant TdTs disclosed herein are thermostable and are better (e.g., much better) than commercially available TdTs, such as TdT from New England Biolabs®, Inc. (NEB; Ipswich, MA), at incorporating base modified nucleotides, such as a nucleotide with a PEG chain conjugated to the base (referred to herein as a PEG-nucleotide). For example, NEB TdT would stop after incorporating 1-2 PEG-nucleotides, and the recombinant TdT can incorporate multiple PEG-nucleotides in series.

Any recombinant TdT disclosed herein therefore can be an excellent catalyst for the generation of ssDNA carrying various types of base modified nucleotides for different purposes, including generation of the "carrier" for monoclonal clustering.

FIG. 1 is a schematic illustration showing non-limiting exemplary processes of generating a single-stranded DNA scaffold, a carrier, and a nanoparticle. A single stranded DNA (ssDNA) scaffold 120s can be synthesized by use of a terminal deoxynucleotidyl transferase 112 (TdT). TdT 112 can incorporate deoxynucleotides 108nt_m, 108nt_u at the 3' hydroxyl terminus of a single-stranded DNA strand 104, without requiring or copying a template. The size of a ssDNA scaffold 120s synthesized by use of a TdT 112 can be controlled by modifying a duration of a polymerization process during which the scaffold 120s is synthesized.

The DNA scaffold 120s can be synthesized in the presence of nucleoside triphosphates 108nst_m with modified bases and nucleoside triphosphates 108nst_u with unmodified bases. Depending on the relative concentrations of nucleoside triphosphates 108nst_m with modified bases and nucleoside triphosphates 108nst_u with unmodified bases, a certain percentage of nucleotides 108nt_m, 108nt_u incorporated into the DNA scaffold 120s are nucleotides 108nt_m with modified bases. One or more types of nucleoside triphosphates 108nt_m with modified bases can be present when synthesizing the DNA scaffold 120s, and one or more types of nucleotides 120nt_m with modified bases can be incorporated into the DNA scaffold 120s.

In this non-limiting example, accessory oligonucleotides 124as1, 124as2 are shown binding to the ssDNA scaffold for form a nucleic acid carrier 120c. The accessory oligonucleotides 124as1, 124as2 can interact with functional moieties 108fm of the modified bases of the nucleotides 108nt_m in a click chemistry reaction. For example, the functional moieties 108fm of the modified bases of the nucleotides 108nt_m incorporated into the scaffold 120s can react with the functional moieties 124fm1, 124fm2 on the accessory oligonucleotides 124ao1, 124ao2.

A single template capture site 104tcs is present on an end (e.g., 5' end) of the ssDNA scaffold 120s. Four-pointed stars denote functional moieties 108fm of modified bases of nucleotides 108nt_m on the scaffold 120s. An accessory oligonucleotide 124ao1, 124ao2 can comprise a P5 sequence, or a reverse complement thereof, or a P7 sequence, or a reverse complement thereof. Five-pointed stars on the accessory oligonucleotides 124ao1, 124ao2 denote functional moieties 124fm1, 124m2 that can interact with the functional moieties 108fm of the modified bases of the nucleotides 108nt_m in the scaffold 120s.

The 5' end of a template nucleic acid or polynucleotide 128 is then shown binding to the single template capture site 104tcs at the complementary 5' end of the nucleic acid carrier 120c by non-covalent Watson-Crick base pairing hybridization. A clustering process is then performed on the nucleic acid carrier 120c. The portion of the template nucleic acid 128 not hybridized to the nucleic acid carrier 120c can contain sequences that can hybridize to the P5 sequence, or a reverse complement thereof, and the P7 sequence, or a reverse complement thereof. For example, the template nucleic acid 128 can contain the P5 sequence, or a reverse complement thereof, and the P7 sequence, or a reverse complement thereof. Following multiple rounds of polymerization, carrier-bound copies and/or reverse complements of the template polynucleotide 128, other than the 5' end of the template nucleic acid 128 that is capable of hybridizing to the template capture site 104tcs, are synthesized by extending from the 3' ends of the P5 and P7 accessory oligonucleotides.

Modifying Nucleic Acids

Disclosed herein include methods of generating a scaffold, generating a carrier, generating a nanoparticle, and sequencing a nucleic acid template. Referring to FIG. 1, the method can comprise providing a single stranded deoxyribonucleic acid (ssDNA) 104 and a nucleoside triphosphate 108nst_m comprising a modified base. The method can comprise contacting the ssDNA 104 and the nucleoside triphosphate 108nst_m comprising the modified base with a recombinant terminal deoxynucleotidyl transferase (TdT) 112 at action 116a to generate a ssDNA scaffold 120s. The ssDNA scaffold 120s can comprise the ssDNA 104 incorporated with one or more nucleotides 108nt_m comprising the modified base from the nucleoside triphosphate 108nst_m. The recombinant TdT 108 can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the *Bos taurus* TdT of SEQ ID NO: 12.

The method can comprise contacting the ssDNA scaffold 120s with a first adapter oligonucleotide 124ao1 (e.g., an oligonucleotide comprising a P5 sequence), or a first adapter comprising the first adapter oligonucleotide 124ao1, and a second adapter oligonucleotide 124ao2 (e.g., an oligonucleotide comprising a P7 sequence), or a second adapter comprising the second adapter oligonucleotide 124ao2, at action 116b to generate a nucleic acid carrier 120c. The first adapter oligonucleotide 124ao1 can comprise a first adapter sequence 124as1 (e.g., a P5 sequence), or a reverse complement thereof. The second adapter oligonucleotide 124ao2 can comprise a second adapter sequence 124as (e.g., a P7 sequence), or a reverse complement thereof, or a reverse complement thereof. The nucleic acid carrier 120c can comprise the ssDNA scaffold 120s attached to the first adapter oligonucleotide 124ao1 and the second adapter oligonucleotide 124ao2.

In some embodiments, contacting the ssDNA scaffold 120s with the first adapter oligonucleotide 124ao1 comprises contacting the ssDNA scaffold with a first adapter comprising the first adapter oligonucleotide 124ao1 and a first polymer. Contacting the ssDNA scaffold 120s with the second adapter oligonucleotide 124ao2 can comprise contacting the ssDNA scaffold with a second adapter comprising the second adapter oligonucleotide 124ao2 and a second polymer. The first adapter can comprise the first adapter oligonucleotide 124ao1 and the first polymer covalently linked. The second adapter can comprise the second adapter oligonucleotide 124ao2 and the second polymer covalently linked. The ssDNA scaffold 120s can comprise a third polymer.

The method can comprise providing a nucleic acid template 128 comprising the first adapter sequence 124as1, or a reverse complement thereof, the second adapter sequence 124as2, or a reverse complement thereof, and a nucleic acid hybridization sequence 128tcs capable of hybridizing to the template capture site 104tcs. The method can comprise contacting the nucleic acid carrier 120c with the nucleic acid template at action 116c to generate the nucleic acid carrier 120c having the nucleic acid template 128 hybridized to a template capture site 104tcs of the nucleic acid carrier 120c via the nucleic acid hybridization sequence 128tcs of the nucleic acid template 128. The template capture site 104tcs can hybridize to the nucleic acid hybridization sequence 128tcs of the nucleic acid template 128. The template capture site 104tcs and the nucleic acid hybridization sequence 128tcs of the nucleic acid template 128 can be reverse complements. The template capture site 104tcs and the reverse complement of the nucleic acid hybridization sequence 128tcs of the nucleic acid template 128 can be identical, or substantially identical (e.g., 75%, 80%, 85%, 90%, 95%, 99% identical). The method can comprise performing amplification (e.g., bridge amplification or exclusion amplification) at action 116d on the nucleic acid carrier 120c hybridized with the nucleic acid template 128 to generate a plurality of amplified nucleic acids 132 each comprising the first adapter oligonucleotide 124ao1 or the second adapter oligonucleotide 124ao2 extended to comprise a sequence of the nucleic acid template 128, or a reverse complement thereof. The carrier with the plurality of amplified nucleic acids is referred to herein as a nanoparticle 120n The method can comprise determining the sequence of the nucleic acid template 128 using one or more the plurality of amplified nucleic acids 132.

Disclosed herein include methods of modifying a nucleic acid. Referring to FIG. 1, the method can comprise providing a first nucleic acid 104 (e.g., a single stranded deoxyribonucleic acid) and a first nucleoside triphosphate 108nst_m comprising a first modified base. The method can comprise contacting the first nucleic acid 104 and the first nucleoside triphosphate 108nst_m comprising the first modified base with a recombinant terminal deoxynucleotidyl transferase (TdT) 112 for a first reaction time at a first temperature in a first reaction to generate a second nucleic acid 120s (e.g., a carrier) at interaction 116a. The second nucleic acid 120s (e.g., a nucleic acid scaffold) can comprise the first nucleic acid 104 incorporated with one or more first nucleotides 108nt_m comprising the first modified base from the first nucleoside triphosphate 108nst_m. The recombinant TdT 112 can comprise an amino acid sequence that is at least 80% identical to SEQ ID NO: 1. The recombinant TdT can comprise one or more amino acid substitution mutations at one or more positions functionally equivalent to Glu191, Lys193, Glu194, Asp242, Lys287, Phe296, Met299, Thr342, and His420 in the Bos taurus TdT of SEQ ID NO: 12.

Nucleic Acids, Nucleotides, and Nucleoside Triphosphates

In some embodiments, the first nucleic acid 104 comprise a single stranded nucleic acid, a double stranded nucleic acid with a 3' overhang, a double stranded nucleic acid with a 3' recess, or a combination thereof. The second nucleic acid 120c can comprise a single stranded nucleic acid, a double stranded nucleic acid with a 3' overhang, a double stranded nucleic acid with a 3' recess, or a combination thereof. The first nucleic acid 104 can comprise deoxyribonucleic acid (DNA). The second nucleic acid 120s can comprise deoxyribonucleic acid.

The length of the first nucleic acid 104, or the second nucleic acid 120c (or any nucleic acid of the present disclosure), can be different in different embodiments. In some embodiments, the length of the first nucleic acid, or the second nucleic acid (or any nucleic acid of the present disclosure), is, or is about, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values, nucleotides. In some embodiments, the length of the first nucleic acid, or the second nucleic acid (or any nucleic acid of the present disclosure), is at least, is at least about, is at most, or is at most about, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000, nucleotides.

The percentage and the number of nucleotides 108nt_m, 108nt_u of the first nucleic acid 104, or the second nucleic acid 120c, comprising deoxyribonucleotides can be different in different embodiments. In some embodiments, the percentage of nucleotides of the first nucleic acid, or the second nucleic acid, comprising deoxyribonucleotides is, or is about, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of nucleotides of the first nucleic acid, or the second nucleic acid, comprising deoxyribonucleotides is at least, is at least about, is at most, or is at most about, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. For example, at least 50% of nucleotides of the first nucleic acid 104 can comprise deoxyribonucleotides. For example, at least 50% of nucleotides 108nt_m, 108nt_u of the second nucleic acid 120s can comprise deoxyribonucleotides. In some embodiments, the number of nucleotides of the first nucleic acid, or the second nucleic acid, comprising deoxyribonucleotides is, or is about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values. In some embodiments, the number of nucleotides of the first nucleic acid, or the second nucleic acid, comprising deoxyribonucleotides is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 2000000, 3000000, 4000000, 5000000, 6000000, 7000000, 8000000, 9000000, 10000000.

In some embodiments, the first nucleic acid 104 comprises a single stranded nucleic acid. The second nucleic acid 120c can comprise a single stranded nucleic acid. The first nucleic acid 104 can comprise a single stranded deoxyribonucleic acid. The second nucleic acid 120c can comprise a single stranded deoxyribonucleic acid. The percentage and the number of nucleotides 108nt_m, 108nt_u of the first nucleic acid 104, or the second nucleic acid 120c, comprising ribonucleotides can be different in different embodiments. In some embodiments, the percentage of nucleotides of the first nucleic acid, or the second nucleic acid, comprising ribonucleotides is, or is about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or a number or a range between any two of these values. In some embodiments, the percentage of nucleotides of the first nucleic acid, or the second nucleic acid, comprising deoxyribonucleotides is at least, is at least about, is at most, or is at most about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10%. For example, at most 1% of nucleotides of the first nucleic acid can comprise ribonucleotides. For example, at most 1% of nucleotides of the second nucleic acid can comprise ribonucleotides. In some embodiments, the number of nucleotides of the first nucleic acid, or the second nucleic acid, comprising ribonucleotides is, or is about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values. In some embodiments, the number of nucleotides of the first nucleic acid, or the second nucleic acid, comprising ribonucleotides is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000. For example, the first nucleic acid 104 can comprise at least one ribonucleotide. For example, the second nucleic acid 120c can comprise at least one ribonucleotide.

The second nucleic acid 120c can comprise the first nucleic acid 104 incorporated with a number of the first nucleotides 108nst_m comprising the first modified base. The number of the first nucleotides 108nst_m comprising the first modified base incorporated in the second nucleic acid 120s can be different in different embodiments. In some embodiments, the number of the first nucleotides comprising the first modified base incorporated in the second nucleic acid is, or is about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values. In some embodiments, the number of the first nucleotides comprising the first modified base incorporated in the second nucleic acid is at least, is at least about, is at most, or is at most about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000. For example, the second nucleic acid 120c comprises the first nucleic acid 104 incorporated with two or more, or three or more, of the first nucleotides 108nst_m comprising the first modified base.

The percentage of the first nucleotides 108nst_m comprising the first modified base incorporated in the second nucleic acid 120s can be different in different embodiments. In some embodiments, the percentage of the first nucleotides comprising the first modified base incorporated in the second nucleic acid is, or is about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values. In some embodiments, the percentage of the first nucleotides comprising the first modified base incorporated in the second nucleic acid is at least, is at least about, is at most, or is at most about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values.

The two or more, or three or more, of the first nucleotides 108nt_m comprising the first modified base in the second nucleic acid 120c can be consecutive. The second nucleic acid 120c can comprise one or more regions of consecutive first nucleotides 108nt_m comprising the first modified base. The number of region(s) of consecutive first nucleotides 108nt_m comprising the first modified base can be different in different embodiments. In some embodiments, the number of region(s) of consecutive first nucleotides comprising the first modified base is, or is about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of region(s) of consecutive first nucleotides comprising the first modified base is at least, is at least about, is at most, or is at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, or 10000. The number of consecutive first nucleotides 108nt_m comprising the first modified bases in a region of the second nucleic acid 120c can be different in different embodiments. In some embodiments, the number of consecutive first nucleotides comprising the first modified bases in a region of the second nucleic acid is, or is about, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of consecutive first nucleotides comprising the first modified bases in a region of the second nucleic acid is, or is about, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The first modified base of the first nucleoside triphosphate 108nst_m (or any modified bases of nucleoside triphosphates of the present disclosure) can comprise a modified adenine, a modified guanine, a modified cytosine, a modified thymine, or a modified uracil. The first nucleoside triphosphate (or any nucleoside triphosphates of the present disclosure) can comprise, for example, 5-(15-Azido-4,7,10,13-tetraoxa-pentadecanoyl-aminoallyl)-2'-deoxyuridine-5'-triphosphate (Azide-PEG4-aminoallyl-dUTP), $N^6$-(6-Azido)hexyl-3'-deoxyadenosine-5'-triphosphate ($N^6$-(6-Azido)hexyl-3'-dATP), or a combination thereof.

In some embodiments, the first nucleoside triphosphate 108nst_m comprises the first modified base and a first accessory oligonucleotide (e.g., a P7 adapter oligonucleotide, or a (e.g., a P adapter oligonucleotide). The first nucleoside triphosphate 108nst_m can comprise the first modified base and the first accessory oligonucleotide covalently linked.

Reaction

The first reaction time during which the first nucleic acid 104 and the first nucleoside triphosphate 108nst_m comprising the first modified base are contacted with a recombinant terminal deoxynucleotidyl transferase 112 can be different in different embodiments. For example, the first reaction time is at least 10 minutes (mins). In some embodiments, the first reaction time (or any reaction time of the present disclosure) is, or is about, 1 second (sec), 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, or a number or a range between any two of these values. In some embodiments, the first reaction time (or any reaction time of the present disclosure) is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, or a number or a range between any two of these values.

The first reaction temperature at which the first nucleic acid 104 and the first nucleoside triphosphate 108nst_m comprising the first modified base are contacted with a recombinant terminal deoxynucleotidyl transferase 112 in the first reaction can be different in different embodiments. In some embodiments, the first reaction temperature (or any reaction temperature of the present disclosure) is, or is about, 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values. In some embodiments, the first reaction temperature (or any reaction temperature of the present disclosure) is at least, is at least about, is at most, or is at most about, 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values. For example, the first temperature can be at least 37° C. to at least 58° C.

The concentration of the first nucleic acid 104 in the first reaction can be different in different embodiments. In some embodiments, the concentration of the first nucleic acid (or any nucleic acid of the present disclosure) in the first reaction (or any reaction of the present disclosure) is, or is about, 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, or a number or a range between any two of these values. In some embodiments, the concentration of the first nucleic acid (or any nucleic acid of the present disclosure) in the first reaction (or any reaction of the present disclosure) is at least, is at least about, is at most, or is at most about, 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, or 100 µM. For example, the concentration of the first nucleic acid 104 in the first reaction can be at least 10 nM.

The concentration of the first nucleoside triphosphate 108nst_m comprising the first modified base in the first reaction can be different in different embodiments. In some embodiments, the concentration of the first nucleoside triphosphate (or any nucleotide triphosphate of the present disclosure) in the first reaction (or any reaction of the present disclosure) is, or is about, 0.001 µM, 0.002 µM, 0.003 µM, 0.004 µM, 0.005 µM, 0.006 µM, 0.007 µM, 0.008 µM, 0.009 M, 0.01 µM, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 M, 6 µM, 7 µM, 8 µM, 9 µM, 10 µM, 20 µM, 30 µM, 40 µM, 50 µM, 60 m, 70 µM, 80 µM, 90 µM, 100 µM, or a number or a range between any two of these values.

In some embodiments, the concentration of the first nucleoside triphosphate (or any nucleotide triphosphate of the present disclosure) in the first reaction (or any reaction of the present disclosure) is at least, is at least about, is at most, or is at most about, 0.001 µM, 0.002 µM, 0.003 µM, 0.004 µM, 0.005 µM, 0.006 µM, 0.007 µM, 0.008 µM, 0.009 µM, 0.01 µM, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 jM, 5 µM, 6 µM, 7 µM, 8 µM, 9 µM, 10 µM, 20 µM, 30 jM, 40 jM, 50 µM, 60 µM, 70 µM, 80 µM, 90 µM, or 100 µM. For example, the concentration of the first nucleoside triphosphate 108nst_m in the first reaction can be at least 0.1 µM.

The concentration of the recombinant TdT 112 in the first reaction can be different in different embodiments. In some embodiments, the concentration of the recombinant TdT in the first reaction is, or is about, 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, or a number or a range between any two of these values. In some embodiments, the concentration of the recombinant TdT in the first reaction is at least, is at least about, is about most, or is at most about, 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, M, 30 µM, 40 µM, 50 µM, 60 µM, 70 µM, 80 µM, 90 µM, or 100 µM. For example, the concentration of the recombinant TdT 112 in the first reaction can be at least 0.1 µM.

Additional Nucleotides and Nucleoside Triphosphates

In some embodiments, providing the first nucleic acid and the first nucleoside triphosphate comprising the first modified base comprises providing the first nucleic acid, the first nucleoside triphosphate comprising the first modified base, and a second nucleoside triphosphate (e.g., the nucleotide triphosphate 108nst_u). Contacting the first nucleic acid and the first nucleoside triphosphate comprising the first modified base with the recombinant TdT at block 116a can comprise contacting the first nucleic acid, the first nucleoside triphosphate comprising the first modified base, and the second nucleoside triphosphate with the recombinant TdT for the first reaction time at the first temperature in the first reaction at block 116a to generate the second nucleic acid 120c. The second nucleic acid 120s can comprise the first nucleic acid 104 incorporated with (i) one or more of the first nucleotides 108nst_m comprising the first modified base from the first nucleoside triphosphate and (ii) one or more second nucleotides (e.g., nucleotides 108nt_u with unmodified bases).

In some embodiments, each of the one or more second nucleotides comprises a second modified base from the second nucleoside triphosphate. The second modified base of the second nucleoside triphosphate can comprise a modified adenine, a modified guanine, a modified cytosine, a modified thymine, or a modified uracil. The second nucleoside triphosphate (or any nucleoside triphosphates of the present disclosure) can comprise, for example, 5-(15-Azido-4,7,10,13-tetraoxa-pentadecanoyl-aminoallyl)-2'-deoxyuridine-5'-triphosphate (Azide-PEG4-aminoallyl-dUTP), $N^6$-(6-Azido)hexyl-3'-deoxyadenosine-5'-triphosphate ($N^6$-(6-Azido)hexyl-3'-dATP), or a combination thereof.

In some embodiments, the second nucleoside triphosphate comprises the second modified base and a second accessory oligonucleotide (e.g., a P7 adapter oligonucleotide, or a P5 adapter oligonucleotide). The second nucleoside triphosphate can comprise the second modified base and the second accessory oligonucleotide covalently linked.

The first modified base of the first nucleoside triphosphate 108nst_m and the second modified base of the second nucleoside triphosphate can comprise modifications of a same unmodified base, such as modifications of an adenine (or a guanine, a cytosine, a thymine, or an uracil). The first modified base of the first nucleoside triphosphate 108nst_m and the second modified base of the second nucleoside triphosphate can comprise modification of different unmodified bases, such as modifications of an adenine and a guanine.

In some embodiments, each of the second nucleotides comprises a second unmodified base from the second nucleoside triphosphate (e.g., the nucleoside triphosphate with unmodified bases 108nst_u). The second unmodified base of the second nucleoside triphosphate can comprise an adenine, a guanine, a cytosine, a thymine, or an uracil. The first modified base of the first nucleoside triphosphate 108nst_m can comprise a modification of the second unmodified base. For example, the first nucleoside triphosphate 108nst_m can comprise a modified adenine, and the second nucleoside triphosphate can comprise an adenine.

The percentage of total nucleoside triphosphates being the first nucleoside triphosphate 108nst_m (or any nucleoside triphosphate of the present disclosure, such as a second nucleoside triphosphate) in the first reaction can be different in different embodiments. In some embodiments, the percentage of total nucleoside triphosphates being the first nucleoside triphosphate (or any nucleoside triphosphate of the present disclosure) in the first reaction is, or is about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 30%, 40%, 50%, 60%, 70%, 80%, 90%, 95%, 96%, 97%, 98%, 99%, 99.9%, or a number or a range between any two of these values. In some embodiments, the percentage of total nucleoside triphosphates being the first nucleoside triphosphate (or any nucleoside triphosphate of the present disclosure) in the first reaction is at least, is at least about, is at most, or is at most about, 0.001%, 0.002%, 0.003%, 0.004%, 0.005%, 0.006%, $0.0^{07}$%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 30%, 40%, 50%, 60%, 70%, 80%, 90%, 95%, 96%, 97%, 98%, 99%, or 99.9%.

The first nucleoside triphosphate 108nst_m comprising the first modified base and the second nucleoside triphosphate (or two or more second nucleoside triphosphates, including all second nucleoside triphosphates) can be contacted with the first nucleic acid 104 at different ratios in different embodiments. In some embodiments, the ratio of the first nucleoside triphosphate comprising the first modified base and the second nucleoside triphosphate (or two or more second nucleoside triphosphates, including all second nucleoside triphosphates) contacted with the first nucleic acid is, or is about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, or a number or a range between any two of these values. In some embodiments, the ratio of the first nucleoside triphosphate comprising the first modified base and the second nucleoside triphosphate (or two or more second nucleoside triphosphates, including all second nucleoside triphosphates) contacted with the first nucleic acid is at least, is at least about, is at most, or is at most about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1. For example, the first nucleoside triphosphate 108nst_m comprising the first modified base and the second nucleoside triphosphate are contacted with the first nucleic acid 104 at a ratio that ranges from about 1:100 to about 100:1.

The first nucleotide 108nt_m comprising the first modified base and the second nucleotide (or two or more second nucleoside triphosphates, including all second nucleoside triphosphates) can be incorporated in the second nucleic acid 120s at different ratios in different embodiments. In some embodiments, the ratio of the first nucleotide comprising the first modified base and the second nucleotide (or two or more second nucleoside triphosphates, including all second nucleoside triphosphates) incorporated in the second nucleic acid is, or is about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, or a number or a range between any two of these values. In some embodiments, the ratio of the first nucleotide comprising the first modified base and the second nucleotide (or two or more second nucleoside triphosphates, including all second nucleoside triphosphates) incorporated in the second nucleic acid is at least, is at least about, is at most, or is at most about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1. For example, the first nucleotide 108nt_m comprising the first modified base and the second nucleotide (e.g., 108nt_u) can be incorporated into the second nucleic acid 120s at a ratio that ranges from about 1:100 to about 100:1.

In some embodiments, providing the first nucleic acid 104 and the first nucleoside triphosphate 108nst_m comprising the first modified base comprises providing the first nucleic acid 104, the first nucleoside triphosphate 108nst_m comprising the first modified base, and a plurality of second nucleoside triphosphates. Contacting the first nucleic acid 104 and the first nucleoside triphosphate 108nst_m comprising the first modified base with the recombinant TdT 112 at action 116a can comprise contacting the first nucleic acid 104, the first nucleoside triphosphate 108nst_m comprising the first modified base, and the plurality of second nucleoside triphosphates with the recombinant TdT 112 for the first reaction time at the first temperature in the first reaction to generate the second nucleic acid 120s at 1116a. The second nucleic acid 120s can comprise the first nucleic acid 104 incorporated with one or more of the first nucleotides 1108nt_m comprising the first modified base and one or more second nucleotides from the plurality of second nucleoside triphosphates.

In some embodiments, the plurality of second nucleoside triphosphates comprises a deoxyribose adenine triphosphate, a deoxyribose guanine triphosphate, a deoxyribose cytosine triphosphate, a deoxyribose thymine triphosphate, a deoxyribose uracil triphosphate, or a combination thereof. The number of second nucleoside triphosphates of the plurality of nucleoside triphosphates each comprising a second unmodified base can be different in different embodiments, such as 1, 2, 3, 4, 5, 6, 7, 8, 9, 10, 20, 30, 40, 50, 60, 70, 80, 90, 100, or a number or a range between any two of these values. For example, at least one, or each, of the plurality of second nucleoside triphosphates can comprise a second unmodified base. The number of second nucleoside triphosphates of the plurality of nucleoside triphosphates each comprising a second modified base can be different in different embodiments, such as 1, 2, 3, 4, 5, 6, 7, 8, 9, 10, 20, 30, 40, 50, 60, 70, 80, 90, 100, or a number or a range between any two of these values. For example, at least one, or each, of the plurality of second nucleoside triphosphates can comprise a second modified base. The ratio of the second nucleoside triphosphates each comprising a second modified base and the second nucleoside triphosphates each comprising a second unmodified base can be different in different embodiments, such as 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1.

Two of the plurality of second nucleoside triphosphates can be contacted with the first nucleic acid 104 different ratios in different embodiments. In some embodiments, the ratio of two of the plurality of second nucleoside triphosphates contacted with the first nucleic acid is, or is about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, or a number or a range between any two of these values. In some embodiments, In some embodiments, the ratio of two of the plurality of second nucleoside triphosphates contacted with the first nucleic acid is at least, is at least about, is at most, or is at most about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1. For example, two of the plurality of second nucleoside triphosphates can be contacted with the first nucleic acid at a ratio that ranges from about 1:100 to about 100:1.

Two of the plurality of second nucleoside triphosphates can be incorporated in the second nucleic acid 120s at different ratios in different embodiments. In some embodiments, the ratio of two of the plurality of second nucleoside triphosphates incorporated in the second nucleic acid is, or is about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, or a number or a range between any two of these values. In some embodiments, In some embodiments, the ratio of two of the plurality of second nucleoside triphosphates incorporated in the second nucleic acid is at least, is at least about, is at most, or is at most about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1. For example, two of the second nucleotides can be incorporated into the second nucleic acid at a ratio that ranges from about 1:100 to about 100:1.

Modified bases and unmodified bases of nucleotides can be incorporated into the second nucleic acid 120c at different ratios in different embodiments. In some embodiments, modified bases and unmodified bases of nucleotides can be incorporated into the second nucleic acid 120c at a ratio of, or of about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, or a number or a range between any two of these values. In some embodiments, modified bases and unmodified bases of nucleotides can be incorporated into the second nucleic acid at a ratio of at least, at least about, at most, or at most about, 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1000:1. For example, modified bases and unmodified bases of nucleotides can be incorporated into the second nucleic acid at a ratio that ranges from about 1:100 to about 100:1. The modified bases can comprise the first modified base and/or a base of at least one (such as 1, 2, 3, 4, 5, 6, 7, 8, 9, 10, 100, 200, 300, 400, 500, 600, 700, 800, 900, or 1,000), or each, of the plurality of second nucleotides incorporated into the second nucleic acid. The unmodified bases can comprise the base of at least one, or each, of the plurality of second nucleotides incorporated into the second nucleic acid.

The percentage of the nucleotide bases of the second nucleic acid 120s comprising modified bases can be different in different embodiments. In some embodiments, the percentage of the nucleotide bases of the second nucleic acid comprising modified bases (or unmodified bases) is, or is about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9%, or a number or a range between any two of these values. In some embodiments, the percentage of the nucleotide bases of the second nucleic acid comprising modified bases (or unmodified bases) is at least, is at least about, is at most, or is at most about, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53% 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, $9^2$%, $9^3$%, 94%, 95%, 96%, 97%, 98%, 99%, or 99.9%. For example, at least 1% of the nucleotide bases of the second nucleic acid comprise modified bases. For example, at least 1% of the nucleotide bases of the second nucleic acid comprise the first modified base. The modified bases can be distributed throughout the second nucleic acid. The modified bases can be distributed randomly throughout the second nucleic acid.

The second nucleic acid 120c can comprise a number of region(s) of consecutive modified (or unmodified bases). In some embodiments, the number of region(s) of consecutive modified (or unmodified bases) in the second nucleic acid 120c is, or is about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of region(s) of consecutive modified (or unmodified bases) in the second nucleic acid 120c is at least, is at least about, is at most, or is at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, or 10000. The length of a region of consecutive modified (or unmodified bases) in the second nucleic acid 120c can be different in different embodiments. In some embodiments, the length of a region of consecutive modified (or unmodified bases) in the second nucleic acid is, or is about, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the length of a region of consecutive modified (or unmodified bases) in the second nucleic acid is at least, is at least about, is at most, or is at most about, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000. For example, the second nucleic acid 120c can comprise a plurality of consecutive modified bases, such as two or more, or three or more, consecutive modified bases.

Carrier

Referring to FIG. 1, the first nucleic acid 104 can comprise a template capture site 104tcs capable of binding (e.g., hybridizing to) a nucleic acid template 128. The template capture site 104tcs can comprise a template capture sequence. The nucleic acid template 128 can comprise a sequence that is capable of hybridizing to the template capture sequence. The sequence of the nucleic acid template 128 that is capable of hybridizing to the template capture sequence and the reverse complement of the template capture sequence can have different sequence identity in different embodiments. In some embodiments, the sequence of the nucleic acid template that is capable of hybridizing to the template capture sequence and the reverse complement of the template capture sequence have, or have about, a sequence identity of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the sequence of the nucleic acid template that is capable of hybridizing to the template capture sequence and the reverse complement of the template capture sequence have at least, have at least about, have at most, or have at most about, a sequence identity of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. For example, the nucleic acid template 128 can comprise a sequence that has at least 90% sequence identity to a reverse complement of the template capture. The nucleic acid template 128 can comprise a single stranded nucleic acid, such as a single stranded DNA.

In some embodiments, one or more of the first modified base of the first nucleoside triphosphate 108nst_m and the first nucleotide 108nt_m incorporated in the second nucleic acid 120s comprise a functional moiety 108fm. The functional moiety 108fm of the first modified base can be capable of participating in a click chemistry reaction. The first modified base of the first nucleoside triphosphate 108nst_m and the first nucleotide 108nt_m in the second nucleic acid 120s can comprise a first saturated or unsaturated, substituted or unsubstituted, straight or branched aliphatic carbon chain. The functional moiety and the base of the first modified base can be on two ends of the first modified base covalently linked by the first saturated or unsaturated, substituted or unsubstituted, straight or branched aliphatic carbon chain. For example, the first nucleoside triphosphate can be 5-(15-Azido-4,7,10,13-tetraoxa-pentadecanoyl-aminoallyl)-2'-deoxyuridine-5'-triphosphate (azide-PEG4-aminoallyl-dUTP) or N6-(6-Azido)hexyl-2'deoxy-adenosine-5'-triphosphate ($N^6$-(6-Azido)hexyl-dATP).

One or more of the second modified base of the second nucleoside triphosphate and the second nucleotide incorporated in the second nucleic acid 120s can comprise a functional moiety. The functional moiety of the second modified base can be capable of participating in a click chemistry reaction. The second modified base of the second nucleoside triphosphate and the second nucleotide in the second nucleic acid 120s can comprise a second saturated or unsaturated, substituted or unsubstituted, straight or branched aliphatic carbon chain. The functional moiety and the base of the second modified base can be on two ends of the second modified base covalently linked by the second saturated or unsaturated, substituted or unsubstituted, straight or branched aliphatic carbon chain.

The aliphatic carbon chain can be covalently linked (e.g., by a single bond, a double bond, or a triple bond, or conjugated) to a base of a modified base (e.g., the first modified base of the first nucleoside triphosphate 108nst_m and the first nucleotide 108nt_m in the second nucleic acid 120s or the second modified base of the second nucleoside triphosphate and the second nucleotide in the second nucleic acid 120s). The functional moiety (e.g., the first functional moiety 108fm or the second functional moiety) can be covalently linked to the aliphatic carbon chain by a single bond, a double bond, or a triple bond.

The aliphatic carbon chain can be different in different embodiments. In some embodiments, the aliphatic carbon chain is saturated. In some embodiments, the aliphatic carbon chain is unsaturated. In some embodiments, the aliphatic carbon chain is substituted. In some embodiments, the aliphatic carbon chain is unsubstituted. In some embodiments, the aliphatic carbon chain is straight. In some embodiments, the aliphatic carbon chain is branched. In some embodiments, the length of the aliphatic carbon chain is, or is about, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the length of the aliphatic carbon chain is at least, is at least about, is at most, or is at most about, 2, 3, 4, 5, 6, 7, 8, 9, 10, 20, 30, 40, 50, 60, 70, 80, 90, 100, 200, 300, 400, 500, 600, 700, 800, 900, 1000. The aliphatic carbon chain can comprise polyethylene glycol (PEG). In some embodiments, the PEG has a n, the number of the ethylene glycol (—$OCH_2CH_2$—) repeating unit, of, or of about, 1, 2, 3, 4, 5, 6, 7, 8, 9, 10, 20, 30, 40, 50, 60, 70, 80, 90, 100, or a number or a range between any two of these values. In some embodiments, the PEG has a n, the number of ethylene glycol (—$OCH_2CH_2$—) repeating unit, of at least, of at least about, or at most, or of at most about, 1, 2, 3, 4, 5, 6, 7, 8, 9, 10, 20, 30, 40, 50, 60, 70, 80, 90, or 100.

The functional moiety of 108fm of the first modified base of the of the first nucleoside triphosphate 108nst_m and the first nucleotide 108nt_m incorporated in the second nucleic acid 120s and the functional moiety of the second modified base of the second nucleoside triphosphate and the second nucleotide incorporated in the second nucleic acid 120s can the identical, or different. The functional moieties of the modified bases of two of the plurality of second nucleoside triphosphates and the second nucleotides incorporated in the second nucleic acid 120s can be identical, or different. The functional moieties of the modified bases of all of the plurality of second nucleoside triphosphates and the second nucleotides incorporated in the second nucleic acid 120s can be identical, or different.

The method comprises providing a first accessory oligonucleotide 124ao1 (e.g., a P5 adapter oligonucleotide), or a first accessory comprising the first accessory oligonucleotide 124ao1. The method can comprise, at action 116c, contacting the second nucleic acid 120s with the first accessory oligonucleotide 124ao1 for a second reaction time at a second temperature in a second reaction to generate a third nucleic acid 120c (e.g., a carrier) comprising the second nucleic acid 120c attached to one or more of the first accessory oligonucleotides 124ao1.

In some embodiments, providing the first accessory oligonucleotide 124ao1 comprises providing the first accessory oligonucleotide 124ao1 and a second accessory oligonucleotide 124ao2 (e.g., a P7 adapter oligonucleotide), or a second accessory comprising the second accessory oligonucleotide 124ao2. Contacting the second nucleic acid 120s with the first accessory oligonucleotide 124ao1 can comprise contacting the second nucleic acid 120s with the first accessory oligonucleotide 124ao1 and the second accessory oligonucleotide 124ao2 for the second reaction time at the second temperature in the second reaction to generate the third nucleic acid 120c comprising the second nucleic acid 120s attached to one or more of the first accessory oligonucleotides 124ao1 and one or more of the second accessory oligonucleotides 124ao2.

In some embodiments, providing the first accessory oligonucleotide comprises providing a first accessory comprising the first accessory oligonucleotide 124ao1 and a first polymer. Contacting the second nucleic acid 120s with the first accessory oligonucleotide 124ao1 can comprise contacting the second nucleic acid 120s with the first accessory for the second reaction time at the second temperature in the second reaction to generate the third nucleic acid 120c comprising the second nucleic acid 120s attached to one or more of the first accessories. Providing the second accessory oligonucleotide 124ao2 can comprise providing a second accessory comprising the second accessory oligonucleotide 124ao2 and a second polymer. Contacting the second nucleic acid 120s with the second accessory can comprise contacting the second nucleic acid 120s and the second accessory for the second reaction time at the second temperature in the second reaction to generate the third nucleic acid 120c comprising the second nucleic acid 120s attached to one or more of the second accessories. The first accessory can comprise the first accessory oligonucleotide 124ao1 and the first polymer covalently linked. The second accessory can comprise the second accessory oligonucleotide 124ao2 and the second polymer covalently linked.

A dimension (e.g., the diameter) of the third nucleic acid 128c with or without any accessory oligonucleotides attached, (or any nucleic acid of the present disclosure), can be different in different embodiments. In some embodiments, the dimension of the third nucleic acid (or any nucleic acid of the present disclosure) is, or is about, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, or a number or a range between any two of these values. In some embodiments, the dimension of the third nucleic acid (or any nucleic acid of the present disclosure) is at least, is at least about, is at most, or is at most about, 0.04 nm, 0.05 nm, 0.06 nm, 0.07 nm, 0.08 nm, 0.09 nm, 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, or 1000 nm.

In some embodiments, the first accessory oligonucleotide 124ao2 comprises a first adapter sequence 124as1, or a reverse complement thereof. The second accessory oligonucleotide can comprise a second adapter sequence 124as2, or a reverse complement thereof. In some embodiments, the first adapter sequence comprises a P5 sequence. The second adapter sequence can comprise a P7 sequence.

The length of the first accessory oligonucleotide (e.g., the first accessory oligonucleotide 124ao1 or the first accessory oligonucleotide in the first nucleotide triphosphate 108nst_m), the second accessory oligonucleotide (e.g., the second accessory oligonucleotide 124ao2 or the second accessory oligonucleotide in the second nucleotide triphosphate), or any oligonucleotide of the present disclosure, can be different in different embodiments. In some embodiments, the length of the first accessory oligonucleotide (or the second accessory oligonucleotide, or any oligonucleotide of the present disclosure) is, or is about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, nucleotides. In some embodiments, the length of the first accessory oligonucleotide (or the second accessory oligonucleotide, or any oligonucleotide of the present disclosure) is at least, is at least about, is at most, or is at most about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 200, 300, 400, 500, 600, 700, 800, 900, or 1000, nucleotides. For example, the first accessory oligonucleotide and/or the second accessory oligonucleotide each can be about 10 nucleotides to about 100 nucleotides in length.

The third nucleic acid 120c can comprise the second nucleic acid 120s attached to one or more of the first accessory oligonucleotides 124ao1. The third nucleic acid 120c can comprise the second nucleic acid 120s attached to one or more of the second accessory oligonucleotides. The third nucleic acid 120c can comprise different numbers of first accessory oligonucleotides, or the second accessory oligonucleotides, in different embodiments. In some embodiments, the third nucleic acid comprises, or comprises about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values, first accessory oligonucleotides, or the second accessory oligonucleotides. In some embodiments, the third nucleic acid comprises at least, comprises at least about, comprises at most, or comprises at most about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000, first accessory oligonucleotides, or the second accessory oligonucleotides. For example, the third nucleic acid can comprise about 10 to about 1000000 of the first accessory oligonucleotides. For example, the third nucleic acid can comprise about 10 to about 1,000,000 of the second accessory oligonucleotides.

In some embodiments, providing the first accessory oligonucleotide comprises providing a first accessory comprising the first accessory oligonucleotide and a first polymer. Contacting the second nucleic acid with the first accessory oligonucleotide can comprise contacting the second nucleic acid with the first accessory for the second reaction time at the second temperature in the second reaction to generate the third nucleic acid comprising the second nucleic acid attached to one or more of the first accessories. Providing the second accessory oligonucleotide can comprise providing a second accessory comprising the second accessory oligonucleotide with a second polymer. Contacting the second nucleic acid with the second accessory can comprise contacting the second nucleic acid and the second accessory for the second reaction time at the second temperature in the second reaction to generate the third nucleic acid comprising the second nucleic acid attached to one or more of the second accessories. The first accessory can comprise the first accessory oligonucleotide and the first polymer covalently linked. The second accessory can comprise the second accessory oligonucleotide and the second polymer covalently linked Referring to FIG. 1, the first accessory oligonucleotide 124ao1 comprises a first functional moiety 124fm1. The second accessory oligonucleotide 124ao2 can comprise a second functional moiety 124fm2. The first functional moiety 124fm1 of the first accessory oligonucleotide 124ao1 can be on the 5' end of the first accessory oligonucleotide 124ao1. The first functional moiety 124fm1 of the first accessory oligonucleotide 124ao1 can be attached to an internucleotide linkage of the first accessory oligonucleotide 124ao1. A modified base of a nucleotide in the first accessory oligonucleotide can comprise the first functional moiety 124fm1 of the first accessory oligonucleotide 124ao1. The first functional moiety 124fm1 of the first accessory oligonucleotide 124ao1 can be attached to a sugar of a nucleotide of the first accessory oligonucleotide 124ao1. The second functional moiety 124fm2 of the second accessory oligonucleotide 124ao2 can be on the 5' end of the second accessory oligonucleotide 124ao2. The second functional moiety 124fm2 of the second accessory oligonucleotide 124ao2 can be attached to an internucleotide linkage of the second accessory oligonucleotide 124ao2. A modified base of a nucleotide in the second accessory oligonucleotide can comprise the second functional moiety 124fm2 of the second accessory oligonucleotide 124ao2. The second functional moiety 124fm2 of the second accessory oligonucleotide 124ao2 can be attached to a sugar of a nucleotide of the second accessory oligonucleotide 124ao2.

In some embodiments, the first functional moiety 124fm1 of the first accessory oligonucleotide 124ao1 and the second functional moiety 124fm2 of the second accessory oligonucleotide 124ao2 are identical. The first functional moiety 124fm1 of the first accessory oligonucleotide 124ao1 can be capable of reacting with the functional moiety 108fm of the first modified base of the first nucleotide 108nt_m to form a covalent linkage. The second functional moiety 124fm2 of the second accessory oligonucleotide 124ao2 can be capable of reacting with the functional moiety 108fm of the first modified base of the first nucleotide 108nt_m to form a covalent linkage. The first functional moiety 124fm1 of the first accessory oligonucleotide 124ao1 can be capable of reacting with the functional moiety of the second modified base of the second nucleotide to form a covalent linkage. The second functional moiety 124fm2 of the second accessory oligonucleotide 124ao2 can be capable of reacting with the functional moiety of the second modified base of the second nucleotide to form a covalent linkage.

In some embodiments, the first functional moiety 124fm1 of the first accessory oligonucleotide 124ao1 is capable of participating in a click chemistry reaction. The second functional moiety 124fm2 of the second accessory oligonucleotide 124ao2 can be capable of participating in a click chemistry reaction. In some embodiments, the first functional moiety 124fm1 of the first accessory oligonucleotide 124ao1 is capable of participating in a click chemistry reaction with the functional moiety 108fm of the first modified base of the first nucleotide 128nt_m (or the functional moiety of the second modified base of the second nucleotide) incorporated in the second nucleic acid. The second functional moiety 124fm2 of the second accessory oligonucleotide 124ao2 can be capable of participating in a click chemistry reaction with the functional moiety 108fm of the first modified base of the first nucleotide 108nt_m (or the functional moiety of the second modified base of the second nucleotide).

In some embodiments, the first functional moiety 124fm1 of the first accessory oligonucleotide 124ao1, the second functional moiety 124fm2 of the second accessory oligonucleotide 124ao1, the functional moiety 108fm of the first modified base of the first nucleoside triphosphate 108nst_m, the functional moiety 108fm of the first nucleotide 108nt_m, the functional moiety of the second modified base of the second nucleoside triphosphate, and the functional moiety of the second nucleotide, are independently an azide, an alkynyl, an alkenyl, a thiol, a nitrone, or a combination thereof. The functional moiety of the first modified base of the first nucleotide and the first functional moiety of the first accessory oligonucleotide, the functional moiety of the first modified base of the first nucleotide and the second functional moiety of the second accessory oligonucleotide, the functional moiety of the second modified base of the second nucleotide and the first functional moiety of the first accessory oligonucleotide, and/or the functional moiety of the second modified base of the second nucleotide and the second functional moiety of the second accessory oligonucleotide, can be independently selected from the following pairs: (i) azido/alkynyl; (ii) alkynyl/azido; (iii) thiol/alkynyl; (iv) alkynyl/thiol; (v) alkenyl/thiol; (vi) thiol/alkenyl; (vii) azido/cyclooctynyl; (viii) cyclooctynyl/azido; (ix) nitrone/cyclooctynyl; and (x) cyclooctynyl/nitrone. For example, the functional moiety of the first modified base of the first nucleotide and/or the functional moiety of the second modified base of the second nucleotide can be independently an azido. The first functional moiety of the first accessory oligonucleotide and/or the second functional moiety of the second accessory oligonucleotide can be independently an alkynyl.

In some embodiments, the click chemistry reaction comprises copper catalyzed azide-alkyne cycloaddition (CuAAC). The covalent linkage can comprise a triazolyl. The CuAAC can comprise a Cu(I) stabilizing ligand. The Cu(I) stabilizing ligand can be selected from the group consisting of: 3-[4-({bis[(1-tert-butyl-1H-1,2,3-triazol-4-yl)methyl]amino}methyl)-1H-1,2,3-triazol-1-yl]propanol (BTTP), 3-[4-({bis[(1-tert-butyl-1H-1,2,3-triazol-4-yl)methyl]amino}methyl)-1H-1,2,3-triazol-1-yl]propyl hydrogen sulfate (BTTPS), 2-[4-({bis[(1-tert-butyl-1H-1,2,3-triazol-4-yl)methyl]amino}methyl)-1H-1,2,3-triazol-1-yl]ethyl hydrogen sulfate (BTTES), 2-[4-{(bis[(1-tert-butyl-1H-1,2,3-triazol-4-yl)methyl]amino)methyl}-1H-1,2,3-triazol-1-yl]-acetic acid (BTTAA), bathophenanthroline disulfonate disodium salt (BPS), N,N,N',N'',N''-Pentamethyldiethylenetriamine (PMDETA), tris-((1-benzyl-1H-1,2,3-triazol-4-yl)methyl)amine (TBTA), Tris(3-hydroxypropyltriazolylmethyl)amine (THPTA), $N^E$-((1R,2R)-2-azidocyclopentyloxy)carbonyl)-L-lysine (ACPK), and 4-N,N-dimethyl amino-1,8-naphthalimide (4-DMN).

In some embodiments, the click chemistry reaction comprises strain-promoted azide-alkyne cycloaddition (SPAAC). The covalent linkage can comprise a cyclooctatriazolyl. In some embodiments, the click chemistry reaction comprises alkyne hydrothiolation. The covalent linkage can comprise an alkenyl sulfide. In some embodiments, the click chemistry reaction comprises alkene hydrothiolation. The covalent linkage can comprise an alkyl sulfide. In some embodiments, the click chemistry reaction comprises strain-promoted alkyne-nitrone cycloaddition (SPANC). The covalent linkage can comprise an octahydrocycloocta-isoxazolyl.

The cyclooctynyl can be dibenzylcyclooctyne (DBCO) or a derivative thereof. In some embodiments, the click chemistry reaction is biocompatible.

The second temperature at which the second nucleic acid 120s is contacted with the first accessory oligonucleotide 124ao1 and/or the second accessory oligonucleotide 124ao2 in the second reaction at interaction 116c can be different in different embodiments. In some embodiments, the second temperature is, or is about, −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values. In some embodiments, the second temperature is at least, is at least about, is at most, or is at most about, −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., or 90° C. For example, the second temperature is about 20° C. to about 65° C. For example, the second temperature can be less than 0° C. For example, the second temperature can be about −4° C. to about −20° C.

The second reaction time during which the second nucleic acid 120s is contacted with the first accessory oligonucleotide 124ao1 and/or the second accessory oligonucleotide 124ao2 in the second reaction at interaction 116c can be different in different embodiments. For example, the second reaction time is at least 10 minutes (mins). In some embodiments, the second reaction time (or any reaction time of the present disclosure) is, or is about, 1 second (sec), 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, or a number or a range between any two of these values. In some embodiments, the second reaction time (or any reaction time of the present disclosure) is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 24 hrs, or a number or a range between any two of these values.

Referring to FIG. 1, the method can comprise providing the nucleic acid template 128 comprising the first adapter sequence 124as1, or a reverse complement thereof, and the second adapter sequence 124as2, or a reverse complement thereof. The method can comprise contacting the third nucleic acid 120c with the nucleic acid template 128 to generate the third nucleic acid 120c with the nucleic acid template 128 hybridized to the template capture site 104tcs on the third nucleic acid 120c at action 116c. The method can comprise, at action 116d, performing amplification (e.g., bridge amplification or exclusion amplification) on the third nucleic acid 120c hybridized with the nucleic acid template 128 to generate a fourth nucleic acid 120n (referred to herein as a nanoparticle) comprising the third nucleic acid 120c attached to one or more of the first accessory oligonucleotides 124ao1 and one or more of the second accessory oligonucleotides 124ao2 extended to comprise a sequence of the nucleic acid template 128, or a reverse complement thereof. The method can comprise determining the sequence of the nucleic acid template 128 using the fourth nucleic acid 120n.

A dimension (e.g., the diameter) of the nanoparticle 120n (or the second nucleic acid 120s, such as a scaffold, or the third nucleic acid 120c, such as a carrier) can be different in different embodiments. In some embodiments, the dimension of the nanoparticle (or the second nucleic acid, or the third nucleic acid) is, or is about, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, or a number or a range between any two of these values. In some embodiments, the dimension of the nanoparticle (or the second nucleic acid, or the third nucleic acid) is at least, is at least about, is at most, or is at most about, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, or 1000 nm. A nanoparticle with a sufficient spatial dimension can be capable of occupying a single well on a substrate (e.g., a flow cell) by excluding other nanoparticles from occupying the same well by steric clashes or hinderance, therefore resulting in monoclonality, or close to monoclonality, in sequencing-by-synthesis.

Polymer

In some embodiments, contacting the ssDNA scaffold 120s with the first adapter oligonucleotide 124ao1 comprises contacting the ssDNA scaffold with a first adapter comprising the first adapter oligonucleotide 124ao1 and a first polymer. Contacting the ssDNA scaffold 120s with the second adapter oligonucleotide 124ao2 can comprise contacting the ssDNA scaffold with a second adapter comprising the second adapter oligonucleotide 124ao2 and a second polymer. The first adapter can comprise the first adapter oligonucleotide 124ao1 and the first polymer covalently linked. The second adapter can comprise the second adapter oligonucleotide 124ao2 and the second polymer covalently linked. In some embodiments, providing the first accessory oligonucleotide comprises providing a first accessory comprising the first accessory oligonucleotide 124ao1 and a first polymer. Contacting the second nucleic acid 120s with the first accessory oligonucleotide 124ao1 can comprise contacting the second nucleic acid 120s with the first accessory for the second reaction time at the second temperature in the second reaction to generate the third nucleic acid 120c comprising the second nucleic acid 120s attached to one or more of the first accessories. Providing the second accessory oligonucleotide 124ao2 can comprise providing a second accessory comprising the second accessory oligonucleotide 124ao2 and a second polymer. Contacting the second nucleic acid 120s with the second accessory can comprise contacting the second nucleic acid 120s and the second accessory for the second reaction time at the second temperature in the second reaction to generate the third nucleic acid 120c comprising the second nucleic acid 120s attached to one or more of the second accessories. The first accessory can comprise the first accessory oligonucleotide 124ao1 and the first polymer covalently linked. The second accessory can comprise the second accessory oligonucleotide 124ao2 and the second polymer covalently linked.

In some embodiments, the first nucleic acid (e.g., a single-stranded DNA strand 104), the second nucleic acid (e.g., a scaffold 120s), the third nucleic acid (e.g., a carrier 120c), and/or the fourth nucleic acid (e.g., a nanoparticle 120n) comprises a third polymer. The first nucleic acid, the second nucleic acid, the third nucleic acid and/or the fourth nucleic acid each can comprise one or more third polymers. In some embodiments, the first nucleic acid, the second nucleic acid, the third nucleic acid and/or the fourth nucleic acid each comprises, or comprise about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, or a number or a range between any two of these values, third polymers. In some embodiments, the first nucleic acid, the second nucleic acid, the third nucleic acid and/or the fourth nucleic acid each comprises at least, comprises at least about, comprises at most, or comprises at most about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, third polymers.

In some embodiments, the polymer (e.g., the first polymer covalently linked to the first accessory oligonucleotide 124ao1 of the first adapter or the first accessory, or the second polymer covalently linked to the second accessory oligonucleotide 124ao1 of the second adapter or the second accessory, or the third polymer of the first nucleic acid, the second nucleic acid, the third nucleic acid, and/or the fourth nucleic acid) can be a homopolymer with one repeating unit. For example, the polymer can comprise a polystyrene As another example, the polymer can comprise poly(dimethylsiloxane). For example, the polymer can comprise polyethylene terephthalate. As another example, the polymer can comprise polyethylene glycol (PEG). In some embodiments, the polymer can be a heteropolymer (also known as a copolymer) with two or more different repeating units (such as 2, 3, 4, 5, 6, 7, 8, 9, 10, or more different repeating units). In some embodiments, a repeating unit of a polymer can have a n, the number of the repeating unit, of, or of about, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values.

In an example, a polymer used may include examples such as a poly(N-(5-azidoacetamidylpentyl)acrylamide-co-acrylamide), also known as PAZAM:

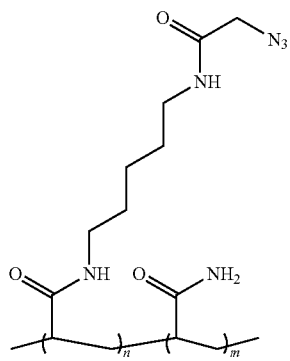

or

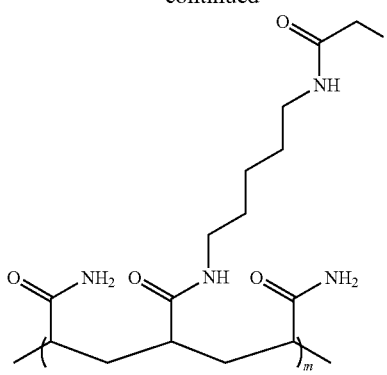

wherein n is an integer in the range of 1-20,000, and m is an integer in the range of 1-100,000

In some examples, the acrylamide monomer may include an azido acetamido pentyl acrylamide monomer:

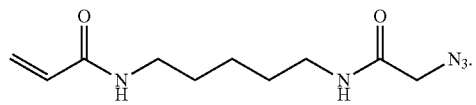 [SMILES: C=CC(=O)NCCCCCNC(=O)CN=[N+]=[N-]]

In some examples, the acrylamide monomer may include an N-isopropylacrylamide

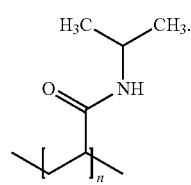

A "heteropolymer" is a large molecule of at least two different repeating subunits (monomers). An "acrylamide monomer" is a monomer with the structure

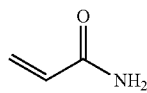

or a substituted analog thereof (e.g., methacrylamide or N-isopropylacrylamide). An example of a monomer including an acrylamide group and the azido group is azido acetamido pentyl acrylamide shown above. "Alkyl" refers to a straight or branched hydrocarbon chain that is fully saturated (i.e., contains no double or triple bonds). Example alkyl groups include methyl, ethyl, propyl, isopropyl, butyl, isobutyl, and tertiary butyl. As an example, the designation "$C_{1-4}$ alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

In an example, the polymer may be a heteropolymer, and the heteropolymer may include an acrylamide monomer, such as

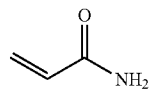

or a substituted analog thereof ("substituted" referring to the replacement of one or more hydrogen atoms in a specified group with another atom or group). In an example, the polymer is a heteropolymer and may further include an azido-containing acrylamide monomer. In some aspects, the heteropolymer includes:

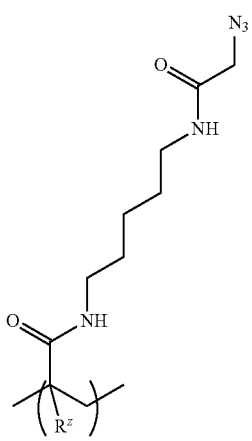

and optionally

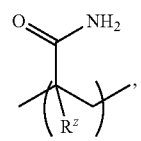

where each $R^z$ is independently H or $C_{1-4}$ alkyl.

In some aspects, the heteropolymer can include the structure:

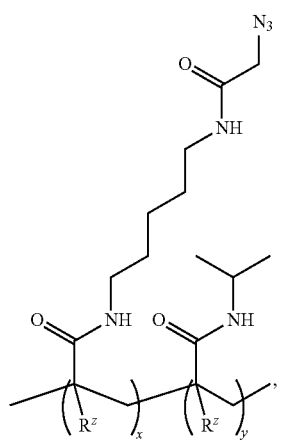

wherein x is an integer in the range of 1-20,000, and y is an integer in the range of 1-100,000, or

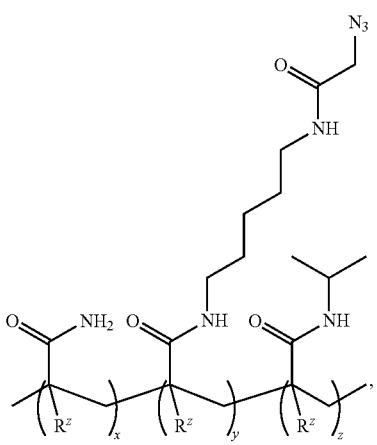

wherein y is an integer in the range of 1-20,000 and x and z are integers wherein the sum of x and z may be within a range of from 1 to 100,000, where each $R^z$ is independently H or $C_{1-4}$ alkyl and a ratio of x:y may be from approximately 10:90 to approximately 1:99, or may be approximately 5:95, or a ratio of (x:y):z may be from approximately 85:15 to approximately 95:5, or may be approximately 90:10 (wherein a ratio of x:(y:z) may be from approximately 1:(99) to approximately 10:(90), or may be approximately 5:(95)), respectively. In these examples, approximately means relative amounts of one may differ from amounts stated in the listed rations by up to 5%.

Nucleic Acid Products

Disclosed herein include embodiments of a second nucleic acid (e.g., a scaffold 120s) obtained by any method of modifying a nucleic acid of the present disclosure. Disclosed herein include embodiments of a third nucleic acid (e.g., a carrier 120c) obtained by any method of modifying a nucleic acid of the present disclosure. Disclosed herein include embodiments of a fourth nucleic acid (e.g., a nanoparticle 120n) obtained by any method of modifying a nucleic acid of the present disclosure.

Recombinant Terminal Deoxynucleotidyl Transferase Sequence

In some embodiments, the recombinant TdT comprises an amino acid sequence that is at least 85% identical to SEQ ID NO: 1. The recombinant TdT comprises an amino acid sequence that can be at least 90% identical to SEQ ID NO: 1. The recombinant TdT comprises an amino acid sequence that can be at least 95% identical to SEQ ID NO: 1. The recombinant TdT comprises an amino acid sequence that can be at least 95% identical to SEQ ID NO: 11. The recombinant TdT comprises an amino acid sequence that can be at least 80% identical to SEQ ID NO: 12.

In some embodiments, the recombinant TdT comprises an amino acid sequence that is, or is about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, identical to a bovine or *Bos taurus* TdT (e.g., SEQ ID NO: 12), or a fragment thereof (e.g., SEQ ID NO: 12). In some embodiments, the recombinant TdT comprises an amino acid sequence that is at least, at least about, at most or at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, identical to a bovine or *Bos taurus* TdT (e.g., SEQ ID NO: 12), or a fragment thereof (e.g., SEQ ID NO: 12). For example, the recombinant TdT comprises an amino acid sequence that is at least 85% identical to SEQ ID NO: 1. The recombinant TdT comprises an amino acid sequence that can be at least 90% identical to SEQ ID NO: 1. The recombinant TdT comprises an amino acid sequence that can be at least 95% identical to SEQ ID NO: 1.

In some embodiments, the recombinant TdT comprises an amino acid sequence with a sequence identity above a sequence identity threshold to a fragment of a bovine or *Bos taurus* TdT, such as amino acids 139-520 of *Bos taurus* TdT (e.g., SEQ ID NO: 1). FIG. 2 shows the sequence of amino acids 139-520 of *Bos taurus* TdT. For example, the recombinant terminal deoxynucleotidyl transferase (TdT) can comprise an amino acid sequence that is at least 80% identical to SEQ ID NO: 1. In some embodiments, the recombinant TdT comprises an amino acid sequence with a sequence identity above a sequence identity threshold to a variant of a bovine or *Bos taurus* TdT, or a variant of a bovine or *Bos taurus* TdT fragment (e.g., SEQ ID NO: 11). For example, the recombinant TdT can comprise an amino acid sequence that can be at least 95% identical to SEQ ID NO: 11.

Substitution Mutations

The recombinant TdT can comprise one or more amino acid substitution mutations at one or more positions functionally equivalent to Glu191, Lys193, Glu194, Asp242, Lys287, Phe296, Met299, Thr342, and His421 in the *Bos taurus* TdT (e.g., SEQ ID NO: 12). Each amino acid substitution mutation can be an amino acid substitution mutation to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

Each amino acid substitution mutation can be a substitution mutation to a nonpolar amino acid, a polar amino acid, a positively charged amino acid, a negatively charged amino acid, a hydrophobic amino acid, an aromatic amino acid, an aliphatic amino acid, a small amino acid, a hydrophilic amino acid, or a branched-chain amino acid. A nonpolar amino acid can be, for example, alanine, cysteine, glycine, isoleucine, leucine, methionine, phenylalanine, proline, tryptophan, or valine. A polar amino acid can be, for example, aspartic acid, glutamic acid, arginine, histidine, lysine, asparagine, glutamine, serine, threonine, or tyrosine. A polar amino acid can be, for example, an acidic polar amino acid, a basic polar amino acid, or a non-acidic non-basic polar amino acid. A basic polar amino acid or positively charged amino acid can be, for example, arginine, histidine, or lysine. An acidic amino acid or negatively charged amino acid can be, for example, aspartic acid or glutamic acid. A non-acidic non-basic amino acid can be, for example, asparagine, glutamine, serine, threonine, or tyrosine. A hydrophobic amino acid can be, for example, isoleucine, leucine, methionine, phenylalanine, tryptophan, tyrosine, or valine. An aromatic amino acid can be, for example, histidine, phenylalanine, tryptophan, or tyrosine. An aliphatic (non-aromatic) amino acid can be, for example, isoleucine, leucine, methionine, or valine. A small amino acid can be, for example, alanine, glycine, proline, or serine. A hydrophilic amino acid can be, for example, arginine, asparagine, aspartic acid, glutamine, glutamic acid, histidine, lysine, serine, or threonine. A branched-chain amino acid can be, for example, isoleucine, leucine, valine.

In some embodiments, the amino acid substitution mutation at the position functionally equivalent to Glu191 in the *Bos taurus* TdT of SEQ ID NO: 12 comprises a mutation to a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu191 can comprise a nonpolar amino acid, a hydrophobic amino acid, an aliphatic amino acid, or a branched-chain amino acid. The amino acid substitution mutation at the position functionally equivalent to Glu191 in the *Bos taurus* TdT of SEQ ID NO: 12 can be an amino acid substitution mutation to alanine, arginine, asparagine, aspartic acid, cysteine, glutamine, glycine, histidine, isoleucine, leucine, lysine, methionine, phenylalanine, proline, serine, threonine, tryptophan, tyrosine, or valine. The amino acid substitution mutation at the position functionally equivalent to Glu191 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Glu191 in the *Bos taurus* TdT of SEQ ID NO: 12 can be Glu191Ala, Glu191Arg, Glu191Asn, Glu191Asp, Glu191Cys, Glu191Gln, Glu191Gly, Glu191His, Glu191Ile, Glu191Leu, Glu191Lys, Glu191Met, Glu191Phe, Glu191Pro, Glu191Ser, Glu191Thr, Glu191Trp, Glu191Tyr, or Glu191Val. The amino acid substitution mutation at the position functionally equivalent to Glu191 in the *Bos taurus* TdT of SEQ ID NO: 12 can be Glu191Ala, Glu191Gly, Glu191Ile, Glu191Leu, Glu191Met, or Glu191Val. The amino acid substitution mutation at the position functionally equivalent to Glu191 in the *Bos taurus* TdT of SEQ ID NO: 12 can be Glu191Val. The recombinant TdT can comprise an amino acid sequence with a sequence identity above a sequence identity threshold to SEQ ID NO: 2.

In some embodiments, the amino acid substitution mutation at the position functionally equivalent to Lys193 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys193 in the *Bos taurus* TdT of SEQ ID NO: 12 can comprise a mutation to a polar amino acid or a hydrophilic amino acid. The amino acid substitution mutation at the position functionally equivalent to Lys193 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine. The amino acid substitution mutation at the position functionally equivalent to Lys193 in the *Bos taurus* TdT of SEQ ID NO: 12 can be an amino acid substitution mutation to asparagine, glutamine, serine, or threonine. The amino acid substitution mutation at the position functionally equivalent to Lys193 in the *Bos taurus* TdT of SEQ ID NO: 12 can be Lys193Ala, Lys193Arg, Lys193Asn, Lys193Asp, Lys193Cys, Lys193Gln, Lys193Glu, Lys193Gly, Lys193His, Lys193Ile, Lys193Leu, Lys193Met, Lys193Phe, Lys193Pro, Lys193Ser, Lys193Thr, Lys193Trp, Lys193Tyr, or Lys193Val. The amino acid substitution mutation at the position functionally equivalent to Lys193 in the *Bos taurus* TdT of SEQ ID NO: 12 can be Lys193Asn, Lys193Gln, Lys193Ser, or Lys193Thr. The amino acid substitution mutation at the position functionally equivalent to Lys193 in the *Bos taurus* TdT of SEQ ID NO: 12 can be Lys193Asn. The recombinant TdT can comprise an amino acid sequence with a sequence identity above a sequence identity threshold to SEQ ID NO: 3.

In some embodiments, the amino acid substitution mutation at the position functionally equivalent to Glu194 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Glu194 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Glu194 in the *Bos taurus* TdT of SEQ ID NO: 12 can be an amino acid substitution mutation to alanine, arginine, asparagine, aspartic acid, cysteine, glutamine, glycine, histidine, isoleucine, leucine, lysine, methionine, phenylalanine, proline, serine, threonine, tryptophan, tyrosine, or valine. The amino acid substitution mutation at the position functionally equivalent to Glu194 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Glu194 in the *Bos taurus* TdT of SEQ ID NO: 12 can be Glu194Ala, Glu194Arg, Glu194Asn, Glu194Asp, Glu194Cys, Glu194Gln, Glu194Gly, Glu194His, Glu194Ile, Glu194Leu, Glu194Lys, Glu194Met, Glu194Phe, Glu194Pro, Glu194Ser, Glu194Thr, Glu194Trp, Glu194Tyr, or Glu194Val. The amino acid substitution mutation at the position functionally equivalent to Glu194 in the *Bos taurus* TdT of SEQ ID NO: 12 can be Glu194Ala, Glu194Gly, Glu194Ile, Glu194Leu, Glu194Met, or Glu194Val. The amino acid substitution mutation at the position functionally equivalent to Glu194 in the *Bos taurus* TdT of SEQ ID NO: 12 can be Glu194Gly. The recombinant TdT can comprise an amino acid sequence with a sequence identity above a sequence identity threshold to SEQ ID NO: 4.

In some embodiments, the amino acid substitution mutation at the position functionally equivalent to Asp242 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Asp242 in the *Bos taurus* TdT of SEQ ID NO: 12 can comprise a mutation to a polar amino acid or an aromatic amino acid. The amino acid substitution mutation at the position functionally equivalent to Asp242 in the *Bos taurus* TdT of SEQ ID NO: 12 can be an amino acid substitution mutation to alanine, arginine, asparagine, cysteine, glutamine, glutamic acid, glycine, histidine, isoleucine, leucine, lysine, methionine, phenylalanine, proline, serine, threonine, tryptophan, tyrosine, or valine. The amino acid substitution mutation at the position functionally equivalent to Asp242 in the *Bos taurus* TdT of SEQ ID NO: 12 can be an amino acid substitution mutation to asparagine, glutamine, phenylalanine, serine, threonine, tryptophan, or tyrosine. The amino acid substitution mutation at the position functionally equivalent to Asp242 in the *Bos taurus* TdT of SEQ ID NO: 12 can be Asp242Ala, Asp242Arg, Asp242Asn, Asp242Cys, Asp242Gln, Asp242Glu, Asp242Gly, Asp242His, Asp242Ile, Asp242Leu, Asp242Lys, Asp242Met, Asp242Phe, Asp242Pro, Asp242Ser, Asp242Thr, Asp242Trp, Asp242Tyr, or Asp242Val. The amino acid substitution mutation at the position functionally equivalent to Asp242 in the *Bos taurus* TdT of SEQ ID NO: 12 can be Asp242Asn, Asp242Gln, Asp242Phe, Asp242Ser, Asp242Thr, Asp242Trp, or Asp242Tyr. The amino acid substitution mutation at the position functionally equivalent to Asp242 in the *Bos taurus* TdT of SEQ ID NO: 12 can be Asp242Tyr. The recombinant TdT can comprise an amino acid sequence with a sequence identity above a sequence identity threshold to SEQ ID NO: 5.

In some embodiments, the amino acid substitution mutation at the position functionally equivalent to Lys287 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Lys287 in the *Bos taurus* TdT of SEQ ID NO: 12 can comprise a mutation to a polar amino acid, a negatively charged amino acid or a hydrophilic amino acid. The amino acid substitution mutation at the position functionally equivalent to Lys287 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine. The amino acid substitution mutation at the position functionally equivalent to Lys287 in the *Bos taurus* TdT of SEQ ID NO: 12 can be an amino acid substitution mutation to aspartic acid or glutamic acid. The amino acid substitution mutation at the position functionally equivalent to Lys287 in the *Bos taurus* TdT of SEQ ID NO: 12 can be Lys287Ala, Lys287Arg, Lys287Asn, Lys287Asp, Lys287Cys, Lys287Gln, Lys287Glu, Lys287Gly, Lys287His, Lys287Ile, Lys287Leu, Lys287Met, Lys287Phe, Lys287Pro, Lys287Ser, Lys287Thr, Lys287Trp, Lys287Tyr, or Lys287Val. The amino acid substitution mutation at the position functionally equivalent to Lys287 in the *Bos taurus* TdT of SEQ ID NO: 12 can be Lys287Asp or Lys287Glu. The amino acid substitution mutation at the position functionally equivalent to Lys287 in the *Bos taurus* TdT of SEQ ID NO: 12 can be Lys287Glu. The recombinant TdT can comprise an amino acid sequence with a sequence identity above a sequence identity threshold to SEQ ID NO: 6.

In some embodiments, the amino acid substitution mutation at the position functionally equivalent to Phe296 in the *Bos taurus* TdT of SEQ ID NO: 12 comprises a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Phe296 in the *Bos taurus* TdT of SEQ ID NO: 12 can comprise a mutation to a nonpolar amino acid, a hydrophobic amino acid, an aliphatic amino acid, or a branched-chain amino acid. The amino acid substitution mutation at the position functionally equivalent to Phe296 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, methionine, proline, serine, threonine, tryptophan, tyrosine, or valine. The amino acid substitution mutation at the position functionally equivalent to Phe296 in the *Bos taurus* TdT of SEQ ID NO: 12 can be an amino acid substitution mutation to alanine, glycine, isoleucine, leucine, methionine, or valine. The amino acid substitution mutation at the position functionally equivalent to Phe296 in the *Bos taurus* TdT of SEQ ID NO: 12 can be Phe296Ala, Phe296Arg, Phe296Asn, Phe296Asp, Phe296Cys, Phe296Gln, Phe296Glu, Phe296Gly, Phe296His, Phe296Ile, Phe296Leu, Phe296Lys, Phe296Met, Phe296Pro, Phe296Ser, Phe296Thr, Phe296Trp, Phe296Tyr, or Phe296Val. The amino acid substitution mutation at the position functionally equivalent to Phe296 in the *Bos taurus* TdT of SEQ ID NO: 12 can be Phe296Ala, Phe296Gly, Phe296Ile, Phe296Leu, Phe296Met, or Phe296Val. The amino acid substitution mutation at the position functionally equivalent to Phe296 in the *Bos taurus* TdT of SEQ ID NO: 12 can be Phe296Leu. The recombinant TdT can comprise an amino acid sequence with a sequence identity above a sequence identity threshold to SEQ ID NO: 7.

In some embodiments, the amino acid substitution mutation at the position functionally equivalent to Met299 in the *Bos taurus* TdT of SEQ ID NO: 12 comprises a mutation to a polar amino acid, a positively charged amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Met299 in the *Bos taurus* TdT of SEQ ID NO: 12 can comprise a mutation to a polar amino acid, a positively charged amino acid, or a hydrophilic amino acid. The amino acid substitution mutation at the position functionally equivalent to Met299 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, phenylalanine, proline, serine, threonine, tryptophan, tyrosine, or valine. The amino acid substitution mutation at the position functionally equivalent to Met299 in the *Bos taurus* TdT of SEQ ID NO: 12 can be an amino acid substitution mutation to arginine, arginine, histidine, or lysine. The amino acid substitution mutation at the position functionally equivalent to Met299 in the *Bos taurus* TdT of SEQ ID NO: 12 can be Met299Ala, Met299Arg, Met299Asn, Met299Asp, Met299Cys, Met299Gln, Met299Glu, Met299Gly, Met299His, Met299Ile, Met299Leu, Met299Lys, Met299Phe, Met299Pro, Met299Ser, Met299Thr, Met299Trp, Met299Tyr, or Met299Val. The amino acid substitution mutation at the position functionally equivalent to Met299 in the *Bos taurus* TdT of SEQ ID NO: 12 can be Met299Arg, Met299His, or Met299Lys. The amino acid substitution mutation at the position functionally equivalent to Met299 in the *Bos taurus* TdT of SEQ ID NO: 12 can be Met299Lys. The recombinant TdT can comprise an amino acid sequence with a sequence identity above a sequence identity threshold to SEQ ID NO: 8.

In some embodiments, the amino acid substitution mutation at the position functionally equivalent to Thr342 in the *Bos taurus* TdT of SEQ ID NO: 12 comprises a mutation to a polar amino acid, an aliphatic amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to Thr342 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to Thr342 in the *Bos taurus* TdT of SEQ ID NO: 12 can be an amino acid substitution mutation to alanine, arginine, asparagine, aspartic acid, cysteine, glutamine, glutamic acid, glycine, histidine, isoleucine, leucine, lysine, methionine, phenylalanine, proline, serine, tryptophan, tyrosine, or valine. The amino acid substitution mutation at the position functionally equivalent to Thr342 in the *Bos taurus* TdT of SEQ ID NO: 12 can be an amino acid substitution mutation to asparagine, cysteine, glutamine, proline, or serine. The amino acid substitution mutation at the position functionally equivalent to Thr342 in the *Bos taurus* TdT of SEQ ID NO: 12 can be Thr342Ala, Thr342Arg, Thr342Asn, Thr342Asp, Thr342Cys, Thr342Gln, Thr342Glu, Thr342Gly, Thr342His, Thr342Ile, Thr342Leu, Thr342Lys, Thr342Met, Thr342Phe, Thr342Pro, Thr342Ser, Thr342Trp, Thr342Tyr, or Thr342Val. The amino acid substitution mutation at the position functionally equivalent to Thr342 in the *Bos taurus* TdT of SEQ ID NO: 12 can be Thr342Asn, Thr342Cys, Thr342Gln, Thr342Pro, or Thr342Ser. The amino acid substitution mutation at the position functionally equivalent to Thr342 in the *Bos taurus* TdT of SEQ ID NO: 12 can be Thr342Ser. The recombinant TdT can comprise an amino acid sequence with a sequence identity above a sequence identity threshold to SEQ ID NO: 9.

In some embodiments, the amino acid substitution mutation at the position functionally equivalent to His421 in the *Bos taurus* TdT of SEQ ID NO: 12 comprises a mutation to a polar amino acid, an aliphatic amino acid, or a hydrophilic amino acid. a mutation to a nonpolar amino acid, a polar amino acid, a positively charged amino acid, a negatively charged amino acid, a hydrophobic amino acid, an aromatic amino acid, an aliphatic amino acid, a small amino acid, or a hydrophilic amino acid. The amino acid substitution mutation at the position functionally equivalent to His421 in the *Bos taurus* TdT of SEQ ID NO: 12 can comprise a mutation to a polar amino acid, an aliphatic amino acid, or a hydrophilic amino acid. The amino acid substitution mutation at the position functionally equivalent to His421 in the *Bos taurus* TdT of SEQ ID NO: 12 can be an amino acid substitution mutation to alanine, arginine, asparagine, aspartic acid, cysteine, glutamine, glutamic acid, glycine, isoleucine, leucine, lysine, methionine, phenylalanine, proline, serine, threonine, tryptophan, tyrosine, or valine. The amino acid substitution mutation at the position functionally equivalent to His421 in the *Bos taurus* TdT of SEQ ID NO: 12 can be an amino acid substitution mutation to asparagine, cysteine, glutamine, proline, serine, or threonine. The amino acid substitution mutation at the position functionally equivalent to His421 in the *Bos taurus* TdT of SEQ ID NO: 12 can be His421Ala, His421Arg, His421Asn, His421Asp, His421Cys, His421Gln, His421Glu, His421Gly, His421Ile, His421Leu, His421Lys, His421Met, His421Phe, His421Pro, His421Ser, His421Thr, His421Trp, His421Tyr, or His421Val. The amino acid substitution mutation at the position functionally equivalent to His421 in the *Bos taurus* TdT of SEQ ID NO: 12 can be His421Asn, His421Cys, His421Gln, His421Pro, His421Ser, or His421Thr. The amino acid substitution mutation at the position functionally equivalent to His421 in the *Bos taurus* TdT of SEQ ID NO: 12 can be His421Pro. The recombinant TdT can comprise an amino acid sequence with a sequence identity above a sequence identity threshold to SEQ ID NO: 10.

In some embodiments, the recombinant TdT comprises two or more amino acid substitution mutations at two or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise three or more amino acid substitution mutations at three or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise four or more amino acid substitution mutations at four or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise five or more amino acid substitution mutations at five or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise six or more amino acid substitution mutations at six or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise seven or more amino acid substitution mutations at seven or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise eight or more amino acid substitution mutations at eight or more positions functionally equivalent to Glu191, Lys193, Glu194, Asp242, Lys287, Phe296, Met299, Thr342, and His421 in the *Bos taurus* TdT of SEQ ID NO: 12. The recombinant TdT can comprise eight amino acid substitution mutations at positions functionally equivalent to Glu191, Lys193, Glu194, Asp242, Lys287, Phe296, Met299, and His421 in the *Bos taurus* TdT of SEQ ID NO: 12. The recombinant TdT can comprise nine amino acid substitution mutations at positions functionally equivalent to Glu191, Lys193, Glu194, Asp242, Lys287, Phe296, Met299, Thr342, and His421 in the *Bos taurus* TdT of SEQ ID NO: 12.

In some embodiments, the two or more amino acid substitution mutations at the two or more positions functionally equivalent to Glu191, Lys193, Glu194, Asp242, Lys287, Phe296, Met299, Thr342, and His421 in the *Bos taurus* TdT of SEQ ID NO: 12 comprise two or more of Glu191Val, Lys193Asn, Glu194Gly, Asp242Tyr, Lys287Glu, Phe296Leu, Met299Lys, Thr342Ser, and His421Pro, respectively. The three or more amino acid substitution mutations at the three or more positions functionally equivalent to Glu191, Lys193, Glu194, Asp242, Lys287, Phe296, Met299, Thr342, and His421 in the *Bos taurus* TdT of SEQ ID NO: 12 can comprise three or more of Glu191Val, Lys193Asn, Glu194Gly, Asp242Tyr, Lys287Glu, Phe296Leu, Met299Lys, Thr342Ser, and His421Pro, respectively. The four or more amino acid substitution mutations at the four or more positions functionally equivalent to Glu191, Lys193, Glu194, Asp242, Lys287, Phe296, Met299, Thr342, and His421 in the *Bos taurus* TdT of SEQ ID NO: 12 can comprise four or more of Glu191Val, Lys193Asn, Glu194Gly, Asp242Tyr, Lys287Glu, Phe296Leu, Met299Lys, Thr342Ser, and His421Pro, respectively. The five or more amino acid substitution mutations at the five or more positions functionally equivalent to Glu191, Lys193, Glu194, Asp242, Lys287, Phe296, Met299, Thr342, and His421 in the *Bos taurus* TdT of SEQ ID NO: 12 can comprise five or more of Glu191Val, Lys193Asn, Glu194Gly, Asp242Tyr, Lys287Glu, Phe296Leu, Met299Lys, Thr342Ser, and His421Pro, respectively. The six or more amino acid substitution mutations at the six or more positions functionally equivalent to Glu191, Lys193, Glu194, Asp242, Lys287, Phe296, Met299, Thr342, and His421 in the *Bos taurus* TdT of SEQ ID NO: 12 can comprise six or more of Glu191Val, Lys193Asn, Glu194Gly, Asp242Tyr, Lys287Glu, Phe296Leu, Met299Lys, Thr342Ser, and His421Pro, respectively. The seven or more amino acid substitution mutations at the seven or more positions functionally equivalent to Glu191, Lys193, Glu194, Asp242, Lys287, Phe296, Met299, Thr342, and His421 in the *Bos taurus* TdT of SEQ ID NO: 12 can comprise seven or more of Glu191Val, Lys193Asn, Glu194Gly, Asp242Tyr, Lys287Glu, Phe296Leu, Met299Lys, Thr342Ser, and His421Pro, respectively. The eight or more amino acid substitution mutations at the eight or more positions functionally equivalent to Glu191, Lys193, Glu194, Asp242, Lys287, Phe296, Met299, Thr342, and His421 in the *Bos taurus* TdT of SEQ ID NO: 12 can comprise Glu191Val, Lys193Asn, Glu194Gly, Asp242Tyr, Lys287Glu, Phe296Leu, Met299Lys, Thr342Ser, and His421Pro, respectively. The eight amino acid substitution mutations at the positions functionally equivalent to Glu191, Lys193, Glu194, Asp242, Lys287, Phe296, Met299, and His421 in the *Bos taurus* TdT of SEQ ID NO: 12 can comprise Glu191Val, Lys193Asn, Glu194Gly, Asp242Tyr, Lys287Glu, Phe296Leu, Met299Lys, and His421Pro, respectively. The nine amino acid substitution mutations at the nine positions functionally equivalent to Glu191, Lys193, Glu194, Asp242, Lys287, Phe296, Met299, Thr342, and His421 in the *Bos taurus* TdT of SEQ ID NO: 12 can comprise Glu191Val, Lys193Asn, Glu194Gly, Asp242Tyr, Lys287Glu, Phe296Leu, Met299Lys, Thr342Ser, and His421Pro, respectively.

In some embodiments, the recombinant TdT comprises eight amino acid substitution mutations at eight positions functionally equivalent to Lys193, Glu194, Asp242, Lys287, Phe296, Met299, Thr342, and His421 in the *Bos taurus* TdT of SEQ ID NO: 12. The eight amino acid substitution mutations at the eight positions functionally equivalent to Lys193, Glu194, Asp242, Lys287, Phe296, Met299, Thr342, and His421 in the *Bos taurus* TdT of SEQ ID NO: 12 can be Lys193Asn, Glu194Gly, Asp242Tyr, Lys287Glu, Phe296Leu, Met299Lys, Thr342Ser, and His421Pro, respectively. In some embodiments, the recombinant TdT comprises nine amino acid substitution mutations at positions functionally equivalent to Glu191, Lys193, Glu194, Asp242, Lys287, Phe296, Met299, Thr342, and His421 in the *Bos taurus* TdT of SEQ ID NO: 12. The nine amino acid substitution mutations at the positions functionally equivalent to Glu191, Lys193, Glu194, Asp242, Lys287, Phe296, Met299, Thr342, and His421 in the *Bos taurus* TdT of SEQ ID NO: 12 can be Glu191Val, Lys193Asn, Glu194Gly, Asp242Tyr, Lys287Glu, Phe296Leu, Met299Lys, Thr342Ser, and His421Pro, respectively.

Thermal Stability

In some embodiments, the recombinant TdT is stable at a temperature of 47° C. or higher. The recombinant TdT can be stable at a temperature of 50° C. or higher. The recombinant TdT can be stable at a temperature of 55° C. or higher. The recombinant TdT can be stable at a temperature of 58° C. or higher.

The recombinant TdT can be thermally stable. The recombinant TdT can be stable at different temperatures in different embodiments. In some embodiments, the recombinant TdT can be stable at a temperature of, or of about, 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or higher. For example, the recombinant TdT can be stable at a temperature of 47° C. or higher. The recombinant TdT can be stable at a temperature of 50° C. or higher. The recombinant TdT can be stable at a temperature of 55° C. or higher. The recombinant TdT can be stable at a temperature of 58° C. or higher. The recombinant TdT can be stable at a temperature of at least, of at least about, of at most, or of at most about, 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values.

Activity

In some embodiments, the terminal deoxynucleotidyl transferase activity of the recombinant TdT is at least 80%, 85%, 90%, 95%, 100%, 105%, 110%, 115%, or 120%, of the terminal deoxynucleotidyl transferase activity of the *Bos taurus* TdT of SEQ ID NO: 12 at a same test temperature. The test temperature can be 37° C., 47° C., 50° C., 55° C., or 58° C.

The terminal deoxynucleotidyl transferase activity of the recombinant TdT can be higher than, or lower than, a bovine or *Bos taurus* TdT, or a fragment thereof. In some embodiments, the terminal deoxynucleotidyl transferase activity of the recombinant TdT is, or is about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%1, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, or more, of the terminal deoxynucleotidyl transferase activity of the *Bos taurus* TdT of SEQ ID NO: 12, or of the recombinant TdT of SEQ ID NO: 14, at a same test temperature. In some embodiments, the terminal deoxynucleotidyl transferase activity of the recombinant TdT is at least, is at least about, is at most, or is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 1430%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200%, or a number or a range between any two of these values, of the terminal deoxynucleotidyl transferase activity of the Bos taurus TdT of SEQ ID NO: 12, or the recombinant TdT of SEQ ID NO: 14, at a same test temperature. For example, the terminal deoxynucleotidyl transferase activity of the recombinant TdT can be, or be at least 80%, 85%, 90%, 95%, 100%, 105%, 110%, 115%, or 120%, of the terminal deoxynucleotidyl transferase activity of the Bos taurus TdT of SEQ ID NO: 12, or the recombinant TdT of SEQ ID NO: 14, at a same test temperature.

The test temperature can be different in different embodiments. In some embodiments, the test temperature is, or is about, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or higher. For example, the test temperature can be 37° C., 47° C., 50° C., 55° C., or 58° C. In some embodiments, the test temperature is at least, is at least about, is at most, or is at most about, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or a number or a range between any two of these values.

Additional Components

In some embodiments, the recombinant TdT comprises a small ubiquitin-like modifier (SUMO) fragment. The SUMO fragment comprises an amino acid sequence that can be at least 80% identical to SEQ ID NO: 13. The recombinant TdT can comprise the SUMO fragment on the N-terminus of the recombinant TdT. The recombinant TdT can comprise an amino acid sequence that is at least 80% identical to SEQ ID NO: 14. The recombinant TdT can comprise an amino acid sequence that is at least 80% identical to SEQ ID NO: 15. The recombinant TdT can comprise the SUMO fragment on the C-terminus of the recombinant TdT.

In some embodiments, the recombinant TdT comprises a tag for purification, such as a His-tag or a glutathione S-transferase. The tag for purification can be on the N-terminal of the recombinant TdT, on the C-terminal of the recombinant TdT, or internal to the recombinant TdT. The recombinant TdT can comprise a protease cleavage sequence, such as LeuValProArg/GlySer (a thrombin cleavage site) or LeuGluValLeuPheGln/GlyPro (a PreScission Protease cleavage site) between the tag for purification and another component (e.g., a Bos taurus TdT fragment) or the rest of the recombinant TdT.

In some embodiments, the recombinant TdT comprises a small ubiquitin-like modifier (SUMO) protein, or a fragment thereof. The sequence of the SUMO protein, or a fragment thereof, in the recombinant TdT can be different in different embodiments. In some embodiments, the SUMO protein, or a fragment thereof, in the recombinant TdT comprises an amino acid sequence that is, or about, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 9900 or 100%, identical to a SUMO protein (e.g., suppressor of mif two 3, SMT3, in yeast), or a fragment thereof (e.g., a SUMO fragment comprising an amino sequence of SEQ ID NO 13) For example, the SUMO fragment in the recombinant TdT can comprise an amino acid sequence that is at least 80% identical to SEQ ID NO: 13. In some embodiments, the SUMO protein, or a fragment thereof, in the recombinant TdT comprises an amino acid sequence that is at least, is at least about, is at most, or is at most about, 51%, 52%, 53%, 54%, 55%, 56%, 57%, 58%, 59%, 60%, 61%, 60%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97% 98%, 99%, or 100%, identical to a SUMO protein (e.g., suppressor of mif two 3, SMT3, in yeast), or a fragment thereof (e.g., a SUMO fragment comprising an amino acid sequence of SEQ ID NO: 13).

The location of the SUMO fragment in the recombinant TdT can be different in different embodiments. In some embodiments, the recombinant TdT comprises the SUMO fragment on the N-terminus of the recombinant TdT. In some embodiments, the recombinant TdT comprises the SUMO fragment on the C-terminus of the recombinant TdT.

The recombinant TdT can comprise an amino acid sequence with a sequence identity of, or of about, a sequence identity threshold to a recombinant TdT comprising a SUMO fragment (e.g., a recombinant TdT with a SUMO fragment comprising an amino acid sequence of SEQ ID NO: 14, or SEQ ID NO: 15). The recombinant TdT can comprise an amino acid sequence with a sequence identity above, above about, below, or below about, a sequence identity threshold to a recombinant TdT comprising a SUMO fragment (e.g., SEQ ID NO: 14, or SEQ ID NO: 15). The recombinant TdT can comprise an amino acid sequence with a sequence identity of at least, at least about, at most, or at most about, a sequence identity threshold to a recombinant TdT comprising a SUMO fragment (e.g., SEQ ID NO: 14, or SEQ ID NO: 15). The sequence identity threshold can be different in different embodiments. In some embodiments, the sequence identity threshold is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the recombinant T an comprise an amino acid sequence that is at least 80% identical to SEQ ID NO: 14. As another example, the recombinant TdT can comprise an amino acid sequence that is at least 80% identical to SEQ ID NO: 15.

Sequencing
Library Preparation

Libraries comprising polynucleotides may be prepared in any suitable manner to attach oligonucleotide adapters to target polynucleotides. As used herein, a "library" is a population of polynucleotides from a given source or sample. A library comprises a plurality of target polynucleotides. As used herein, a "target polynucleotide" is a polynucleotide that is desired to sequence. The target polynucleotide may be essentially any polynucleotide of known or unknown sequence. It may be, for example, a fragment of genomic DNA or cDNA. Sequencing may result in determination of the sequence of the whole, or a part of the target polynucleotides. The target polynucleotides may be derived from a primary polynucleotide sample that has been randomly fragmented. The target polynucleotides may be processed into templates suitable for amplification by the placement of universal primer sequences at the ends of each target fragment. The target polynucleotides may also be obtained from a primary RNA sample by reverse transcription into cDNA.

As used herein, the terms "polynucleotide" and "oligonucleotide" may be used interchangeably and refer to a molecule comprising two or more nucleotide monomers covalently bound to one another, typically through a phosphodiester bond. Polynucleotides typically contain more nucleotides than oligonucleotides. For purposes of illustration and not limitation, a polynucleotide may be considered to contain 15, 20, 30, 40, 50, 100, 200, 300, 400, 500, or more nucleotides, while an oligonucleotide may be considered to contain 100, 50, 20, 15 or less nucleotides.

Polynucleotides and oligonucleotides may comprise deoxyribonucleic acid (DNA) or ribonucleic acid (RNA). The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

Primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs using standard techniques well known in the art. The precise sequence of primary polynucleotides is generally not material to the disclosure presented herein, and may be known or unknown.

In some embodiments, the primary target polynucleotides are RNA molecules. In an aspect of such embodiments, RNA isolated from specific samples is first converted to double-stranded DNA using techniques known in the art. The double-stranded DNA may then be index tagged with a library specific tag. Different preparations of such double-stranded DNA comprising library specific index tags may be generated, in parallel, from RNA isolated from different sources or samples. Subsequently, different preparations of double-stranded DNA comprising different library specific index tags may be mixed, sequenced en masse, and the identity of each sequenced fragment determined with respect to the library from which it was isolated/derived by virtue of the presence of a library specific index tag sequence.

In some embodiments, the primary target polynucleotides are DNA molecules. For example, the primary polynucleotides may represent the entire genetic complement of an organism, and are genomic DNA molecules, such as human DNA molecules, which include both intron and exon sequences (coding sequence), as well as non-coding regulatory sequences such as promoter and enhancer sequences. Although it could be envisaged that particular sub-sets of polynucleotide sequences or genomic DNA could also be used, such as, for example, particular chromosomes or a portion thereof. In many embodiments, the sequence of the primary polynucleotides is not known. The DNA target polynucleotides may be treated chemically or enzymatically either prior to, or subsequent to a fragmentation processes, such as a random fragmentation process, and prior to, during, or subsequent to the ligation of the adapter oligonucleotides.

Preferably, the primary target polynucleotides are fragmented to appropriate lengths suitable for sequencing. The target polynucleotides may be fragmented in any suitable manner. Preferably, the target polynucleotides are randomly fragmented. Random fragmentation refers to the fragmentation of a polynucleotide in a non-ordered fashion by, for example, enzymatic, chemical or mechanical means. Such fragmentation methods are known in the art and utilize standard methods (Sambrook and Russell, Molecular Cloning, A Laboratory Manual, third edition). For the sake of clarity, generating smaller fragments of a larger piece of polynucleotide via specific PCR amplification of such smaller fragments is not equivalent to fragmenting the larger piece of polynucleotide because the larger piece of polynucleotide remains in intact (i.e., is not fragmented by the PCR amplification). Moreover, random fragmentation is designed to produce fragments irrespective of the sequence identity or position of nucleotides comprising and/or surrounding the break.

In some embodiments, the random fragmentation is by mechanical means such as nebulization or sonication to produce fragments of about 50 base pairs in length to about 1500 base pairs in length, such as 50-700 base pairs in length or 50-500 base pairs in length.

Fragmentation of polynucleotide molecules by mechanical means (nebulization, sonication and Hydroshear for example) may result in fragments with a heterogeneous mix of blunt and 3'- and 5'-overhanging ends. Fragment ends may be repaired using methods or kits (such as the Lucigen DNA terminator End Repair Kit) known in the art to generate ends that are optimal for insertion, for example, into blunt sites of cloning vectors. In some embodiments, the fragment ends of the population of nucleic acids are blunt ended. The fragment ends may be blunt ended and phosphorylated. The phosphate moiety may be introduced via enzymatic treatment, for example, using polynucleotide kinase.

In some embodiments, the target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes may be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, while the adapter polynucleotide construct could be a T-construct with a compatible 'T' overhang present on the 3' terminus of each duplex region of the adapter construct. This end modification also prevents self-ligation of the target polynucleotides such that there is a bias towards formation of the combined ligated adapter-target polynucleotides.

In some embodiments, fragmentation is accomplished through tagmentation as described in, for example, International Patent Application Publication WO 2016/130704. In such methods transposases are employed to fragment a double stranded polynucleotide and attach a universal primer sequence into one strand of the double stranded polynucleotide. The resulting molecule may be gap-filled and subject to extension, for example by PCR amplification, using primers that comprise a 3' end having a sequence complementary to the attached universal primer sequence and a 5' end that contains other sequences of an adapter.

The adapters may be attached to the target polynucleotide in any other suitable manner. In some embodiments, the adapters are introduced in a multi-step process, such as a two-step process, involving ligation of a portion of the adapter to the target polynucleotide having a universal primer sequence. The second step comprises extension, for example by PCR amplification, using primers that comprise a 3' end having a sequence complementary to the attached universal primer sequence and a 5' end that contains other sequences of an adapter. By way of example, such extension may be performed as described in U.S. Pat. No. 8,053,192. Additional extensions may be performed to provide additional sequences to the 5' end of the resulting previously extended polynucleotide.

In some embodiments, the entire adapter is ligated to the fragmented target polynucleotide. Preferably, the ligated adapter comprises a double stranded region that is ligated to a double stranded target polynucleotide. Preferably, the double-stranded region is as short as possible without loss of function. In this context, "function" refers to the ability of the double-stranded region to form a stable duplex under standard reaction conditions. In some embodiments, standard reactions conditions refer to reaction conditions for an enzyme-catalyzed polynucleotide ligation reaction, which will be well known to the skilled reader (e.g. incubation at a temperature in the range of 4° C. to 25° C. in a ligation buffer appropriate for the enzyme), such that the two strands forming the adapter remain partially annealed during ligation of the adapter to a target molecule. Ligation methods are known in the art and may utilize standard methods (Sambrook and Russell, Molecular Cloning, A Laboratory Manual, third edition). Such methods utilize ligase enzymes such as DNA ligase to effect or catalyze joining of the ends of the two polynucleotide strands of, in this case, the adapter duplex oligonucleotide and the target polynucleotide duplexes, such that covalent linkages are formed. The adapter duplex oligonucleotide may contain a 5'-phosphate moiety in order to facilitate ligation to a target polynucleotide 3'-OH. The target polynucleotide may contain a 5'-phosphate moiety, either residual from the shearing process, or added using an enzymatic treatment step, and has been end repaired, and optionally extended by an overhanging base or bases, to give a 3'-OH suitable for ligation. In this context, attaching means covalent linkage of polynucleotide strands which were not previously covalently linked. In a particular aspect of the invention, such attaching takes place by formation of a phosphodiester linkage between the two polynucleotide strands, but other means of covalent linkage (e.g. non-phosphodiester backbone linkages) may be used. Ligation of adapters to target polynucleotides is described in more detail in, for example, U.S. Pat. No. 8,053,192.

Any suitable adapter may be attached to a target polynucleotide via any suitable process, such as those discussed above. The adapter includes a library-specific index tag sequence. The index tag sequence may be attached to the target polynucleotides from each library before the sample is immobilized for sequencing. The index tag is not itself formed by part of the target polynucleotide, but becomes part of the template for amplification. The index tag may be a synthetic sequence of nucleotides which is added to the target as part of the template preparation step. Accordingly, a library-specific index tag is a nucleic acid sequence tag which is attached to each of the target molecules of a particular library, the presence of which is indicative of or is used to identify the library from which the target molecules were isolated.

Preferably, the index tag sequence is 20 nucleotides or less in length. For example, the index tag sequence may be 1-10 nucleotides or 4-6 nucleotides in length. A four-nucleotide index tag gives a possibility of multiplexing 256 samples on the same array, a six base index tag enables 4,096 samples to be processed on the same array.

The adapters may contain more than one index tag so that the multiplexing possibilities may be increased.

The adapters preferably comprise a double stranded region and a region comprising two non-complementary single strands. The double-stranded region of the adapter may be of any suitable number of base pairs. Preferably, the double stranded region is a short double-stranded region, typically comprising 5 or more consecutive base pairs, formed by annealing of two partially complementary polynucleotide strands. This "double-stranded region" of the adapter refers to a region in which the two strands are annealed and does not imply any particular structural conformation. In some embodiments, the double stranded region comprises 20 or less consecutive base pairs, such as 10 or less or 5 or less consecutive base pairs.

The stability of the double-stranded region may be increased, and hence its length potentially reduced, by the inclusion of non-natural nucleotides which exhibit stronger base-pairing than standard Watson-Crick base pairs. Preferably, the two strands of the adapter are 100% complementary in the double-stranded region.

When the adapter is attached to the target polynucleotide, the non-complementary single stranded region may form the 5' and 3' ends of the polynucleotide to be sequenced. The term "non-complementary single stranded region" refers to a region of the adapter where the sequences of the two polynucleotide strands forming the adapter exhibit a degree of non-complementarity such that the two strands are not capable of fully annealing to each other under standard annealing conditions for a PCR reaction.

The non-complementary single stranded region is provided by different portions of the same two polynucleotide strands which form the double-stranded region. The lower limit on the length of the single-stranded portion will typically be determined by function of, for example, providing a suitable sequence for binding of a primer for primer extension, PCR and/or sequencing. Theoretically there is no upper limit on the length of the unmatched region, except that in general it is advantageous to minimize the overall length of the adapter, for example, in order to facilitate separation of unbound adapters from adapter-target constructs following the attachment step or steps. Therefore, it is generally preferred that the non-complementary single-stranded region of the adapter is 50 or less consecutive nucleotides in length, such as 40 or less, 30 or less, or 25 or less consecutive nucleotides in length.

The library-specific index tag sequence may be located in a single-stranded, double-stranded region, or span the single-stranded and double-stranded regions of the adapter. Preferably, the index tag sequence is in a single-stranded region of the adapter.

The adapters may include any other suitable sequence in addition to the index tag sequence. For example, the adapters may comprise universal extension primer sequences, which are typically located at the 5' or 3' end of the adapter and the resulting polynucleotide for sequencing. The universal extension primer sequences may hybridize to complementary primers bound to a surface of a solid substrate. The complementary primers comprise a free 3' end from which a polymerase or other suitable enzyme may add nucleotides to extend the sequence using the hybridized library polynucleotide as a template, resulting in a reverse strand of the library polynucleotide being coupled to the solid surface. Such extension may be part of a sequencing run or cluster amplification.

In some embodiments, the adapters comprise one or more universal sequencing primer sequences. The universal sequencing primer sequences may bind to sequencing primers to allow sequencing of an index tag sequence, a target sequence, or an index tag sequence and a target sequence.

The precise nucleotide sequence of the adapters is generally not material to the invention and may be selected by the user such that the desired sequence elements are ultimately included in the common sequences of the library of templates derived from the adapters to, for example, provide binding sites for particular sets of universal extension primers and/or sequencing primers.

The adapter oligonucleotides may contain exonuclease resistant modifications such as phosphorothioate linkages.

Preferably, the adapter is attached to both ends of a target polypeptide to produce a polynucleotide having a first adapter-target-second adapter sequence of nucleotides. The first and second adapters may be the same or different. Preferably, the first and second adapters are the same. If the first and second adapters are different, at least one of the first and second adapters comprises a library-specific index tag sequence.

It will be understood that a "first adapter-target-second adapter sequence" or an "adapter-target-adapter" sequence refers to the orientation of the adapters relative to one another and to the target and does not necessarily mean that the sequence may not include additional sequences, such as linker sequences, for example.

Other libraries may be prepared in a similar manner, each including at least one library-specific index tag sequence or combinations of index tag sequences different than an index tag sequence or combination of index tag sequences from the other libraries.

As used herein, "attached" or "bound" are used interchangeably in the context of an adapter relative to a target sequence. As described above, any suitable process may be used to attach an adapter to a target polynucleotide. For example, the adapter may be attached to the target through ligation with a ligase; through a combination of ligation of a portion of an adapter and addition of further or remaining portions of the adapter through extension, such as PCR, with primers containing the further or remaining portions of the adapters; trough transposition to incorporate a portion of an adapter and addition of further or remaining portions of the adapter through extension, such as PCR, with primers containing the further or remaining portions of the adapters; or the like. Preferably, the attached adapter oligonucleotide is covalently bound to the target polynucleotide.

After the adapters are attached to the target polynucleotides, the resulting polynucleotides may be subjected to a clean-up process to enhance the purity to the adapter-target-adapter polynucleotides by removing at least a portion of the unincorporated adapters. Any suitable clean-up process may be used, such as electrophoresis, size exclusion chromatography, or the like. In some embodiments, solid phase reverse immobilization (SPRI) paramagnetic beads may be employed to separate the adapter-target-adapter polynucleotides from the unattached adapters. While such processes may enhance the purity of the resulting adapter-target-adapter polynucleotides, some unattached adapter oligonucleotides likely remain.

Preparation of Immobilized Samples for Sequencing

The plurality of adapter-target-adapter molecules from one or more sources are then immobilized and amplified prior to sequencing. Methods for attaching adapter-target-adapter molecules from one or more sources to a substrate are known in the art. Likewise, methods for amplifying immobilized adapter-target-adapter molecules include, but are not limited to, bridge amplification and kinetic exclusion amplification. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A sample, including pooled samples, can then be immobilized in preparation for sequencing. Sequencing can be performed as an array of single molecules, or can be amplified prior to sequencing. The amplification can be carried out using one or more immobilized primers. The immobilized primer(s) can be a lawn on a planar surface, or on a pool of beads. The pool of beads can be isolated into an emulsion with a single bead in each "compartment" of the emulsion. At a concentration of only one template per "compartment", only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813, each of which is incorporated herein by reference in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

Although the invention encompasses "solid-phase" amplification methods in which only one amplification primer is immobilized (the other primer usually being present in free solution), it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example, one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in WO 05/065814.

Certain embodiments of the invention may make use of solid supports comprised of an inert substrate or matrix (e.g. glass slides, polymer beads, etc.) which has been "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of templates prepared according to the first, second or third aspects of the invention is used to prepare clustered arrays of nucleic acid colonies, analogous to those described in U.S. Pub. No. 2005/0100900, U.S. Pat. No. 7,115,400, WO 00/18957 and WO 98/44151, the contents of which are incorporated herein by reference in their entirety, by solid-phase amplification and more particularly solid phase isothermal amplification. The terms 'cluster' and 'colony' are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term "solid phase", or "surface", is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420, which are incorporated herein by reference in their entirety. Due to the lower temperatures required in the isothermal process, this is particularly preferred.

It will be appreciated that any of the amplification methodologies described herein or generally known in the art may be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence-based amplification (NASBA), as described in U.S. Pat. No. 8,003,354, which is incorporated herein by reference in its entirety. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, CA) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., Proc. Natd. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455, 166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670, 810, which is incorporated herein by reference in its entirety.

Another polynucleotide amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed, and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

Use in Sequencing

Following attachment of adaptor-target-adaptor molecules to a surface, the sequence of the immobilized and amplified adapter-target-adapter molecules is determined. Sequencing can be carried out using any suitable sequencing technique, and methods for determining the sequence of immobilized and amplified adapter-target-adapter molecules, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." *Science* 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluorophores can include fluorophores linked to the ribose moiety via a 3' ester linkage (Metzker, *Genome Res.* 15:1767-1776 (2005), which is incorporated herein by reference). Other approaches have separated the terminator chemistry from the cleavage of the fluorescence label (Ruparel et al., *Proc Natl Acad Sci USA* 102: 5932-7 (2005), which is incorporated herein by reference in its entirety). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251, the disclosures of which are incorporated herein by reference in their entireties.

Some embodiments can utilize detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis", *Acc. Chem. Res.* 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, both of which are incorporated herein by reference, or nucleotide incorporations can be detected with zero-mode waveguides as described, for example, in U.S. Pat. No. 7,315,019, which is incorporated herein by reference, and using fluorescent nucleotide analogs and engineered polymerases as described, for example, in U.S. Pat. No. 7,405,281 and U.S. Pub. No. 2008/0108082, both of which are incorporated herein by reference. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617, all of which are incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly, the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

EXAMPLES

Some aspects of the embodiments discussed above are disclosed in further detail in the following examples, which are not in any way intended to limit the scope of the present disclosure.

Example 1

Evolving a Thermostable Terminal Deoxynucleotidyl Transferase

This example demonstrates evolving a thermostable terminal deoxynucleotidyl transferase by random mutagenesis and combining mutations identified. After screening about 10,000 TdT mutants, TdT3-2 which was 10° C. more thermostable than SUMO-TdT, while preserving the catalytic properties, was found.

Mutant libraries were generated via random mutagenesis. The first mutant library used SUMO-TdT as the parent template. SUMO-TdT in this disclosure refers to a recombinant TdT that contains amino acids 139-520 of a bovine (Bos taurus) TdT and an N-terminal SUMO-tag which improves solubility and expression. Table 1 shows the sequence of a SUMO-TdT. FIG. 2 shows a non-limiting exemplary sequence alignment of SUMO-TdT (SEQ ID NO: 14) with amino acids 139-520 (SEQ ID NO: 1) of Bos taurus TdT (SEQ ID NO: 12). A library of 2790 mutants was screened with heat treatment at 47° C. for 1 min. This round identified thermostable mutants TdT1-1 and TdT1-2 as thermostable (Tables 2A and 2B). TdT1-1 and TdT1-2 have significantly higher FRET readout without and with heat treatment as compared to SUMO-TdT. Also, TdT1-1 and TdT1-2 retained a larger proportion of their activity after heat treatment.

TABLE 1

Amino acid sequences of SUMO-TdT (bovine) and TdT3-2. The four underlined sequences in the SUMO-TdT (bovine) sequence are a His tag, a thrombin cleavage site, a SUMO fragment, and a bovine TdT fragment of amino acids 139-520. The four underlined sequences in the TdT3-2 sequence are a His tag, a thrombin cleavage site, a SUMO fragment, and a bovine TdT fragment of amino acids 139-520 with eight substitution mutations (E175V, K177N, E178G, D226Y, K271E, F280L, M283K, and H405P).

| Construct | Amino acid sequence |
|---|---|
| SUMO-TdT | MGSSHHHHHHGSGLVPRGSASMSDSEVNQEAKPEVKPEV KPETHINLKVSDGSSEIFFKIKKTTPLRRLMEAFAKRQG KEMDSLRFLYDGIRIQADQTPEDLDMEDNDIIEAHREQI GGELMRTDYSATPNPGFQKTPPLAVKKISQYACQRKTTL NNYNHIFTDAFEILAENSEFKENEVSYVTFMRAASVLKS LPFTIISMKDTEGIPCLGDKVKCIIEEIIEDGESSEVKA VLNDERYQSFKLFTSVFGVGLKTSEKWFRMGFRSLSKIM SDKTLKFTKMQKAGFLYYEDLVSCVTRAEAEAVGVLVKE AVWAFLPDAFVTMTGGFRRGKKIGHDVDFLITSPGSAED EEQLLPKVINLWEKKGLLLYYDLVESTFEKFKLPSRQVD TLDHFQKCFLILKLHHQRVDSSKSNQQEGKTWKAIRVDL VMCPYENRAFALLGWTGSRQFERDIRRYATHERKMMLDN HALYDKTKRVFLKAESEEEIFAHLGLDYIEPWERNA (SEQ ID NO: 14) |
| TdT3-2 | MGSSHHHHHHGSGLVPRGSASMSDSEVNQEAKPEVKPEV KPETHINLKVSDGSSEIFFKIKKTTPLRRLMEAFAKRQG KEMDSLRFLYDGIRIQADQTPEDLDMEDNDITEAHREQI GGELMRTDYSATPNPGFQKTPPLAVKKISQYACQRKTTL NNYNHIFTDAFEILAENSVFNGNEVSYVTFMRAASVLKS LPFTIISMKDTEGIPCLGDKVKCIIEEIIEYGESSEVKA VLNDERYQSFKLFTSVFGVGLKTSEKWFRMGFRSLSEIM SDKTLKLTKKQKAGFLYYEDLVSCVTRAEAEAVGVLVKE AVWAFLPDAFVTMTGGFRRGKKIGHDVDFLITSPGSAED EEQLLPKVINLWEKKGLLLYYDLVESTFEKFKLPSRQVD TLDHFQKCFLILKLPHQRVDSSKSNQQEGKTWKAIRVDL VMCPYENRAFALLGWTGSRQFERDIRRYATHERKMMLDN HALYDKTKRVFLKAESEEEIFAHLGLDYIEPWERNA (SEQ ID NO: 15) |

TABLE 2A

Summary table of TdT variants from thermostability screen. The positions of the substitution mutations are the positions in the SUMO-TdT (and TdT variants thereof). See FIG. 2 for the positions of the substitution mutations in SUMO-TdT (and TdT variants thereof) and corresponding positions in Bos taurus TdT.

| Screening Round | Temperature[d] (° C.) | Parent template[g] | Library size | Positive TdT variants[e] | Mutations[f] |
|---|---|---|---|---|---|
| 1[a] | 47 | SUMO-TdT | 2790 | TdT1-1 | E175V |
|  |  |  |  | TdT1-2 | D226Y |
| 2[b] | 50 | TdT1-1 | 7636 | TdT2-1 | M283K |
|  |  |  |  | TdT2-2 | K271E, T326S |
|  |  |  |  | TdT2-3 | E178G, F280L, H405P |
|  |  |  |  | TdT2-4 | K177N |
| 3[c] | 55 | TdT1-1 | 736 | TdT3-1 | K177N, E178G, K271E, F280L, M283K |
|  | 58 | TdT1-3[h] | 736 | TdT3-2 | K177N, E178G, K271E, F280L, M283K, H405P |

[a]Mutant library for Round 1 was created by random mutagenesis via error-prone PCR
[b]Mutant library for Round 2 was created by random mutagenesis via error-prone PCR
[c]Mutant library for Round 3 were created by combining the mutations identified from TdT2-1, TdT2-2, TdT2-3 and TdT2-4
[d]Temperature that crude cell lysate was subjected to during the screen
[e]Positive TdT variants identified from each rounds of screening
[f]Mutations found in positive TdT variants in e when compared to parent template stated in g
[h]TdT3-1 is derived from the combination of mutations E175V and D226Y from TdT1-1 and TdT1-2

TABLE 2B

Summary table of TdT variants from thermostability screen. Some mutants discovered from round 1, round 2 and round 3 are shown. Some mutations discovered from round 1 and round 2 are shown in the left-hand side column. No mutations are listed for round 3 because round 3 did not generate new mutations; round 3 mutants were generated by recombining round 2 mutations from different mutants. A checked box indicates the presence of the particular mutation from the left-hand side column in that mutant. The lowest row "Others" indicates mutations that occur serendipitously in round 2 (Del in an area not targeted for mutagenesis) or round 3. The positions of the substitution mutations are the positions in the SUMO-TdT (and TdT variants thereof).

| | | Round 1 | | Round 2 | | | | Round 3 | | |
|---|---|---|---|---|---|---|---|---|---|---|
| | Mutations | C44 (TdT1-1) | C67 (TdT1-2) | M3 (TdT2-1) | M5 (TdT2-2) | M10 (TdT2-3) | M11 (TdT2-4) | CM1 (TdT3-1) | CM2 | CM3 |
| Round 1 | E175V | X | | X | X | X | X | X | X | X |
| | D226Y | | X | | | | | | | |
| Round 2 | K177N | | | | | | X | X | X | X |
| | E178G | | | | | X | | X | X | X |
| | K271E | | | | X | | | X | X | X |
| | F280L | | | | | X | | X | X | |
| | M283K | | | X | | | | X | X | X |
| | T326S | | | | X | | | | | |
| | H405P | | | | | X | | | X | |
| | Others | | | Del. 18G | | | | | | M81I |

| | | Mutants Round 3 | | | | | | | |
|---|---|---|---|---|---|---|---|---|---|
| | Mutations | CM5 | CM12 (TdT3-2) | CM14 | CM15 | CM16 | CM19 | CM20 | CM24 | CM25 |
| Round 1 | E175V | X | X | X | X | X | X | X | X | X |
| | D226Y | | X | X | X | X | X | X | X | X |
| Round 2 | K177N | X | X | X | X | X | X | X | X | X |
| | E178G | X | X | X | X | X | | X | X | X |
| | K271E | X | X | X | X | X | X | X | X | X |
| | F280L | | X | X | | X | X | X | X | |
| | M283K | X | X | X | X | X | X | X | | X |
| | T326S | | | | X | | | | | |
| | H405P | | X | | | X | | | | X |
| | Others | | | | | N361K | K233G | | | |

For the second round of screening, a library size of 7636 was generated using TdT1-1 as parent. TdT1-1 was selected as the parent template as TdT1-1 had higher FRET readout without heat treatment as compared to TdT1-2. The FRET readout of a TdT mutant indicated the enzymatic activity of the TdT mutant. The second round of screening was conducted with heat treatment of 50° C. for 1 min and four thermostable mutants were identified (TdT2-1, TdT2-2, TdT2-3, TdT2-4) (Tables 2A and 2B). The four mutants have significantly higher FRET readouts than TdT1-1 under both no heat treatment and heat treatment conditions. All four mutants also retained much higher proportion of their activity after being subjected to 50° C. for 1 min.

A combination of mutations identified from TdT2-1, TdT2-2, TdT2-3 and TdT2-4 was speculated to give a synergistic increase in thermostability. For the third round of the thermostability screen, two mutant libraries were generated. One of the mutant libraries was based on TdT1-1 template with different combinations of the mutations found in TdT2-1, TdT2-2, TdT2-3 and TdT2-4. The other mutant library was created similarly, except utilizing TdT1-3 as the parent template. TdT1-3 comprised of a combination of mutations in TdT1-1 and TdT1-2 (Tables 2A and 2B). The TdT1-1-based mutant library was screened with a 1 min heat shock at 55° C. TdT3-1, which was identified as the top mutant from this library (Tables 2A and 2B), had a much higher FRET readout both without and with heat-shock, and retained a higher fraction of its FRET activity after heat-shock. Screening of the TdT1-3-based mutant library with heat treatment at 58° C. for 1 min led to the discovery of TdT3-2 with significantly higher FRET readout under both room temperature and heat-shock treatment (Tables 2A and 2B). TdT3-2 retained at least half of its FRET activity after being subjected to 58° C. for 1 min. This suggests that TdT3-2 is significantly more active and thermostable than TdT1-3. As shown in Tables 2A and 2B, TdT3-2 carries most of the mutations identified from the top mutants from each round of screen, except T326S. Table 1 shows the amino acid sequence of TdT3-2.

At 47° C., commercial TdT and SUMO-TdT were denatured within 5 min as the intensities of the bands with incorporations remained the same for 5 min, 10 min and 20 min. In contrast, TdT3-2 was active for 20 min, as more incorporations could be seen for the 20 min reaction. At 58° C., commercial TdT and SUMO-TdT were not active, while TdT3-2 were denatured within 5 min as the intensity of the bands remains the same thereafter. This observation confirms that TdT3-2 is more thermostable than SUMO-TdT, and that TdT3-2 remains active at higher temperature.

Altogether, these data indicate that the nine amino acid substitutions identified in this example, individually or in any combination, can increase the thermostability of TdT mutants containing the amino acid substitution(s) while preserving the TdT catalytic activities. Furthermore, TdT mutants identified in this example can be thermostable while preserving TdT catalytic activities.

Example 2

Generating Single Stranded DNA Molecules Incorporating Multiple Modified Bases This example demonstrates using a TdT mutant to generate single stranded DNA (ssDNA) molecules incorporating multiple modified bases.

A scaffold (e.g., a single stranded DNA (ssDNA) scaffold) that incorporates modified nucleotides can be generated. The scaffold can serve as a "carrier" for multiple copies of a template molecule. The carrier with multiple copies of the template molecule can be a nanoparticle capable of occupying a single well (e.g., a microwell) on a substrate (e.g., a flow cell comprising multiple wells, such as 100, 1,000, 10,000 or more wells) by excluding other macromolecules from occupying the same well by steric clashes or hinderance. Single wells on a substrate each with one nanoparticle can result in monoclonality, or close in monoclonality. Alternatively, the ssDNA scaffold can carry a single copy of the template. The scaffold can have multiple copies of a reverse complement of an anchoring oligo or reverse complements of anchoring oligos. The scaffold can bind and sequester all the "anchoring" oligos in a given well because of the presence of the multiple copies of the reverse complement of the anchoring oligo or reverse complements of the anchoring oligos, thus enabling a single template to be captured per well.

One way to generate or construct such a ssDNA scaffold is using a ssDNA polymerase such as Terminal deoxynucleotidyl Transferase (TdT) to randomly incorporate nucleotides carrying modifications, such as azide groups on the bases, into a primer strand. However, commercially available TdTs do not readily incorporate multiple serial base modified nucleotides, presumably due to steric clashes.

A thermostable TdT mutant (referred to herein by TdT3-2 or CM12) was much better than a commercial NEB TdT at incorporating base-modified nucleotides. This property was discovered when a commercial TdT from NEB and TdT3-2 were tested for the incorporation of a nucleotide with a PEG chain conjugated to the base. NEB TdT generally stopped after incorporating 1-2 PEG-nucleotides, whereas TdT3-2 incorporated multiple PEG-nucleotides in series.

This mutant therefore represents an excellent catalyst for the generation of ssDNA carrying various types of base modified nucleotides for different purposes, including generation of the "carrier" of the present disclosure for monoclonal clustering.

FIG. 3 is non-limiting exemplary gel graph showing the attempted incorporation of Azide-PEG4-aminoallyl-dUTP (Jena Biosciences; #NU-1705S), referred to in this example as azide-PEG4-dUTP or Az-U, onto a 5-Carboxyfluorescein (5' FAM) labelled oligonucleotide primer by TdT3-2 or a commercial NEB TdT. As indicated above individual lanes, different reactions were set up with either TdT3-2 or NEB TdT, with 100% azide-PEG4-dUTP or 50% azide-PEG4-dUTP+50% dNTPs. Comparing lanes 1 and 3 in FIG. 3 shows that in 60 minutes, TdT3-2 was able to incorporate far more of the azide-PEG4-dUTP (see the products indicated by the asterisk next to lane 1) compared to the commercial TdT from NEB (see the products indicated by the asterisk next to lane 3). TdT3-2 showed greatly improved multiple incorporations in the presence of 100% azide-PEG4-dUTP compared to the commercial NEB TdT (compare bands next to asterisks). As shown in FIG. 3 lane 3, NEB TdT incorporated azide-PEG4-dUTP very slowly. NEB TdT was able to incorporate five to seven molecules of azide-PEG4-dUTP only after a long time such as 60 mins. Lanes 2 and 4 use a 50:50 mix of azide-PEG4-dUTP and dNTPs, whereupon NEB TdT showed plentiful nucleotide incorporation, indicating that the limited incorporation of 100% azide-PEG4-dUTP by NEB TdT seen in lane 3 was not due to lower activity, but rather steric clashes arising from serial incorporation of base modified nucleotides, consistent with the PEG modified nucleotides data.

Figure 4A:
FIGS. 4A-4B are non-limiting exemplary gel graphs showing the results of TdT extension with azide-PEG4-dUTP and natural nucleotides by a commercial NEB TdT for one minute and 60 minutes.
Figure 4B:
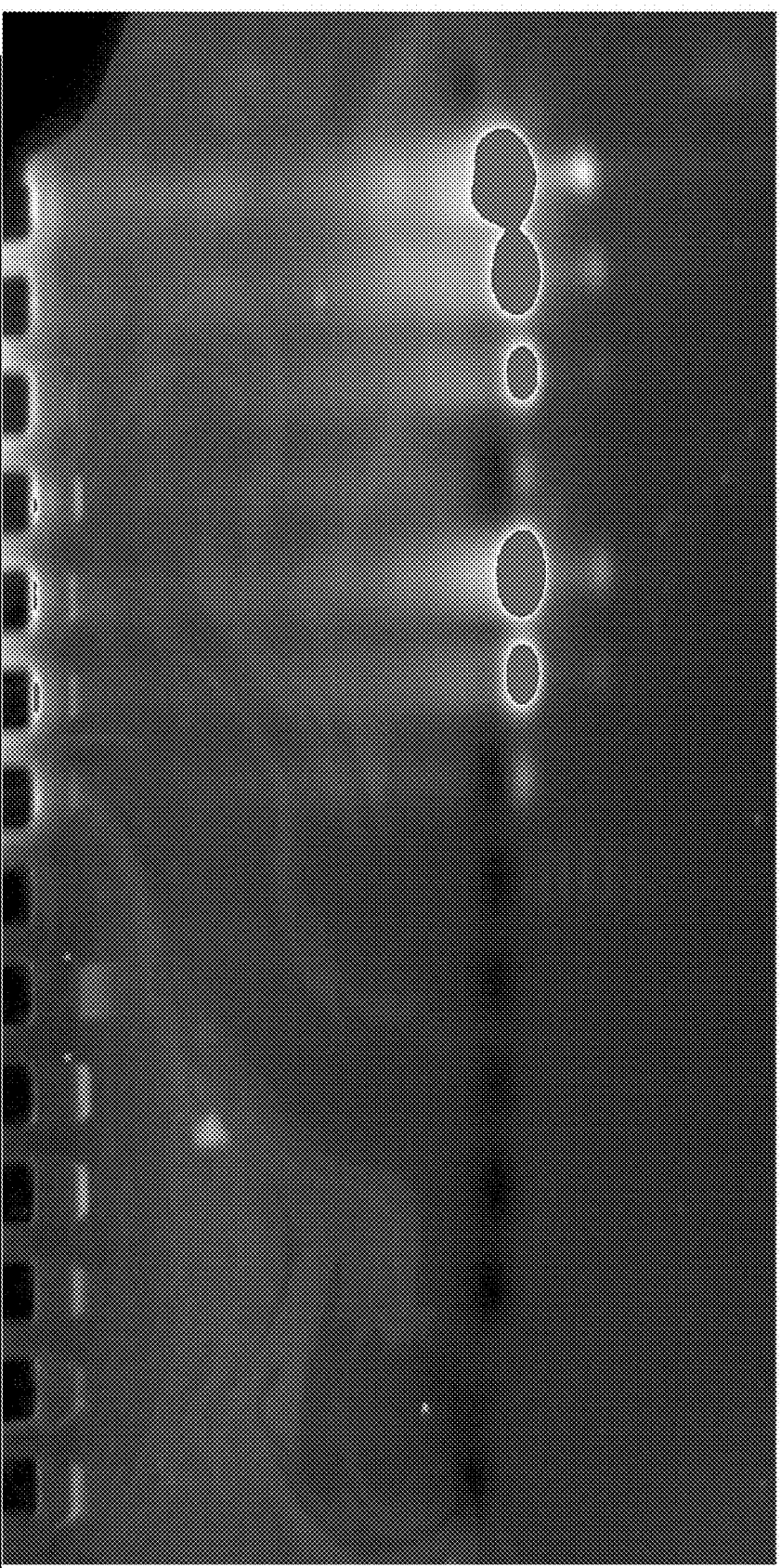

FIGS. 4A-4B are non-limiting exemplary gel graphs showing that results of TdT extension with azide-PEG4-dUTP and natural nucleotides by a commercial NEB TdT for one minute and 60 minutes. FIG. 4A shows that good incorporation was seen in 1 min (left hand side (LHS) half). The addition of dibenzocyclooctyne-Cy3 (DBCO-Cy3) seemed to work but was overshadowed by the high intensity of nucleotide-DBCO-Cy3 conjugate (blobs on right hand side (RHS) half). FIG. 4B shows that 60 mins incubation gave much higher molecular weight products. At higher azide-PEG4-dUTP nucleotide concentrations, the addition of DBCO-Cy3 led to disappearance of the products (see the asterisks on the LHS half and the RHS half), suggesting successful conjugation.

Figure 5C:
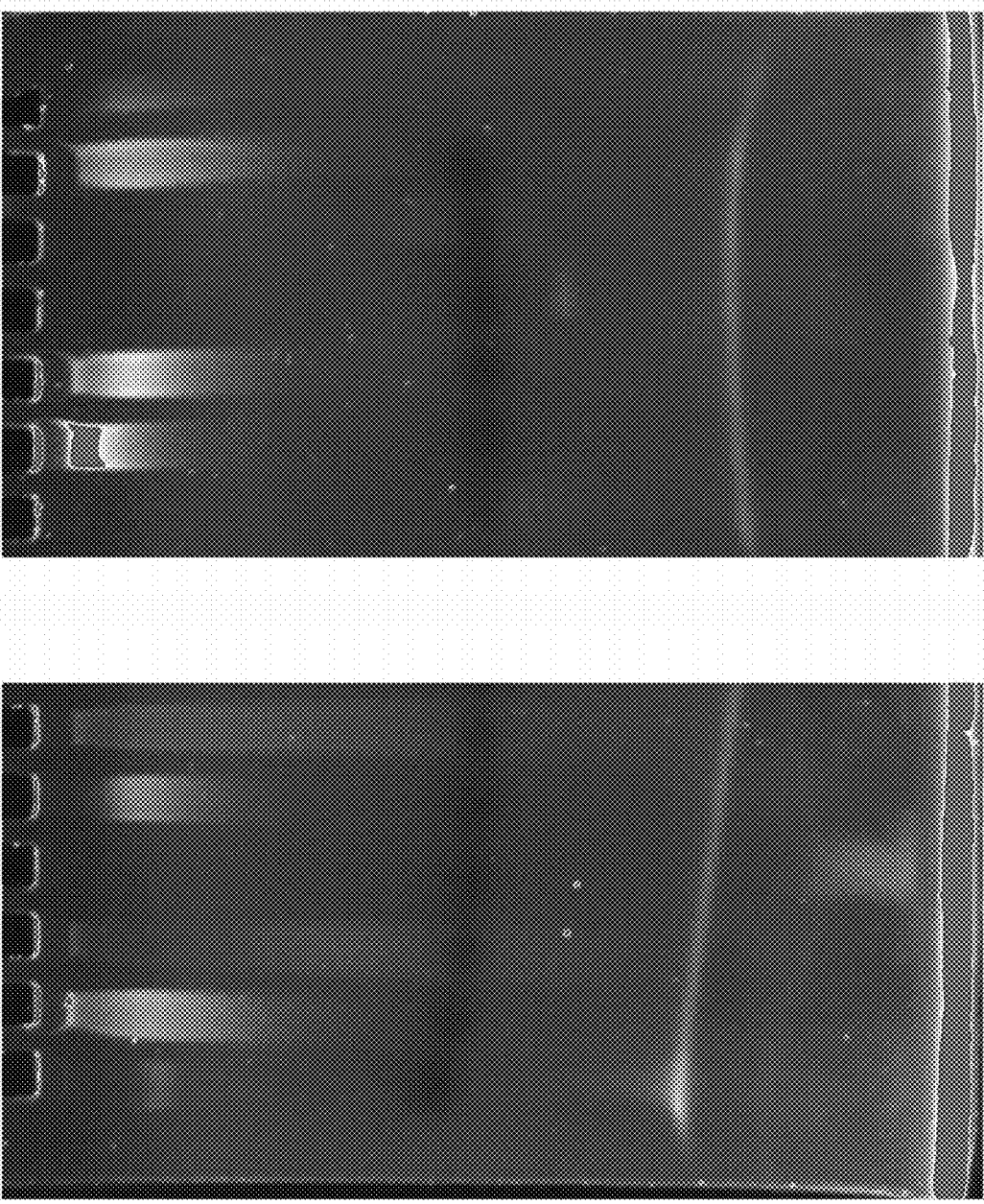

FIGS. 5A-5C are non-limiting exemplary gel graphs showing the results of TdT extension with azide-PEG4-dUTP or N6-(6-Azido)hexyl-dATP (referred to in this example as azide-hexyl-dATP, or Az-A) by TdT3-2 and a commercial NEB TdT. FIG. 5A shows that a few incorporations of Azide-dU were seen with TdT3-2, more than with NEB TdT. FIG. 5B shows that dozens of incorporations seen with pure azide-PEG4-dUTP (first lane on the left hand side). Mixing with dNTP gave high MW products with the NEB TdT; however, the proportion of azide-PEG4-dUTP being incorporated was unknown. PEG4-dUTP seemed to work better than azide-hexyl-dATP in the conditions tested. The gel visualized in FIG. 5B was stained with SYBR-Gold and visualized in FIG. 5C.

Thus, mutations in TdT3-2, apart from enabling higher thermostability, also enabled greater flexibility in the incorporation of base modified nucleotides. This property is of great interest in the generation of ssDNA scaffolds and in other applications where serial incorporation of base modified nucleotides is required. For example, TdT3-2 can be used as a catalyst for the generation of scaffolds containing serial additions of the Azide-PEG4-dUTP nucleotide. Suitable moieties will be then conjugated to the Azide groups using, for example, click chemistry.

Altogether, these data indicate that amino acid substitutions of TdT can improve thermostability and improve ability of TdT containing the amino acid substitutions to incorporate multiple base modified nucleotides.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of modifying a nucleic acid, the method comprising:
   (a) providing a single stranded deoxyribonucleic acid (ssDNA) and a nucleoside triphosphate comprising a modified base; and
   (b) contacting the ssDNA and the nucleoside triphosphate comprising the modified base with a recombinant terminal deoxynucleotidyl transferase (TdT) to generate a ssDNA scaffold, wherein the ssDNA scaffold comprises the ssDNA incorporated with one or more nucleotides comprising the modified base from the nucleoside triphosphate,
   wherein the recombinant TdT comprises an amino acid sequence that is at least 90% identical to SEQ ID NO: 1, and wherein the recombinant TdT comprises one or more amino acid substitution mutations at one or more positions corresponding to Glu191, Glu194, Asp242, Lys287, Met299, Thr342, and His421 in the *Bos taurus* TdT of SEQ ID NO: 12.

2. The method of claim 1, further comprising:
   (c) contacting the ssDNA scaffold with a first adapter oligonucleotide comprising a first adapter sequence and a second adapter oligonucleotide comprising a second adapter sequence to generate a nucleic acid carrier comprising the ssDNA scaffold attached to the first adapter oligonucleotide and the second adapter oligonucleotide.

3. The method of claim 2, wherein contacting the ssDNA scaffold with the first adapter oligonucleotide comprises contacting the ssDNA scaffold with a first adapter comprising the first adapter oligonucleotide and a first polymer.

4. The method of claim 2, wherein contacting the ssDNA scaffold with the second adapter oligonucleotide comprises contacting the ssDNA scaffold with a second adapter comprising the second adapter oligonucleotide and a second polymer.

5. The method of claim 2, wherein the ssDNA scaffold comprises a third polymer.

6. The method of claim 2, further comprising:
   (d) providing a nucleic acid template comprising the first adapter sequence, or a reverse complement thereof, the second adapter sequence, or a reverse complement thereof, and a nucleic acid hybridization sequence;
   (e) contacting the nucleic acid carrier with the nucleic acid template to generate the nucleic acid carrier having the nucleic acid template hybridized to a template capture site of the nucleic acid carrier via the nucleic acid hybridization sequence of the nucleic acid template;
   (f) performing amplification on the nucleic acid carrier hybridized with the nucleic acid template to generate a plurality of amplified nucleic acids each comprising the first adapter oligonucleotides and the second adapter oligonucleotides extended to comprise a sequence of the nucleic acid template, or a reverse complement thereof; and
   (g) determining the sequence of the nucleic acid template using the plurality of amplified nucleic acids.

7. A method of modifying a nucleic acid, the method comprising:
   (a) providing a first nucleic acid and a first nucleoside triphosphate comprising a first modified base; and
   (b) contacting the first nucleic acid and the first nucleoside triphosphate comprising the first modified base with a recombinant terminal deoxynucleotidyl transferase (TdT) for a first reaction time at a first temperature in a first reaction to generate a second nucleic acid, wherein the second nucleic acid comprises the first nucleic acid incorporated with one or more first nucleotides comprising the first modified base from the first nucleoside triphosphate,
   wherein the recombinant TdT comprises an amino acid sequence that is at least 90% identical to SEQ ID NO: 1, and wherein the recombinant TdT comprises one or more amino acid substitution mutations at one or more positions corresponding to Glu191, Glu194, Asp242, Lys287, Met299, Thr342, and His421 in the *Bos taurus* TdT of SEQ ID NO: 12.

8. The method of claim 7, wherein one or more of the first nucleic acid and the second nucleic acid comprise a single stranded nucleic acid, a double stranded nucleic acid with a 3' overhang, a double stranded nucleic acid with a 3' recess, or a combination thereof.

9. The method of claim 7, wherein the first modified base of the first nucleoside triphosphate comprises a modified adenine, a modified guanine, a modified cytosine, a modified thymine, or a modified uracil.

10. The method of claim 7, wherein the first nucleoside triphosphate comprises the first modified base and a first accessory oligonucleotide covalently linked.

11. The method of claim 7,
    wherein providing the first nucleic acid and the first nucleoside triphosphate comprising the first modified base comprises: providing the first nucleic acid, the first nucleoside triphosphate comprising the first modified base, and a second nucleoside triphosphate,
    wherein contacting the first nucleic acid and the first nucleoside triphosphate comprising the first modified base with the recombinant TdT comprises: contacting the first nucleic acid, the first nucleoside triphosphate comprising the first modified base, and the second nucleoside triphosphate with the recombinant TdT for the first reaction time at the first temperature in the first reaction to generate the second nucleic acid, and wherein the second nucleic acid comprises the first nucleic acid incorporated with (i) one or more of the first nucleotides comprising the first modified base from the first nucleoside triphosphate and (ii) one or more second nucleotides.

12. The method of claim 7,
wherein providing the first nucleic acid and the first nucleoside triphosphate comprising the first modified base comprises: providing the first nucleic acid, the first nucleoside triphosphate comprising the first modified base, and a plurality of second nucleoside triphosphates,
wherein contacting the first nucleic acid and the first nucleoside triphosphate comprising the first modified base with the recombinant TdT comprises: contacting the first nucleic acid, the first nucleoside triphosphate comprising the first modified base, and the plurality of second nucleoside triphosphates with the recombinant TdT for the first reaction time at the first temperature in the first reaction to generate the second nucleic acid, and
wherein the second nucleic acid comprises the first nucleic acid incorporated with one or more of the first nucleotides comprising the first modified base and one or more second nucleotides from the plurality of second nucleoside triphosphates.

13. The method of claim 7, wherein modified bases and unmodified bases of nucleotides are incorporated into the second nucleic acid at a ratio that ranges from about 1:100 to about 100:1.

14. The method of claim 7, wherein the modified bases are distributed randomly throughout the second nucleic acid.

15. The method of claim 7, wherein the first nucleic acid comprises a template capture site capable of binding a nucleic acid template.

16. The method of claim 7, wherein one or more of the first modified base of the first nucleoside triphosphate and the first nucleotide in the second nucleic acid comprise a functional moiety.

17. The method of claim 16, wherein the functional moiety of the first modified base is capable of participating in a click chemistry reaction.

18. The method of claim 15, further comprising:
providing a first accessory oligonucleotide; and
contacting the second nucleic acid with the first accessory oligonucleotide for a second reaction time at a second temperature in a second reaction to generate a third nucleic acid comprising the second nucleic acid attached to one or more of the first accessory oligonucleotides.

19. The method of claim 18, wherein the first accessory oligonucleotide comprises a first adapter sequence, or a reverse complement thereof.

20. The method of claim 19, further comprising:
(c) providing the nucleic acid template comprising the first adapter sequence, or a reverse complement thereof, a second adapter sequence, or a reverse complement thereof, and a nucleic acid hybridization sequence capable of hybridizing to the template capture site on the third nucleic acid;
(d) contacting the third nucleic acid with the nucleic acid template to generate the third nucleic acid with the nucleic acid template hybridized to the template capture site on the third nucleic acid via the nucleic acid hybridization sequence of the nucleic acid template;
(e) performing amplification on the third nucleic acid hybridized with the nucleic acid template to generate a fourth nucleic acid comprising the third nucleic acid attached to one or more of the first accessory oligonucleotides and one or more of a second accessory oligonucleotides extended to comprise a sequence of the nucleic acid template, or a reverse complement thereof; and
(f) determining the sequence of the nucleic acid template using the fourth nucleic acid.

21. The method of claim 7, wherein the recombinant TdT further comprises an amino acid substitution mutation at a position corresponding to Lys 193 in the *Bos taurus* TdT of SEQ ID NO: 12.

22. The method of claim 21, wherein the amino acid substitution mutation at the position corresponding to Lys193 in the *Bos taurus* TdT of SEQ ID NO: 12 is Lys193Asn.

23. The method of claim 7, wherein the recombinant TdT further comprises an amino acid substitution mutation at a position corresponding to Phe296 in the *Bos taurus* TdT of SEQ ID NO: 12.

24. The method of claim 23, wherein the amino acid substitution mutation at the position corresponding to Phe296 in the *Bos taurus* TdT of SEQ ID NO: 12 is Phe296Leu.

* * * * *

SEQUENCE LISTING

```
<160> NUMBER OF SEQ ID NOS: 15

<210> SEQ ID NO 1
<211> LENGTH: 382
<212> TYPE: PRT
<213> ORGANISM: Artificial Sequence
<220> FEATURE:
<223> OTHER INFORMATION: Bos taurus TdT 139-520
<220> FEATURE:
<221> NAME/KEY: NON_TER
<222> LOCATION: (1)..(1)

<400> SEQUENCE: 1

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
```

```
                35                  40                  45

Ala Glu Asn Ser Glu Phe Lys Glu Asn Glu Val Ser Tyr Val Thr Phe
 50                  55                  60

Met Arg Ala Ala Ser Val Leu Lys Ser Leu Pro Phe Thr Ile Ile Ser
 65                  70                  75                  80

Met Lys Asp Thr Glu Gly Ile Pro Cys Leu Gly Asp Lys Val Lys Cys
                 85                  90                  95

Ile Ile Glu Glu Ile Ile Glu Asp Gly Glu Ser Ser Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
370                 375                 380

<210> SEQ ID NO 2
<211> LENGTH: 382
<212> TYPE: PRT
<213> ORGANISM: Artificial Sequence
<220> FEATURE:
<223> OTHER INFORMATION: TdT 139-520 with Glu53Val in TdT
      139-520/Glu191Val in WT
<220> FEATURE:
<221> NAME/KEY: NON_TER
<222> LOCATION: (1)..(1)

<400> SEQUENCE: 2
```

```
Arg Thr Asp Tyr Ser Ala Thr Pro Asn Pro Gly Phe Gln Lys Thr Pro
 1               5                  10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Val Phe Lys Glu Asn Glu Val Ser Tyr Val Thr Phe
 50                  55                  60

Met Arg Ala Ala Ser Val Leu Lys Ser Leu Pro Phe Thr Ile Ile Ser
 65              70                  75                      80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
 130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Val Gly Val Leu Val Lys Glu Ala Val
        180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270

Phe Gln Lys Cys Phe Leu Ile Leu Lys Leu His His Gln Arg Val Asp
                275                 280                 285

Ser Ser Lys Ser Asn Gln Gln Glu Gly Lys Thr Trp Lys Ala Ile Arg
        290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
                340                 345                 350

Thr Lys Arg Val Phe Leu Lys Ala Glu Ser Glu Glu Ile Phe Ala
        355                 360                 365

His Leu Gly Leu Asp Tyr Ile Glu Pro Trp Glu Arg Asn Ala
370                 375                 380
```

<210> SEQ ID NO 3
<211> LENGTH: 382
<212> TYPE: PRT
<213> ORGANISM: Artificial Sequence
<220> FEATURE:
<223> OTHER INFORMATION: TdT 139-520 with Lys55Asn in TdT

```
        139-520/Lys193Asn in WT
<220> FEATURE:
<221> NAME/KEY: NON_TER
<222> LOCATION: (1)..(1)

<400> SEQUENCE: 3

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Glu Phe Asn Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
    195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Glu Ile Phe Ala
    355                 360                 365

His Leu Gly Leu Asp Tyr Ile Glu Pro Trp Glu Arg Asn Ala
    370                 375                 380
```

<210> SEQ ID NO 4
<211> LENGTH: 382
<212> TYPE: PRT
<213> ORGANISM: Artificial Sequence
<220> FEATURE:
<223> OTHER INFORMATION: TdT 139-520 with Glu56Gly in TdT
      139-520/Glu194Gly in WT TdT
<220> FEATURE:
<221> NAME/KEY: NON_TER
<222> LOCATION: (1)..(1)

<400> SEQUENCE: 4

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Gly Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

```
Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
        370                 375                 380

<210> SEQ ID NO 5
<211> LENGTH: 382
<212> TYPE: PRT
<213> ORGANISM: Artificial Sequence
<220> FEATURE:
<223> OTHER INFORMATION: TdT 139-520 with Asp104Tyr in TdT
      139-520/Asp242Tyr in WT TdT
<220> FEATURE:
<221> NAME/KEY: NON_TER
<222> LOCATION: (1)..(1)

<400> SEQUENCE: 5

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Tyr Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
        275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
```

```
                305                 310                 315                 320
Gly Trp Thr Gly Ser Arg Gln Phe Glu Arg Asp Ile Arg Arg Tyr Ala
                    325                 330                 335

Thr His Glu Arg Lys Met Met Leu Asp Asn His Ala Leu Tyr Asp Lys
                    340                 345                 350

Thr Lys Arg Val Phe Leu Lys Ala Glu Ser Glu Glu Ile Phe Ala
                    355                 360                 365

His Leu Gly Leu Asp Tyr Ile Glu Pro Trp Glu Arg Asn Ala
                    370                 375                 380

<210> SEQ ID NO 6
<211> LENGTH: 382
<212> TYPE: PRT
<213> ORGANISM: Artificial Sequence
<220> FEATURE:
<223> OTHER INFORMATION: TdT 139-520 with Lys149Glu in TdT
      139-520/Lys287Glu in WT TdT
<220> FEATURE:
<221> NAME/KEY: NON_TER
<222> LOCATION: (1)..(1)

<400> SEQUENCE: 6

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Glu Phe Lys Glu Asn Glu Val Ser Tyr Val Thr Phe
        50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
        130                 135                 140

Arg Ser Leu Ser Glu Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
                180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
        210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270
```

```
Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
        290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
                340                 345                 350

Thr Lys Arg Val Phe Leu Lys Ala Glu Ser Glu Glu Ile Phe Ala
                355                 360                 365

His Leu Gly Leu Asp Tyr Ile Glu Pro Trp Glu Arg Asn Ala
        370                 375                 380

<210> SEQ ID NO 7
<211> LENGTH: 382
<212> TYPE: PRT
<213> ORGANISM: Artificial Sequence
<220> FEATURE:
<223> OTHER INFORMATION: TdT 139-520 with Phe158Leu in TdT
      139-520/Phe296Leu in WT TdT.
<220> FEATURE:
<221> NAME/KEY: NON_TER
<222> LOCATION: (1)..(1)

<400> SEQUENCE: 7

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Leu Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
        195                 200                 205

Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240
```

```
Trp Glu Lys Lys Gly Leu Leu Tyr Tyr Asp Leu Val Glu Ser Thr
            245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
            325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Glu Ile Phe Ala
            355                 360                 365

His Leu Gly Leu Asp Tyr Ile Glu Pro Trp Glu Arg Asn Ala
            370                 375                 380

<210> SEQ ID NO 8
<211> LENGTH: 382
<212> TYPE: PRT
<213> ORGANISM: Artificial Sequence
<220> FEATURE:
<223> OTHER INFORMATION: TdT 139-520 with Met161Lys in TdT
      139-520/Met299Lys in WT TdT
<220> FEATURE:
<221> NAME/KEY: NON_TER
<222> LOCATION: (1)..(1)

<400> SEQUENCE: 8

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
        35                  40                  45

Ala Glu Asn Ser Glu Phe Lys Glu Asn Glu Val Ser Tyr Val Thr Phe
    50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
        115                 120                 125

Phe Gly Val Gly Leu Lys Thr Ser Glu Lys Trp Phe Arg Met Gly Phe
    130                 135                 140

Arg Ser Leu Ser Lys Ile Met Ser Asp Lys Thr Leu Lys Phe Thr Lys
145                 150                 155                 160

Lys Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
```

```
                195                 200                 205
Arg Gly Lys Lys Ile Gly His Asp Val Asp Phe Leu Ile Thr Ser Pro
210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
                260                 265                 270

Phe Gln Lys Cys Phe Leu Ile Leu Lys Leu His His Gln Arg Val Asp
                275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
                340                 345                 350

Thr Lys Arg Val Phe Leu Lys Ala Glu Ser Glu Glu Glu Ile Phe Ala
                355                 360                 365

His Leu Gly Leu Asp Tyr Ile Glu Pro Trp Glu Arg Asn Ala
370                 375                 380

<210> SEQ ID NO 9
<211> LENGTH: 382
<212> TYPE: PRT
<213> ORGANISM: Artificial Sequence
<220> FEATURE:
<223> OTHER INFORMATION: TdT 139-520 with Thr204Ser in TdT
      139-520/Thr342Ser in WT TdT
<220> FEATURE:
<221> NAME/KEY: NON_TER
<222> LOCATION: (1)..(1)

<400> SEQUENCE: 9

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
                35                  40                  45

Ala Glu Asn Ser Glu Phe Lys Glu Asn Glu Val Ser Tyr Val Thr Phe
50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
                100                 105                 110

Val Leu Asn Asp Glu Arg Tyr Gln Ser Phe Lys Leu Phe Thr Ser Val
                115                 120                 125

Phe Gly Val Gly Leu Lys Thr Ser Glu Lys Trp Phe Arg Met Gly Phe
130                 135                 140

Arg Ser Leu Ser Lys Ile Met Ser Asp Lys Thr Leu Lys Phe Thr Lys
145                 150                 155                 160
```

```
Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Ser Gly Gly Phe Arg
            195                 200                 205

Arg Gly Lys Lys Ile Gly His Asp Val Asp Phe Leu Ile Thr Ser Pro
            210                 215                 220

Gly Ser Ala Glu Asp Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
            245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu His His Gln Arg Val Asp
            275                 280                 285

Ser Ser Lys Ser Asn Gln Gln Glu Gly Lys Thr Trp Lys Ala Ile Arg
            290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
370                 375                 380

<210> SEQ ID NO 10
<211> LENGTH: 382
<212> TYPE: PRT
<213> ORGANISM: Artificial Sequence
<220> FEATURE:
<223> OTHER INFORMATION: TdT 139-520 with His283Pro in TdT
      139-520/His421Pro in WT TdT
<220> FEATURE:
<221> NAME/KEY: NON_TER
<222> LOCATION: (1)..(1)

<400> SEQUENCE: 10

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
            20                  25                  30

Thr Leu Asn Asn Tyr Asn His Ile Phe Thr Asp Ala Phe Glu Ile Leu
            35                  40                  45

Ala Glu Asn Ser Glu Phe Lys Glu Asn Glu Val Ser Tyr Val Thr Phe
            50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

Ile Ile Glu Glu Ile Ile Glu Asp Gly Glu Ser Ser Glu Val Lys Ala
            100                 105                 110

Val Leu Asn Asp Glu Arg Tyr Gln Ser Phe Lys Leu Phe Thr Ser Val
            115                 120                 125
```

Phe Gly Val Gly Leu Lys Thr Ser Glu Lys Trp Phe Arg Met Gly Phe
            130                 135                 140

Arg Ser Leu Ser Lys Ile Met Ser Asp Lys Thr Leu Lys Phe Thr Lys
145                 150                 155                 160

Met Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
            210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu Pro His Gln Arg Val Asp
            275                 280                 285

Ser Ser Lys Ser Asn Gln Gln Glu Gly Lys Thr Trp Lys Ala Ile Arg
290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
            370                 375                 380

<210> SEQ ID NO 11
<211> LENGTH: 382
<212> TYPE: PRT
<213> ORGANISM: Artificial Sequence
<220> FEATURE:
<223> OTHER INFORMATION: TdT 139-520 with TdT3-2 Substitution Mutations
<220> FEATURE:
<221> NAME/KEY: NON_TER
<222> LOCATION: (1)..(1)

<400> SEQUENCE: 11

Arg Thr Asp Tyr Ser Ala Thr Pro Asn Pro Gly Phe Gln Lys Thr Pro
1               5                   10                  15

Pro Leu Ala Val Lys Lys Ile Ser Gln Tyr Ala Cys Gln Arg Lys Thr
                20                  25                  30

Thr Leu Asn Asn Tyr Asn His Ile Phe Thr Asp Ala Phe Glu Ile Leu
            35                  40                  45

Ala Glu Asn Ser Val Phe Asn Gly Asn Glu Val Ser Tyr Val Thr Phe
50                  55                  60

Met Arg Ala Ala Ser Val Leu Lys Ser Leu Pro Phe Thr Ile Ile Ser
65                  70                  75                  80

Met Lys Asp Thr Glu Gly Ile Pro Cys Leu Gly Asp Lys Val Lys Cys
                85                  90                  95

```
Ile Ile Glu Glu Ile Ile Glu Tyr Gly Glu Ser Ser Glu Val Lys Ala
            100                 105                 110

Val Leu Asn Asp Glu Arg Tyr Gln Ser Phe Lys Leu Phe Thr Ser Val
            115                 120                 125

Phe Gly Val Gly Leu Lys Thr Ser Glu Lys Trp Phe Arg Met Gly Phe
    130                 135                 140

Arg Ser Leu Ser Glu Ile Met Ser Asp Lys Thr Leu Lys Leu Thr Lys
145                 150                 155                 160

Lys Gln Lys Ala Gly Phe Leu Tyr Tyr Glu Asp Leu Val Ser Cys Val
                165                 170                 175

Thr Arg Ala Glu Ala Glu Ala Val Gly Val Leu Val Lys Glu Ala Val
            180                 185                 190

Trp Ala Phe Leu Pro Asp Ala Phe Val Thr Met Thr Gly Gly Phe Arg
            195                 200                 205

Arg Gly Lys Lys Ile Gly His Asp Val Asp Phe Leu Ile Thr Ser Pro
    210                 215                 220

Gly Ser Ala Glu Asp Glu Glu Gln Leu Leu Pro Lys Val Ile Asn Leu
225                 230                 235                 240

Trp Glu Lys Lys Gly Leu Leu Leu Tyr Tyr Asp Leu Val Glu Ser Thr
                245                 250                 255

Phe Glu Lys Phe Lys Leu Pro Ser Arg Gln Val Asp Thr Leu Asp His
            260                 265                 270

Phe Gln Lys Cys Phe Leu Ile Leu Lys Leu Pro His Gln Arg Val Asp
            275                 280                 285

Ser Ser Lys Ser Asn Gln Gln Glu Gly Lys Thr Trp Lys Ala Ile Arg
    290                 295                 300

Val Asp Leu Val Met Cys Pro Tyr Glu Asn Arg Ala Phe Ala Leu Leu
305                 310                 315                 320

Gly Trp Thr Gly Ser Arg Gln Phe Glu Arg Asp Ile Arg Arg Tyr Ala
                325                 330                 335

Thr His Glu Arg Lys Met Met Leu Asp Asn His Ala Leu Tyr Asp Lys
            340                 345                 350

Thr Lys Arg Val Phe Leu Lys Ala Glu Ser Glu Glu Ile Phe Ala
            355                 360                 365

His Leu Gly Leu Asp Tyr Ile Glu Pro Trp Glu Arg Asn Ala
    370                 375                 380

<210> SEQ ID NO 12
<211> LENGTH: 520
<212> TYPE: PRT
<213> ORGANISM: Bos taurus

<400> SEQUENCE: 12

Met Ala Gln Gln Arg Gln His Gln Arg Leu Pro Met Asp Pro Leu Cys
1               5                   10                  15

Thr Ala Ser Ser Gly Pro Arg Lys Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
```

```
                      85                  90                  95
Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
            115                 120                 125

Glu Ile Thr Gly Lys His Gln Leu Val Val Arg Thr Asp Tyr Ser Ala
            130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
            195                 200                 205

Leu Lys Ser Leu Pro Phe Thr Ile Ile Ser Met Lys Asp Thr Glu Gly
            210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
                260                 265                 270

Thr Ser Glu Lys Trp Phe Arg Met Gly Phe Arg Ser Leu Ser Lys Ile
            275                 280                 285

Met Ser Asp Lys Thr Leu Lys Phe Thr Lys Met Gln Lys Ala Gly Phe
290                 295                 300

Leu Tyr Tyr Glu Asp Leu Val Ser Cys Val Thr Arg Ala Glu Ala Glu
305                 310                 315                 320

Ala Val Gly Val Leu Val Lys Glu Ala Val Trp Ala Phe Leu Pro Asp
            325                 330                 335

Ala Phe Val Thr Met Thr Gly Gly Phe Arg Arg Gly Lys Lys Ile Gly
            340                 345                 350

His Asp Val Asp Phe Leu Ile Thr Ser Pro Gly Ser Ala Glu Asp Glu
            355                 360                 365

Glu Gln Leu Leu Pro Lys Val Ile Asn Leu Trp Glu Lys Lys Gly Leu
            370                 375                 380

Leu Leu Tyr Tyr Asp Leu Val Glu Ser Thr Phe Glu Lys Phe Lys Leu
385                 390                 395                 400

Pro Ser Arg Gln Val Asp Thr Leu Asp His Phe Gln Lys Cys Phe Leu
                405                 410                 415

Ile Leu Lys Leu His His Gln Arg Val Asp Ser Ser Lys Ser Asn Gln
                420                 425                 430

Gln Glu Gly Lys Thr Trp Lys Ala Ile Arg Val Asp Leu Val Met Cys
            435                 440                 445

Pro Tyr Glu Asn Arg Ala Phe Ala Leu Leu Gly Trp Thr Gly Ser Arg
450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
                485                 490                 495

Lys Ala Glu Ser Glu Glu Glu Ile Phe Ala His Leu Gly Leu Asp Tyr
            500                 505                 510
```

Ile Glu Pro Trp Glu Arg Asn Ala
        515                 520

<210> SEQ ID NO 13
<211> LENGTH: 98
<212> TYPE: PRT
<213> ORGANISM: Artificial Sequence
<220> FEATURE:
<223> OTHER INFORMATION: Saccharomyces cerevisiae SUMO 1-98
<220> FEATURE:
<221> NAME/KEY: NON_TER
<222> LOCATION: (98)..(98)

<400> SEQUENCE: 13

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 14
<211> LENGTH: 504
<212> TYPE: PRT
<213> ORGANISM: Artificial Sequence
<220> FEATURE:
<223> OTHER INFORMATION: HIS-SUMO-TdT 139-520

<400> SEQUENCE: 14

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Glu Leu Met Arg Thr Asp Tyr Ser Ala
        115                 120                 125

Thr Pro Asn Pro Gly Phe Gln Lys Thr Pro Pro Leu Ala Val Lys Lys
    130                 135                 140

Ile Ser Gln Tyr Ala Cys Gln Arg Lys Thr Thr Leu Asn Asn Tyr Asn
145                 150                 155                 160

His Ile Phe Thr Asp Ala Phe Glu Ile Leu Ala Glu Asn Ser Glu Phe
                165                 170                 175

```
Lys Glu Asn Glu Val Ser Tyr Val Thr Phe Met Arg Ala Ala Ser Val
            180                 185                 190
Leu Lys Ser Leu Pro Phe Thr Ile Ile Ser Met Lys Asp Thr Glu Gly
        195                 200                 205
Ile Pro Cys Leu Gly Asp Lys Val Lys Cys Ile Ile Glu Glu Ile Ile
    210                 215                 220
Glu Asp Gly Glu Ser Ser Glu Val Lys Ala Val Leu Asn Asp Glu Arg
225                 230                 235                 240
Tyr Gln Ser Phe Lys Leu Phe Thr Ser Val Phe Gly Val Gly Leu Lys
                245                 250                 255
Thr Ser Glu Lys Trp Phe Arg Met Gly Phe Arg Ser Leu Ser Lys Ile
            260                 265                 270
Met Ser Asp Lys Thr Leu Lys Phe Thr Lys Met Gln Lys Ala Gly Phe
        275                 280                 285
Leu Tyr Tyr Glu Asp Leu Val Ser Cys Val Thr Arg Ala Glu Ala Glu
    290                 295                 300
Ala Val Gly Val Leu Val Lys Glu Ala Val Trp Ala Phe Leu Pro Asp
305                 310                 315                 320
Ala Phe Val Thr Met Thr Gly Gly Phe Arg Arg Gly Lys Lys Ile Gly
                325                 330                 335
His Asp Val Asp Phe Leu Ile Thr Ser Pro Gly Ser Ala Glu Asp Glu
            340                 345                 350
Glu Gln Leu Leu Pro Lys Val Ile Asn Leu Trp Glu Lys Lys Gly Leu
        355                 360                 365
Leu Leu Tyr Tyr Asp Leu Val Glu Ser Thr Phe Glu Lys Phe Lys Leu
    370                 375                 380
Pro Ser Arg Gln Val Asp Thr Leu Asp His Phe Gln Lys Cys Phe Leu
385                 390                 395                 400
Ile Leu Lys Leu His His Gln Arg Val Asp Ser Ser Lys Ser Asn Gln
                405                 410                 415
Gln Glu Gly Lys Thr Trp Lys Ala Ile Arg Val Asp Leu Val Met Cys
            420                 425                 430
Pro Tyr Glu Asn Arg Ala Phe Ala Leu Leu Gly Trp Thr Gly Ser Arg
        435                 440                 445
Gln Phe Glu Arg Asp Ile Arg Arg Tyr Ala Thr His Glu Arg Lys Met
    450                 455                 460
Met Leu Asp Asn His Ala Leu Tyr Asp Lys Thr Lys Arg Val Phe Leu
465                 470                 475                 480
Lys Ala Glu Ser Glu Glu Ile Phe Ala His Leu Gly Leu Asp Tyr
                485                 490                 495
Ile Glu Pro Trp Glu Arg Asn Ala
            500

<210> SEQ ID NO 15
<211> LENGTH: 504
<212> TYPE: PRT
<213> ORGANISM: Artificial Sequence
<220> FEATURE:
<223> OTHER INFORMATION: TdT3-2

<400> SEQUENCE: 15

Met Gly Ser Ser His His His His His His Gly Ser Gly Leu Val Pro
1               5                   10                  15
Arg Gly Ser Ala Ser Met Ser Asp Ser Glu Val Asn Gln Glu Ala Lys
            20                  25                  30
```

-continued

```
Pro Glu Val Lys Pro Glu Val Lys Pro Glu Thr His Ile Asn Leu Lys
            35                  40                  45
Val Ser Asp Gly Ser Ser Glu Ile Phe Phe Lys Ile Lys Lys Thr Thr
 50                  55                  60
Pro Leu Arg Arg Leu Met Glu Ala Phe Ala Lys Arg Gln Gly Lys Glu
 65                  70                  75                  80
Met Asp Ser Leu Arg Phe Leu Tyr Asp Gly Ile Arg Ile Gln Ala Asp
                    85                  90                  95
Gln Thr Pro Glu Asp Leu Asp Met Glu Asp Asn Asp Ile Ile Glu Ala
            100                 105                 110
His Arg Glu Gln Ile Gly Gly Glu Leu Met Arg Thr Asp Tyr Ser Ala
            115                 120                 125
Thr Pro Asn Pro Gly Phe Gln Lys Thr Pro Pro Leu Ala Val Lys Lys
130                 135                 140
Ile Ser Gln Tyr Ala Cys Gln Arg Lys Thr Thr Leu Asn Asn Tyr Asn
145                 150                 155                 160
His Ile Phe Thr Asp Ala Phe Glu Ile Leu Ala Glu Asn Ser Val Phe
                    165                 170                 175
Asn Gly Asn Glu Val Ser Tyr Val Thr Phe Met Arg Ala Ala Ser Val
            180                 185                 190
Leu Lys Ser Leu Pro Phe Thr Ile Ile Ser Met Lys Asp Thr Glu Gly
            195                 200                 205
Ile Pro Cys Leu Gly Asp Lys Val Lys Cys Ile Ile Glu Glu Ile Ile
210                 215                 220
Glu Tyr Gly Glu Ser Ser Glu Val Lys Ala Val Leu Asn Asp Glu Arg
225                 230                 235                 240
Tyr Gln Ser Phe Lys Leu Phe Thr Ser Val Phe Gly Val Gly Leu Lys
                    245                 250                 255
Thr Ser Glu Lys Trp Phe Arg Met Gly Phe Arg Ser Leu Ser Glu Ile
            260                 265                 270
Met Ser Asp Lys Thr Leu Lys Leu Thr Lys Lys Gln Lys Ala Gly Phe
            275                 280                 285
Leu Tyr Tyr Glu Asp Leu Val Ser Cys Val Thr Arg Ala Glu Ala Glu
            290                 295                 300
Ala Val Gly Val Leu Val Lys Glu Ala Val Trp Ala Phe Leu Pro Asp
305                 310                 315                 320
Ala Phe Val Thr Met Thr Gly Gly Phe Arg Arg Gly Lys Lys Ile Gly
                    325                 330                 335
His Asp Val Asp Phe Leu Ile Thr Ser Pro Gly Ser Ala Glu Asp Glu
            340                 345                 350
Glu Gln Leu Leu Pro Lys Val Ile Asn Leu Trp Glu Lys Lys Gly Leu
            355                 360                 365
Leu Leu Tyr Tyr Asp Leu Val Glu Ser Thr Phe Glu Lys Phe Lys Leu
            370                 375                 380
Pro Ser Arg Gln Val Asp Thr Leu Asp His Phe Gln Lys Cys Phe Leu
385                 390                 395                 400
Ile Leu Lys Leu Pro His Gln Arg Val Asp Ser Ser Lys Ser Asn Gln
                    405                 410                 415
Gln Glu Gly Lys Thr Trp Lys Ala Ile Arg Val Asp Leu Val Met Cys
            420                 425                 430
Pro Tyr Glu Asn Arg Ala Phe Ala Leu Leu Gly Trp Thr Gly Ser Arg
            435                 440                 445
```

-continued

```
Gln Phe Glu Arg Asp Ile Arg Arg Tyr Ala Thr His Glu Arg Lys Met
    450                 455                 460

Met Leu Asp Asn His Ala Leu Tyr Asp Lys Thr Lys Arg Val Phe Leu
465                 470                 475                 480

Lys Ala Glu Ser Glu Glu Ile Phe Ala His Leu Gly Leu Asp Tyr
                485                 490                 495

Ile Glu Pro Trp Glu Arg Asn Ala
                500
```